United States Patent
Ametamey et al.

(10) Patent No.: US 11,655,243 B2
(45) Date of Patent: May 23, 2023

(54) PYRIDINE AND PYRAZINE DERIVATIVES AS PREFERENTIAL CANNABINOID 2 AGONISTS

(71) Applicants: HOFFMANN-LA ROCHE INC., Little Falls, NJ (US); EIDGENOESSISCHE TECHNISCHE HOCHSCHULE ZUERICH, Zurich (CH)

(72) Inventors: Simon M. Ametamey, Zurich (CH); Kenneth Atz, Basel (CH); Luca Gobbi, Basel (CH); Uwe Grether, Basel (CH); Wolfgang Guba, Basel (CH); Julian Kretz, Basel (CH)

(73) Assignees: HOFFMANN-LA ROCHE INC., Little Falls, NJ (US); EIDGENOESSISCHE TECHNISCHE HOCHSCHULE ZUERICH, Zurich (CH)

( * ) Notice: Subject to any disclaimer, the term of this patent is extended or adjusted under 35 U.S.C. 154(b) by 155 days.

(21) Appl. No.: 17/125,647

(22) Filed: Dec. 17, 2020

(65) Prior Publication Data

US 2021/0115027 A1    Apr. 22, 2021

Related U.S. Application Data

(63) Continuation of application No. PCT/EP2019/066733, filed on Jun. 25, 2019.

(30) Foreign Application Priority Data

Jun. 27, 2018 (EP) .................................. 18180114

(51) Int. Cl.
| | | |
|---|---|---|
| C07D 401/04 | (2006.01) |
| C07D 403/04 | (2006.01) |
| A61K 31/497 | (2006.01) |
| C07D 405/14 | (2006.01) |
| A61K 9/08 | (2006.01) |
| A61K 9/20 | (2006.01) |
| A61K 9/28 | (2006.01) |
| A61K 9/48 | (2006.01) |
| A61K 47/12 | (2006.01) |
| A61K 47/34 | (2017.01) |

(52) U.S. Cl.
CPC ............ *C07D 405/14* (2013.01); *A61K 9/08* (2013.01); *A61K 9/2013* (2013.01); *A61K 9/2018* (2013.01); *A61K 9/2027* (2013.01); *A61K 9/2054* (2013.01); *A61K 9/2059* (2013.01); *A61K 9/2813* (2013.01); *A61K 9/2853* (2013.01); *A61K 9/2866* (2013.01); *A61K 9/485* (2013.01); *A61K 9/4858* (2013.01); *A61K 9/4866* (2013.01); *A61K 47/12* (2013.01); *A61K 47/34* (2013.01); *C07D 401/04* (2013.01); *C07B 2200/05* (2013.01)

(58) Field of Classification Search
CPC ................ C07D 403/04; C07D 401/04; A61K 31/497; A61K 31/4427; A61K 31/4439; A61P 9/00; A61P 25/00; A61P 25/28; A61P 29/00
USPC .................... 544/406; 514/255.05, 336, 343; 546/268.1, 276.4
See application file for complete search history.

(56) References Cited

U.S. PATENT DOCUMENTS

| | | |
|---|---|---|
| 9,303,012 B2 | 4/2016 | Bendels et al. |
| 9,321,727 B2 | 4/2016 | Bissantz et al. |
| 9,403,808 B2 | 8/2016 | Bissantz et al. |
| 9,409,866 B2 | 8/2016 | Grether et al. |
| 9,512,141 B2 | 12/2016 | Dhurwasulu et al. |
| 9,522,886 B2 | 12/2016 | Frei et al. |
| 10,308,659 B2 | 6/2019 | Gavelle et al. |
| 2020/0182940 A1 | 6/2020 | Tsai |
| 2020/0239490 A1 | 7/2020 | Frei et al. |
| 2021/0115011 A1 | 4/2021 | Gobbi et al. |
| 2021/0115012 A1 | 4/2021 | Ametamey et al. |
| 2021/0130334 A1 | 5/2021 | Ametamey et al. |

FOREIGN PATENT DOCUMENTS

| | | |
|---|---|---|
| WO | 2012168350 A1 | 12/2012 |
| WO | 2013060751 A1 | 5/2013 |
| WO | 2014086705 A1 | 6/2014 |
| WO | 2014086805 A1 | 6/2014 |
| WO | 2014086806 A1 | 6/2014 |
| WO | 2014086807 A1 | 6/2014 |
| WO | 2014154612 A1 | 10/2014 |
| WO | 2015150438 A1 | 10/2015 |
| WO | 2015150440 A1 | 10/2015 |
| WO | 2017097732 A1 | 6/2017 |
| WO | 2018234284 A1 | 12/2018 |

*Primary Examiner* — Charanjit Aulakh
(74) *Attorney, Agent, or Firm* — Irina E. Britva; Mintz, Levin, Cohn, Ferris, Glovsky and Popeo, P.C.

(57) ABSTRACT

The invention relates to a compound of formula (I)

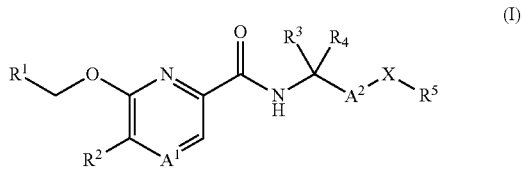

wherein $A^1$, $A^2$ and $R^1$-$R^5$ are as defined in the description and in the claims. The compound of formula (I) can be used as a medicament.

16 Claims, No Drawings

PYRIDINE AND PYRAZINE DERIVATIVES AS PREFERENTIAL CANNABINOID 2 AGONISTS

CROSS-REFERENCE TO RELATED APPLICATIONS

This application is a continuation of International Application No. PCT/EP2019/066733 having an International Filing Date of 25 Jun. 2019, which claims the benefit of priority to European Patent Application No. 18180114.3, filed 27 Jun. 2018, the contents of which applications are hereby incorporated by reference in their entirety.

The present invention relates to organic compounds useful for therapy and/or prophylaxis in a mammal, and in particular to compounds that are preferential agonists of the Cannabinoid Receptor 2.

The invention relates in particular to a compound of formula (I)

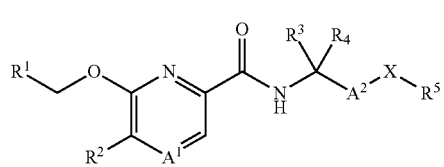

wherein
- $A^1$ is —CH— or nitrogen;
- $A^2$ is —CH$_2$— or carbonyl;
- $R^1$ is haloalkoxyalkylcycloalkyl, haloalkylcycloalkyl, haloalkoxyalkyl, hydroxyalkylcycloalkyl, oxetanyl, haloalkoxyalkyloxetanyl, hydroxyalkyloxetanyl, haloalkyloxetanyl, 1-fluoroethyl, 1-fluoro-prop-2-yl, fluoro-tert.-butyl, cyclopropylfluoromethyl, fluorocyclopropyl, halooxanyl, halotetrahydrofuranyl, phenylalkoxyalkylcycloalkyl, 1-fluoro-1,1-dideuteroprop-2-yl, fluorodideuteromethyl, fluorodideuteromethyloxyalkylcycloalkyl, 2-fluoro-2,2-dideuteroethyloxyalkylcycloalkyl, fluorodideuteromethylcycloalkyl, fluorodideuteromethyloxyalkyl, fluorodideuteromethylalkyl, fluorodideuteromethyloxyalkyloxetanyl, 2-fluoro-2,2-dideuteroethyloxyalkyloxetanyl, 3-fluoro-3,3-dideuteropropyloxyalkyloxetanyl or fluorodideuteromethyloxetanyl;
- $R^2$ is alkoxyazetidinyl, haloazetidinyl, dihaloazetidinyl, pyrrolidinyl or alkylphenylsulfonyloxyazetidinyl;
- $R^3$ and $R^4$ are independently selected from hydrogen, alkyl, alkenyl or deuteroalkyl;
- $R^5$ is hydrogen, alkyl, haloalkyl, deuterioalkyl, alkylphenylsulfonyloxyalkyl, alkylphenylsulfonyloxydeuteroalky or hydroxyalkyl; and
- X is oxygen or —NH—;
or a pharmaceutically acceptable salt thereof.

The compound of formula (I) is particularly useful in the treatment or prophylaxis of e.g. pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis.

The cannabinoid receptors are a class of cell membrane receptors belonging to the G protein-coupled receptor superfamily. There are currently two known subtypes, termed Cannabinoid Receptor 1 (CB1) and Cannabinoid Receptor 2 (CB2). The CB1 receptor is mainly expressed in the central nervous (i.e. amygdala cerebellum, hippocampus) system and to a lesser amount in the periphery. CB2, which is encoded by the CNR2 gene, is mostly expressed peripherally, on cells of the immune system, such as macrophages and T-cells (Ashton, J. C. et al. Curr Neuropharmacol 2007, 5(2), 73-80; Miller, A. M. et al. Br J Pharmacol 2008, 153(2). 299-308; Centonze. D., et al. Curr Pharm Des 2008, 14(23), 2370-42), and in the gastrointestinal system (Wright, K. L. et al. Br J Pharmacol 2008, 153(2), 263-70). The CB2 receptor is also widely distributed in the brain where it is found primarily on microglia and not neurons (Cabral, G. A. et al. Br J Pharmacol 2008, 153(2): 240-51).

The interest in CB2 receptor agonists has been steadily on the rise during the last decade (currently 30-40 patent applications/year) due to the fact that several of the early compounds have been shown to have beneficial effects in pre-clinical models for a number of human diseases including chronic pain (Beltramo, M. Mini Rev Med Chem 2009, 9(1), 11-25), atherosclerosis (Mach, F. et al. J Neuroendocrinol 2008, 20 Suppl 1, 53-7), regulation of bone mass (Bab, I. et al. Br J Pharmacol 2008, 153(2), 182-8), neuroinflammation (Cabral, G. A et al. J Leukoc Biol 2005, 78(6), 1192-7) ischemia/reperfusion injury (Pacher. P. et al. Br J Pharmacol 2008, 153(2), 252-62), systemic fibrosis (Akhmetshina, A. et al. Arthritis Rheum 2009, 60(4), 1129-36; Garcia-Gonzalez, E. et al. Rheumatology (Oxford) 2009, 48(9), 1050-6), liver fibrosis (Julien, B. et al. Gastroenterology 2005, 128(3), 742-55; Munoz-Luque, J. et al. J Pharmacol Exp Ther 2008, 324(2), 475-83).

Ischemia/reperfusion (I/R) injury is the principal cause of tissue damage occurring in conditions such as stroke, myocardial infarction, cardiopulmonary bypass and other vascular surgeries, and organ transplantation, as well as a major mechanism of end-organ damage complicating the course of circulatory shock of various etiologies. All these conditions are characterized by a disruption of normal blood supply resulting in an insufficient tissue oxygenation. Re-oxygenation e.g., reperfusion is the ultimate treatment to restore normal tissue oxygenation. However, the absence of oxygen and nutrients from blood creates a condition in which the restoration of circulation results in further tissue damage. The damage of reperfusion injury is due in part to the inflammatory response of damaged tissues. White blood cells, carried to the area by the newly returning blood, release a host of inflammatory factors such as interleukins as well as free radicals in response to tissue damage. The restored blood flow reintroduces oxygen within cells that damages cellular proteins, DNA, and the plasma membrane.

Remote ischemic preconditioning (RIPC) represents a strategy for harnessing the body's endogenous protective capabilities against the injury incurred by ischemia and reperfusion. It describes the intriguing phenomenon in which transient non-lethal ischemia and reperfusion of one organ or tissue confers resistance to a subsequent episode of "lethal" ischemia reperfusion injury in a remote organ or tissue. The actual mechanism through which transient ischemia and reperfusion of an organ or tissue confers protection is currently unknown although several hypotheses have been proposed.

The humoral hypothesis proposes that the endogenous substance (such as adenosine, bradykinin, opioids, CGRP, endocannabinoids, Angiotensin I or some other as yet unidentified humoral factor) generated in the remote organ or tissue enters the blood stream and activates its respective receptor in the target tissue and thereby recruiting the various intracellular pathways of cardioprotection implicated in ischemic preconditioning.

Recent data indicates that endocannabinnoids and their receptors, in particular CB2 might be involved in preconditioning and contribute to prevent reperfusion injury by downregulation of the inflammatory response (Pacher, P. et al. Br J Pharmacol 2008, 153(2), 252-62). Specifically, recent studies using CB2 tool agonists demonstrated the efficacy of this concept for reducing the I/R injury in the heart (Defer, N. et al. Faseb J 2009, 23(7), 2120-30), the brain (Zhang, M. et al. J Cereb Blood Flow Metab 2007, 27(7), 1387-96), the liver (Batkai, S. et al. Faseb J 2007, 21(8), 1788-800) and the kidney (Feizi, A. et al. Exp Toxicol Pathol 2008, 60(4-5), 405-10).

Moreover, over the last few years, a growing body of literature indicates that CB2 can also be of interest in sub-chronic and chronic setting. Specific upregulation of CB1 and CB2 has been shown to be associated in animal models of chronic diseases associated with fibrosis (Garcia-Gonzalez, E. et al. Rheumatology (Oxford) 2009, 48(9), 1050-6; Yang, Y. Y. et al. Liver Int 2009, 29(5), 678-85) with a relevant expression of CB2 in myofibroblasts, the cells responsible for fibrosis progression.

Activation of CB2 receptor by selective CB2 agonist has in fact been shown to exert anti-fibrotic effect in diffuse systemic sclerosis (Garcia-Gonzalez, E. et al. Rheumatology (Oxford) 2009, 48(9), 1050-6) and CB2 receptor has emerged as a critical target in experimental dermal fibrosis (Akhmetshina, A et al. Arthritis Rheum 2009, 60(4), 1129-36) and in in liver pathophysiology, including fibrogenesis associated with chronic liver diseases (Lotersztajn, S. et al. Gastroenterol Clin Biol 2007, 31(3), 255-8; Mallat, A. et al. Expert Opin Ther Targets 2007, 11(3), 403-9; Lotersztajn, S. et al. Br J Pharmacol 2008, 153(2), 286-9).

The compounds of the invention bind to and modulate the CB2 receptor and have lower CB1 receptor activity.

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain C1-C8 alkyl groups are methyl, ethyl, propyl, isopropyl, butyl, isobutyl, tert.-butyl, the isomeric pentyls, the isomeric hexyls, the isomeric heptyls and the isomeric octyls, particularly methyl, ethyl, propyl, butyl and pentyl. Particular examples of alkyl are methyl, ethyl, isopropyl, butyl, isobutyl, tert.-butyl and pentyl. Methyl, ethyl, propyl and butyl, like isobutyl, are particular examples of "alkyl" in the compound of formula (I).

The term "cycloalkyl", alone or in combination, signifies a cycloalkyl ring with 3 to 8 carbon atoms and particularly a cycloalkyl ring with 3 to 6 carbon atoms. Examples of cycloalkyl are cyclopropyl, cyclobutyl, cyclopentyl and cyclohexyl, cycloheptyl and cyclooctyl. A particular example of "cycloalkyl" is cyclopropyl.

The term "alkoxy" or "alkyloxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy and tert.-butoxy. Particular examples of "alkoxy" are methoxy and ethoxy.

The term "oxy", alone or in combination, signifies the —O— group.

The terms "halogen" or "halo", alone or in combination, signifies fluorine, chlorine, bromine or iodine and particularly fluorine, chlorine or bromine, more particularly fluorine. The term "halo", in combination with another group, denotes the substitution of said group with at least one halogen, particularly substituted with one to five halogens, particularly one to four halogens, i.e. one, two, three or four halogens.

The term "haloalkyl", alone or in combination, denotes an alkyl group substituted with at least one halogen, particularly substituted with one to five halogens, particularly one to three halogens. Particular "haloalkyl" are fluoromethyl, fluoroethyl, fluoropropyl and fluorobutyl.

The term "haloalkoxy" alone or in combination, denotes an alkoxy group substituted with at least one halogen, particularly substituted with one to five halogens, particularly one to three halogens. Particular "haloalkoxy" are fluoromethoxy, fluoroethoxy and fluoropropyloxy.

The terms "hydroxyl" and "hydroxy", alone or in combination, signify the —OH group.

The term "carbonyl", alone or in combination, signifies the —C(O)— group.

The term "amino", alone or in combination, signifies the primary amino group (—NH$_2$), the secondary amino group (—NH—), or the tertiary amino group (—N—).

The term "aminocarbonyl, alone or in combination, signifies the —C(O)—NH$_2$ group.

The term "sulfonyl", alone or in combination, signifies the —SO$_2$— group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, 3$^{rd}$ Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

The invention thus relates to:

A compound according to the invention wherein
R$^1$ is haloalkoxyalklcycloalkyl, haloalkylcycloalkyl, haloalkoxyalkyl, hydroxyalkylcycloalkyl, oxetanyl, haloalkoxyalkyloxetanyl, hydroxyalkyloxetanyl, haloalkyloxetanyl, 1-fluoroethyl, 1-fluoro-prop-2-yl, fluoro-tert.-butyl, cyclopropylfluoromethyl, fluorocyclopropyl, halooxanyl, halotetrahydrofuranyl, 1-fluoro-1,1-dideuteroprop-2-yl, fluorodideuteromethyl, fluorodideuteromethyloxyalkylcycloalkyl, 2-fluoro-2,2-dideuteroethyloxyalkylcycloalkyl, fluorodideuteromethylcycloalkyl, fluorodideuteromethyloxyalkyl, fluorodideuteromethylalkyl, fluorodideuteromethyloxyalkyloxetanyl, 2-fluoro-2,2-dideuteroethyloxyalkyloxetanyl, 3-fluoro-3,3-dideuteropropyloxyalkyloxetanyl or fluorodideuteromethyloxetanyl; and R$^2$ is alkoxyazetidinyl, dihaloazetidinyl or pyrrolidinyl;

A compound according to the invention wherein A$^1$ is —CH—;

A compound according to the invention wherein A$^2$ is carbonyl;

A compound according to the invention wherein R$^1$ is haloalkoxyalkylcycloalkyl, haloalkylcycloalkyl or hydroxyalkylcycloalkyl;

A compound according to the invention wherein R$^1$ is hydroxyalkylcycloalkyl;

A compound according to the invention wherein R$^1$ is fluoromethoxymethylcyclopropyl, fluoromethylcyclopropyl or hydroxmethylcyclopropyl;

A compound according to the invention wherein R$^1$ is hydroxmethylcyclopropyl;

A compound according to the invention wherein R$^2$ is alkoxyazetidinyl or haloazetidinyl;

A compound according to the invention wherein R$^2$ is alkoxyazetidinyl;

A compound according to the invention wherein R$^2$ is methoxyazetidinyl or fluoroazetidinyl;

A compound according to the invention wherein R$^2$ is methoxyazetidinyl;

A compound according to the invention wherein R$^1$ and R$^4$ are both alkyl at the same time or both deuterioalkyl at the same time;

A compound according to the invention wherein R$^1$ and R$^4$ are both alkyl at the same time;

A compound according to the invention wherein R$^3$ and R$^4$ are both ethyl at the same time or both dideuterioethyl at the same time;

A compound according to the invention wherein R$^3$ and R$^4$ are both ethyl at the same time;

A compound according to the invention wherein R$^5$ is alkyl, haloalkyl or halodeuterioalkyl;

A compound according to the invention wherein R$^5$ is haloalkyl or halodeuterioalkyl;

A compound according to the invention wherein R$^5$ is ethyl, fluoromethyl, fluoropropyl, fluorobutyl or fluorohexadeuteriopropyl;

A compound according to the invention wherein R$^5$ is fluoropropyl or fluorohexadeuteriopropyl;

A compound according to the invention wherein X is oxygen;

A compound according to the invention selected from

Ethyl 2-ethyl-2-{[6-({(1S,2S)-2-[(fluoromethoxy)methyl]cyclopropyl}methoxy)-5-(3-methoxyazetidin-1-yl)pyridine-2-carbonyl]amino}butanoate;

Ethyl 2-ethyl-2-{[6-({(1R,2R)-2-[(fluoromethoxy)methyl]cyclopropyl}methoxy)-5-(3-methoxyazetidin-1-yl)pyridine-2-carbonyl]amino}butanoate;

Ethyl 2-ethyl-2-{[6-({(1S,2S)-2-[(2-fluoroethoxy)methyl]cyclopropyl}methoxy)-5-(3-methoxyazetidin-1-yl)pyridine-2-carbonyl]amino}butanoate;

Ethyl 2-ethyl-2-{[6-({(1R,2R)-2-[(2-fluoroethoxy)methyl]cyclopropyl}methoxy)-5-(3-methoxyazetidin-1-yl)pyridine-2-carbonyl]amino}butanoate;

Ethyl 2-ethyl-2-{[6-{[(1S,2S)-2-(fluoromethyl)cyclopropyl]methoxy}-5-(3-methoxyazetidin-1-yl)pyridine-2-carbonyl]amino}butanoate;

Ethyl 2-ethyl-2-{[6-{[(1R,R)-2-(fluoromethyl)cyclopropyl]methoxy}-5-(3-methoxyazetidin-1-yl)pyridine-2-carbonyl]amino}butanoate;

Ethyl 2-ethyl-2-{[6-{[(1R,2S)-2-(fluoromethyl)cyclopropyl]methoxy}-5-(3-methoxyazetidin-1-yl)pyridine-2-carbonyl]amino}butanoate;

Ethyl 2-ethyl-2-{[6-{[(1S,2R)-2-(fluoromethyl)cyclopropyl]methoxy}-5-(3-methoxyazetidin-1-yl)pyridine-2-carbonyl]amino}butanoate;

Ethyl 2-ethyl-2-{[6-({(1R,2S)-2-[(fluoromethoxy)methyl]cyclopropyl}methoxy)-5-(3-methoxyazetidin-1-yl)pyridine-2-carbonyl]amino}butanoate and ethyl 2-ethyl-2-{[6-({(1S,2R)-2-[(fluoromethoxy)methyl]cyclopropyl}methoxy)-5-(3-methoxyazetidin-1-yl)pyridine-2-carbonyl]amino}butanoate;

Ethyl 2-ethyl-2-{[6-({(1R,2S)-2-[(2-fluoroethoxy)methyl]cyclopropyl}methoxy)-5-(3-methoxyazetidin-1-yl)pyridine-2-carbonyl]amino}butanoate;

Ethyl 2-ethyl-2-{[6-({(1S,2R)-2-[(2-fluoroethoxy)methyl]cyclopropyl}methoxy)-5-(3-methoxyazetidin-1-yl)pyridine-2-carbonyl]amino}butanoate;

Ethyl 2-ethyl-2-({6-[3-(fluoromethoxy)-2,2-dimethylpropoxy]-5-(3-methoxyazetidin-1-yl)pyridine-2-carbonyl}amino)butanoate;

(+)-trans-Ethyl 2-ethyl-2-{[6-({-2-[(fluoromethoxy)methyl]cyclopropyl}methoxy)-5-(3-methoxyazetidin-1-yl)pyridine-2-carbonyl]amino}butanoate;

(−)-trans-Ethyl 2-ethyl-2-{[6-({-2-[(fluoromethoxy)methyl]cyclopropyl}methoxy)-5-(3-methoxyazetidin-1-yl)pyridine-2-carbonyl]amino}butanoate;

ethyl 2-ethyl-2-{[6-({(1R,2S)-2-[(fluoromethoxy)methyl]cyclopropyl}methoxy)-5-(3-methoxyazetidin-1-yl)pyridine-2-carbonyl]amino}butanoate ethyl 2-ethyl-2-{[6-({(1S,2R)-2-[(fluoromethoxy)methyl]cyclopropyl}methoxy)-5-(3-methoxyazetidin-1-yl)pyridine-2-carbonyl]amino}butanoate;

(−)-trans-Fluoromethyl 2-ethyl-2-{[6-{[(1R,2R)-2-(hydroxymethyl)cyclopropyl]methoxy}-5-(3-methoxyazetidin-1-yl)pyridine-2-carbonyl]amino}butanoate;

(+)-trans-Fluoromethyl 2-ethyl-2-{[6-{[-2-(hydroxymethyl)cyclopropyl]methoxy}-5-(3-methoxyazetidin-1-yl)pyridine-2-carbonyl]amino}butanoate;

(+)-trans-2-Fluoroethyl 2-ethyl-2-{[6-{[-2-(hydroxymethyl)cyclopropyl]methoxy}-5-(3-methoxyazetidin-1-yl)pyridine-2-carbonyl]amino}butanoate;

(−)-trans-2-Fluoroethyl 2-ethyl-2-{[6-{[-2-(hydroxymethyl)cyclopropyl]methoxy}-5-(3-methoxyazetidin-1-yl)pyridine-2-carbonyl]amino}butanoate;

3-Fluoropropyl 2-ethyl-2-{[6-{[(1S,2S)-2-(hydroxymethyl)cyclopropyl]methoxy}-5-(3-methoxyazetidin-1-yl)pyridine-2-carbonyl]amino}butanoate;

3-Fluoropropyl 2-ethyl-2-{[6-{[(1R,2R)-2-(hydroxymethyl)cyclopropyl]methoxy}-5-(3-methoxyazetidin-1-yl)pyridine-2-carbonyl]amino}butanoate;

N-[(2S)-1-(fluoromethoxy)propan-2-yl]-6-{[(1S,2S)-2-(hydroxymethyl)cyclopropyl]methoxy}-5-(3-methoxyazetidin-1-yl)pyridine-2-carboxamide;

N-[(2S)-1-(2-fluoroethoxy)propan-2-yl]-6-{[(1S,2S)-2-(hydroxymethyl)cyclopropyl]methoxy}-5-(3-methoxyazetidin-1-yl)pyridine-2-carboxamide;

N-[(2S)-1-(3-fluoropropoxy)propan-2-yl]-6-{[(1S,2S)-2-(hydroxymethyl)cyclopropyl]methoxy}-5-(3-methoxyazetidin-1-yl)pyridine-2-carboxamide;

N-[(2S)-1-(fluoromethoxy)-3-methylbutan-2-yl]-6-{[(1S,2S)-2-(hydroxymethyl)cyclopropyl]methoxy}-5-(3-methoxyazetidin-1-yl)pyridine-2-carboxamide;

N-[(2S)-1-(2-fluoroethoxy)-3-methylbutan-2-yl]-6-{[(1S,2S)-2-(hydroxymethyl)cyclopropyl]methoxy}-5-(3-methoxyazetidin-1-yl)pyridine-2-carboxamide;

N-[(2S)-1-(3-fluoropropoxy)-3-methylbutan-2-yl]-6-{[(1S,2S)-2-(hydroxymethyl)cyclopropyl]methoxy}-5-(3-methoxyazetidin-1-yl)pyridine-2-carboxamide;

N-[(2S)-1-(fluoromethoxy)-4-methylpentan-2-yl]-6-{[(1S,2S)-2-(hydroxymethyl)cyclopropyl]methoxy}-5-(3-methoxyazetidin-1-yl)pyridine-2-carboxamide;

N-[(2S)-1-(2-fluoroethoxy)-4-methylpentan-2-yl]-6-{[(1S,2S)-2-(hydroxymethyl)cyclopropyl]methoxy}-5-(3-methoxyazetidin-1-yl)pyridine-2-carboxamide;

N-[(2S)-1-(3-fluoropropoxy)-4-methylpentan-2-yl]-6-{[(1S,2S)-2-(hydroxymethyl)cyclopropyl]methoxy}-5-(3-methoxyazetidin-1-yl)pyridine-2-carboxamide;

N-{3-[(fluoromethoxy)methyl]pentan-3-yl}-6-{[(1S,2S)-2-(hydroxymethyl)cyclopropyl]methoxy}-5-(3-methoxyazetidin-1-yl)pyridine-2-carboxamide;

N-{3-[(2-fluoroethoxy)methyl]pentan-3-yl}-6-{[(1S,2S)-2-(hydroxymethyl)cyclopropyl]methoxy}-5-(3-methoxyazetidin-1-yl)pyridine-2-carboxamide;

N-{3-[(3-fluoropropoxy)methyl]pentan-3-yl}-6-{[(1S,2S)-2-(hydroxymethyl)cyclopropyl]methoxy}-5-(3-methoxyazetidin-1-yl)pyridine-2-carboxamide;

fluoromethyl 2-ethyl-2-{[6-{[(1R,2S)-2-(hydroxymethyl)cyclopropyl]methoxy}-5-(3-methoxyazetidin-1-yl)pyridine-2-carbonyl]amino}butanoate;

2-fluoroethyl 2-ethyl-2-{[6-{[(1R,2S)-2-(hydroxymethyl)cyclopropyl]methoxy}-5-(3-methoxyazetidin-1-yl)pyridine-2-carbonyl]amino}butanoate;

3-fluoropropyl 2-ethyl-2-{[6-{[(1R,2S)-2-(hydroxymethyl)cyclopropyl]methoxy}-5-(3-methoxyazetidin-1-yl)pyridine-2-carbonyl]amino}butanoate;

N-[(2S)-1-(fluoromethoxy)propan-2-yl]-6-{[(1R,2S)-2-(hydroxymethyl)cyclopropyl]methoxy}-5-(3-methoxyazetidin-1-yl)pyridine-2-carboxamide;

N-[(2S)-1-(2-fluoroethoxy)propan-2-yl]-6-{[(1R,2S)-2-(hydroxymethyl)cyclopropyl]methoxy}-5-(3-methoxyazetidin-1-yl)pyridine-2-carboxamide;

N-[(2S)-1-(3-fluoropropoxy)propan-2-yl]-6-{[(1R,2S)-2-(hydroxymethyl)cyclopropyl]methoxy}-5-(3-methoxyazetidin-1-yl)pyridine-2-carboxamide;

N-[(2S)-1-(fluoromethoxy)-3-methylbutan-2-yl]-6-{[(1R,2S)-2-(hydroxymethyl)cyclopropyl]methoxy}-5-(3-methoxyazetidin-1-yl)pyridine-2-carboxamide;

N-[(2S)-1-(2-fluoroethoxy)-3-methylbutan-2-yl]-6-{[(1R,2S)-2-(hydroxymethyl)cyclopropyl]methoxy}-5-(3-methoxyazetidin-1-yl)pyridine-2-carboxamide;

N-[(2S)-1-(3-fluoropropoxy)-3-methylbutan-2-yl]-6-{[(1R,2S)-2-(hydroxymethyl)cyclopropyl]methoxy}-5-(3-methoxyazetidin-1-yl)pyridine-2-carboxamide;

N-[(2S)-1-(fluoromethoxy)-4-methylpentan-2-yl]-6-{[(1R,2S)-2-(hydroxymethyl)cyclopropyl]methoxy}-5-(3-methoxyazetidin-1-yl)pyridine-2-carboxamide;

N-[(2S)-1-(2-fluoroethoxy)-4-methylpentan-2-yl]-6-{[(1R,2S)-2-(hydroxymethyl)cyclopropyl]methoxy}-5-(3-methoxyazetidin-1-yl)pyridine-2-carboxamide;

N-[(2S)-1-(3-fluoropropoxy)-4-methylpentan-2-yl]-6-{[(1R,2S)-2-(hydroxymethyl)cyclopropyl]methoxy}-5-(3-methoxyazetidin-1-yl)pyridine-2-carboxamide;

N-{3-[(fluoromethoxy)methyl]pentan-3-yl}-6-{[(1R,2S)-2-(hydroxymethyl)cyclopropyl]methoxy}-5-(3-methoxyazetidin-1-yl)pyridine-2-carboxamide;

N-{3-[(2-fluoroethoxy)methyl]pentan-3-yl}-6-{[(1R,2S)-2-(hydroxymethyl)cyclopropyl]methoxy}-5-(3-methoxyazetidin-1-yl)pyridine-2-carboxamide;

N-{3-[(3-fluoropropoxy)methyl]pentan-3-yl}-6-{[(1R,2S)-2-(hydroxymethyl)cyclopropyl]methoxy}-5-(3-methoxyazetidin-1-yl)pyridine-2-carboxamide;

fluoromethyl 2-ethyl-2-({5-(3-methoxyazetidin-1-yl)-6-[(oxetan-3-yl)methoxy]pyridine-2-carbonyl}amino)butanoate;

2-fluoroethyl 2-ethyl-2-({5-(3-methoxyazetidin-1-yl)-6-[(oxetan-3-yl)methoxy]pyridine-2-carbonyl}amino)butanoate;

3-fluoropropyl 2-ethyl-2-({5-(3-methoxyazetidin-1-yl)-6-[(oxetan-3-yl)methoxy]pyridine-2-carbonyl}amino)butanoate;

N-[(2S)-1-(fluoromethoxy)propan-2-yl]-5-(3-methoxyazetidin-1-yl)-6-[(oxetan-3-yl)methoxy]pyridine-2-carboxamide;

N-[(2S)-1-(2-fluoroethoxy)propan-2-yl]-5-(3-methoxyazetidin-1-yl)-6-[(oxetan-3-yl)methoxy]pyridine-2-carboxamide;

N-[(2S)-1-(3-fluoropropoxy)propan-2-yl]-5-(3-methoxyazetidin-1-yl)-6-[(oxetan-3-yl)methoxy]pyridine-2-carboxamide;

N-[(2S)-1-(fluoromethoxy)-3-methylbutan-2-yl]-5-(3-methoxyazetidin-1-yl)-6-[(oxetan-3-yl)methoxy]pyridine-2-carboxamide;

N-[(2S)-1-(2-fluoroethoxy)-3-methylbutan-2-yl]-5-(3-methoxyazetidin-1-yl)-6-[(oxetan-3-yl)methoxy]pyridine-2-carboxamide;

N-[(2S)-1-(3-fluoropropoxy)-3-methylbutan-2-yl]-5-(3-methoxyazetidin-1-yl)-6-[(oxetan-3-yl)methoxy]pyridine-2-carboxamide;

N-[(2S)-1-(fluoromethoxy)-4-methylpentan-2-yl]-5-(3-methoxyazetidin-1-yl)-6-[(oxetan-3-yl)methoxy]pyridine-2-carboxamide;

N-[(2S)-1-(2-Fluoroethoxy)-4-methylpentan-2-yl]-5-(3-methoxyazetidin-1-yl)-6-[(oxetan-3-yl)methoxy]pyridine-2-carboxamide;

N-[(2S)-1-(3-fluoropropoxy)-4-methylpentan-2-yl]-5-(3-methoxyazetidin-1-yl)-6-[(oxetan-3-yl)methoxy]pyridine-2-carboxamide;

N-{3-[(fluoromethoxy)methyl]pentan-3-yl}-5-(3-methoxyazetidin-1-yl)-6-[(oxetan-3-yl)methoxy]pyridine-2-carboxamide;

N-{3-[(2-fluoroethoxy)methyl]pentan-3-yl}-5-(3-methoxyazetidin-1-yl)-6-[(oxetan-3-yl)methoxy]pyridine-2-carboxamide;

N-{3-[(3-fluoropropoxy)methyl]pentan-3-yl}-5-(3-methoxyazetidin-1-yl)-6-[(oxetan-3-yl)methoxy]pyridine-2-carboxamide;

N-[(2S)-1-(2-Fluoroethoxy)-4-methylpentan-2-yl]-6-[(oxetan-3-yl)methoxy]-5-(pyrrolidin-1-yl)pyridine-2-carboxamide;

ethyl 2-ethyl-2-{[6-({3-[(fluoromethoxy)methyl]oxetan-3-yl}methoxy)-5-(3-methoxyazetidin-1-yl)pyridine-2-carbonyl]amino}butanoate;

ethyl 2-ethyl-2-{[6-({3-[(2-fluoroethoxy)methyl]oxetan-3-yl}methoxy)-5-(3-methoxyazetidin-1-yl)pyridine-2-carbonyl]amino}butanoate;

ethyl 2-ethyl-2-{[6-({3-[(3-fluoropropoxy)methyl]oxetan-3-yl}methoxy)-5-(3-methoxyazetidin-1-yl)pyridine-2-carbonyl]amino}butanoate;

fluoromethyl 2-ethyl-2-{[6-{[3-(hydroxymethyl)oxetan-3-yl]methoxy}-5-(3-methoxyazetidin-1-yl)pyridine-2-carbonyl]amino}butanoate;

2-fluoroethyl 2-ethyl-2-{[6-{[3-(hydroxymethyl)oxetan-3-yl]methoxy}-5-(3-methoxyazetidin-1-yl)pyridine-2-carbonyl]amino}butanoate;

3-fluoropropyl 2-ethyl-2-{[6-{[3-(hydroxymethyl)oxetan-3-yl]methoxy}-5-(3-methoxyazetidin-1-yl)pyridine-2-carbonyl]amino}butanoate;

N-[(2S)-1-(fluoromethoxy)propan-2-yl]-6-{[3-(hydroxymethyl)oxetan-3-yl]methoxy}-5-(3-methoxyazetidin-1-yl)pyridine-2-carboxamide;

N-[(2S)-1-(2-fluoroethoxy)propan-2-yl]-6-{[3-(hydroxymethyl)oxetan-3-yl]methoxy}-5-(3-methoxyazetidin-1-yl)pyridine-2-carboxamide;

N-[(2S)-1-(3-fluoropropoxy)propan-2-yl]-6-{[3-(hydroxymethyl)oxetan-3-yl]methoxy}-5-(3-methoxyazetidin-1-yl)pyridine-2-carboxamide;

N-[(2S)-1-(fluoromethoxy)-3-methylbutan-2-yl]-6-{[3-(hydroxymethyl)oxetan-3-yl]methoxy}-5-(3-methoxyazetidin-1-yl)pyridine-2-carboxamide;

N-[(2S)-1-(2-fluoroethoxy)-3-methylbutan-2-yl]-6-{[3-(hydroxymethyl)oxetan-3-yl]methoxy}-5-(3-methoxyazetidin-1-yl)pyridine-2-carboxamide;

N-[(2S)-1-(3-fluoropropoxy)-3-methylbutan-2-yl]-6-{[3-(hydroxymethyl)oxetan-3-yl]methoxy}-5-(3-methoxyazetidin-1-yl)pyridine-2-carboxamide;

N-[(2S)-1-(fluoromethoxy)-4-methylpentan-2-yl]-6-{[3-(hydroxymethyl)oxetan-3-yl]methoxy}-5-(3-methoxyazetidin-1-yl)pyridine-2-carboxamide;

N-[(2S)-1-(2-fluoroethoxy)-4-methylpentan-2-yl]-6-{[3-(hydroxymethyl)oxetan-3-yl]methoxy}-5-(3-methoxyazetidin-1-yl)pyridine-2-carboxamide;

N-[(2S)-1-(3-fluoropropoxy)-4-methylpentan-2-yl]-6-{[3-(hydroxymethyl)oxetan-3-yl]methoxy}-5-(3-methoxyazetidin-1-yl)pyridine-2-carboxamide;

N-{3-[(fluoromethoxy)methyl]pentan-3-yl}-6-{[3-(hydroxymethyl)oxetan-3-yl]methoxy}-5-(3-methoxyazetidin-1-yl)pyridine-2-carboxamide;

N-{3-[(2-fluoroethoxy)methyl]pentan-3-yl}-6-{[3-(hydroxymethyl)oxetan-3-yl]methoxy}-5-(3-methoxyazetidin-1-yl)pyridine-2-carboxamide;

N-{3-[(3-fluoropropoxy)methyl]pentan-3-yl}-6-{[3-(hydroxymethyl)oxetan-3-yl]methoxy}-5-(3-methoxyazetidin-1-yl)pyridine-2-carboxamide;

6-({(1S,2S)-2-[(fluoromethoxy)methyl]cyclopropyl}methoxy)-N-[(2S)-1-hydroxy-4-methylpentan-2-yl]-5-(3-methoxyazetidin-1-yl)pyridine-2-carboxamide;

6-({(1S,2S)-2-[(2-fluoroethoxy)methyl]cyclopropyl}methoxy)-N-[(2S)-1-hydroxy-4-methylpentan-2-yl]-5-(3-methoxyazetidin-1-yl)pyridine-2-carboxamide;

6-({(1S,2S)-2-[(3-fluoropropoxy)methyl]cyclopropyl}methoxy)-N-[(2S)-1-hydroxy-4-methylpentan-2-yl]-5-(3-methoxyazetidin-1-yl)pyridine-2-carboxamide;

6-{[(1S,2S)-2-(fluoromethyl)cyclopropyl]methoxy}-N-[(2S)-1-hydroxy-4-methylpentan-2-yl]-5-(3-methoxyazetidin-1-yl)pyridine-2-carboxamide;

6-({(R,2S)-2-[(fluoromethoxy)methyl]cyclopropyl}methoxy)-N-[(2S)-1-hydroxy-3-methylbutan-2-yl]-5-(3-methoxyazetidin-1-yl)pyridine-2-carboxamide;

6-({(1R,2S)-2-[(2-fluoroethoxy)methyl]cyclopropyl}methoxy)-N-[(2S)-1-hydroxy-3-methylbutan-2-yl]-5-(3-methoxyazetidin-1-yl)pyridine-2-carboxamide;

6-({(1R,2S)-2-[(3-fluoropropoxy)methyl]cyclopropyl}methoxy)-N-[(2S)-1-hydroxy-3-methylbutan-2-yl]-5-(3-methoxyazetidin-1-yl)pyridine-2-carboxamide;

6-{[(1R,2S)-2-(fluoromethyl)cyclopropyl]methoxy}-N-[(2S)-1-hydroxy-3-methylbutan-2-yl]-5-(3-methoxyazetidin-1-yl)pyridine-2-carboxamide;

6-({3-[(fluoromethoxy)methyl]oxetan-3-yl}methoxy)-N-[(2S)-1-hydroxypropan-2-yl]-5-(3-methoxyazetidin-1-yl)pyridine-2-carboxamide;

6-({3-[(2-fluoroethoxy)methyl]oxetan-3-yl}methoxy)-N-[(2S)-1-hydroxypropan-2-yl]-5-(3-methoxyazetidin-1-yl)pyridine-2-carboxamide;

6-({3-[(3-fluoropropoxy)methyl]oxetan-3-yl}methoxy)-N-[(2S)-1-hydroxypropan-2-yl]-5-(3-methoxyazetidin-1-yl)pyridine-2-carboxamide;

6-{[3-(fluoromethyl)oxetan-3-yl]methoxy}-N-[(2S)-1-hydroxypropan-2-yl]-5-(3-methoxyazetidin-1-yl)pyridine-2-carboxamide;

6-({3-[(fluoromethoxy)methyl]oxetan-3-yl}methoxy)-N-[3-(hydroxymethyl)pentan-3-yl]-5-(3-methoxyazetidin-1-yl)pyridine-2-carboxamide;

6-({3-[(2-fluoroethoxy)methyl]oxetan-3-yl}methoxy)-N-[3-(hydroxymethyl)pentan-3-yl]-5-(3-methoxyazetidin-1-yl)pyridine-2-carboxamide;

6-({3-[(3-fluoropropoxy)methyl]oxetan-3-yl}methoxy)-N-[3-(hydroxymethyl)pentan-3-yl]-5-(3-methoxyazetidin-1-yl)pyridine-2-carboxamide;

6-{[3-(fluoromethyl)oxetan-3-yl]methoxy}-N-[3-(hydroxymethyl)pentan-3-yl]-5-(3-methoxyazetidin-1-yl)pyridine-2-carboxamide;

ethyl 2-ethyl-2-{[6-({(1S,2S)-2-[(fluoromethoxy)methyl]cyclopropyl}methoxy)-5-(3-methoxyazetidin-1-yl)pyrazine-2-carbonyl]amino}butanoate;

ethyl 2-ethyl-2-{[6-({(1R,2S)-2-[(fluoromethoxy)methyl]cyclopropyl}methoxy)-5-(3-methoxyazetidin-1-yl)pyrazine-2-carbonyl]amino}butanoate;

6-({(1S,2S)-2-[(3-fluoropropoxy)methyl]cyclopropyl}methoxy)-N-[(2S)-1-hydroxy-4-methylpentan-2-yl]-5-(3-methoxyazetidin-1-yl)pyrazine-2-carboxamide;

6-({(1R,2S)-2-[(3-fluoropropoxy)methyl]cyclopropyl}methoxy)-N-[(2S)-1-hydroxy-3-methylbutan-2-yl]-5-(3-methoxyazetidin-1-yl)pyrazine-2-carboxamide;

ethyl 2-ethyl-2-({6-[(3-fluorooxan-4-yl)methoxy]-5-(3-methoxyazetidin-1-yl)pyridine-2-carbonyl}amino)butanoate;

1,4-anhydro-2,3-dideoxy-5-O-[6-{[3-(ethoxycarbonyl)pentan-3-yl]carbamoyl}-3-(3-methoxyazetidin-1-yl)pyridin-2-yl]-2-fluoropentitol;

ethyl 2-ethyl-2-{[6-{[3-fluoro-2-methyl(3,3-dideuterio)propyl]oxy}-5-(3-methoxyazetidin-1-yl)pyridine-2-carbonyl]amino}butanoate;

ethyl 2-ethyl-2-{[6-{[2-fluoro(2,2-dideuterio)ethyl]oxy}-5-(3-methoxyazetidin-1-yl)pyridine-2-carbonyl]amino}butanoate;

ethyl 2-ethyl-2-({6-[(3-fluorooxan-4-yl)methoxy]-5-(3-methoxyazetidin-1-yl)pyridine-2-carbonyl}amino)butanoate;

1,4-anhydro-2,3-dideoxy-5-O-[6-{[3-(ethoxycarbonyl)pentan-3-yl]carbamoyl}-3-(3-methoxyazetidin-1-yl)pyridin-2-yl]-2-fluoropentitol;

ethyl 2-ethyl-2-{[6-{[(1S,2S)-2-({[fluoro(dideuterio)methyl]oxy}methyl)cyclopropyl]methoxy}-5-(3-methoxyazetidin-1-yl)pyridine-2-carbonyl]amino}butanoate;

ethyl 2-ethyl-2-{[6-{[(1S,2S)-2-({[2-fluoro(2,2-~2~H_2_)ethyl]oxy}methyl)cyclopropyl]methoxy}-5-(3-methoxyazetidin-1-yl)pyridine-2-carbonyl]amino}butanoate;

ethyl 2-ethyl-2-{[6-({(1S,2S)-2-[fluoro(dideuterio)methyl]cyclopropyl}methoxy)-5-(3-methoxyazetidin-1-yl)pyridine-2-carbonyl]amino}butanoate;

ethyl 2-ethyl-2-{[6-({(1R,2S)-2-[fluoro(dideuterio)methyl]cyclopropyl}methoxy)-5-(3-methoxyazetidin-1-yl)pyridine-2-carbonyl]amino}butanoate;

ethyl 2-ethyl-2-{[6-{[(1R,2S)-2-({[fluoro(dideuterio)methyl]oxy}methyl)cyclopropyl]methoxy}-5-(3-methoxyazetidin-1-yl)pyridine-2-carbonyl]amino}butanoate;

ethyl 2-ethyl-2-{[6-{[(1R,2S)-2-({[2-fluoro(2,2-dideuterio)ethyl]oxy}methyl)cyclopropyl]methoxy}-5-(3-methoxyazetidin-1-yl)pyridine-2-carbonyl]amino}butanoate;

ethyl 2-ethyl-2-{[6-(3-{[fluoro(dideuterio)methyl]oxy}-2,2-dimethylpropoxy)-5-(3-methoxyazetidin-1-yl)pyridine-2-carbonyl]amino}butanoate;

ethyl 2-ethyl-2-{[6-{[3-fluoro-2,2-dimethyl(3,3-dideuterio)propyl]oxy}-5-(3-methoxyazetidin-1-yl)pyridine-2-carbonyl]amino}butanoate;

ethyl 2-ethyl-2-{[6-{[(1S,2S)-2-({[fluoro(dideuterio)methyl]oxy}methyl)cyclopropyl]methoxy}-5-(3-methoxyazetidin-1-yl)pyridine-2-carbonyl]amino}butanoate;

ethyl 2-ethyl-2-{[6-{[(1R,2R)-2-({[fluoro(dideuterio)methyl]oxy}methyl)cyclopropyl]methoxy}-5-(3-methoxyazetidin-1-yl)pyridine-2-carbonyl]amino}butanoate;

ethyl 2-ethyl-2-{[6-{[3-fluoro-2-methyl(3,3-dideuterio)propyl]oxy}-5-(3-methoxyazetidin-1-yl)pyridine-2-carbonyl]amino}butanoate;

ethyl 2-ethyl-2-{[6-{[2-fluoro(2,2-dideuterio)ethyl]oxy}-5-(3-methoxyazetidin-1-yl)pyridine-2-carbonyl]amino}butanoate;

ethyl 2-ethyl-2-{[6-{[3-fluoro-2-methyl(3,3-dideuterio)propyl]oxy}-5-(3-methoxyazetidin-1-yl)pyridine-2-carbonyl]amino}butanoate;

ethyl 2-ethyl-2-{[6-{[3-fluoro-2-methyl(3,3-dideuterio)propyl]oxy}-5-(3-methoxyazetidin-1-yl)pyridine-2-carbonyl]amino}butanoate;

ethyl 2-ethyl-2-{[6-{[2-fluoro(2,2-dideuterio)ethyl]oxy}-5-(3-methoxyazetidin-1-yl)pyridine-2-carbonyl]amino}butanoate;

ethyl 2-ethyl-2-{[6-{[3-fluoro-2-methyl(3,3-dideuterio)propyl]oxy}-5-(3-methoxyazetidin-1-yl)pyridine-2-carbonyl]amino}butanoate;

6-{[3-({[fluoro(dideuterio)methyl]oxy}methyl)oxetan-3-yl]methoxy}-N-[(2S)-1-hydroxypropan-2-yl]-5-(3-methoxyazetidin-1-yl)pyridine-2-carboxamide;

6-{[3-({[2-fluoro(2,2-dideuterio)ethyl]oxy}methyl)oxetan-3-yl]methoxy}-N-[(2S)-1-hydroxypropan-2-yl]-5-(3-methoxyazetidin-1-yl)pyridine-2-carboxamide;

6-{[3-({[3-fluoro(3,3-dideuterio)propyl]oxy}methyl)oxetan-3-yl]methoxy}-N-[(2S)-1-hydroxypropan-2-yl]-5-(3-methoxyazetidin-1-yl)pyridine-2-carboxamide;

6-({3-[fluoro(dideuterio)methyl]oxetan-3-yl}methoxy)-N-[(2S)-1-hydroxypropan-2-yl]-5-(3-methoxyazetidin-1-yl)pyridine-2-carboxamide;

6-{[3-({[fluoro(dideuterio)methyl]oxy}methyl)oxetan-3-yl]methoxy}-N-[3-(hydroxymethyl)pentan-3-yl]-5-(3-methoxyazetidin-1-yl)pyridine-2-carboxamide;

6-{[3-({[2-fluoro(2,2-dideuterio)ethyl]oxy}methyl)oxetan-3-yl]methoxy}-N-[3-(hydroxymethyl)pentan-3-yl]-5-(3-methoxyazetidin-1-yl)pyridine-2-carboxamide;

6-{[3-({[3-fluoro(3,3-dideuterio)propyl]oxy}methyl)oxetan-3-yl]methoxy}-N-[3-(hydroxymethyl)pentan-3-yl]-5-(3-methoxyazetidin-1-yl)pyridine-2-carboxamide;

6-({3-[fluoro(dideuterio)methyl]oxetan-3-yl}methoxy)-N-[3-(hydroxymethyl)pentan-3-yl]-5-(3-methoxyazetidin-1-yl)pyridine-2-carboxamide;

3-Fluoropropyl-3,4-dideuterio-2-(1,2-dideuterioethyl)-2-[[6-[[(1S,2S)-2-(hydroxymethyl)cyclopropyl]methoxy]-5-(3-methoxyazetidin-1-yl)pyridine-2-carbonyl]amino]butanoate;

Fluoromethyl-2-ethyl-2-(6-((3-(hydroxymethyl)oxetan-3-yl)methoxy)-5-(pyrrolidin-1-yl)picolinamido)butanoate;

2-fluoroethyl-2-ethyl-2-(6-((3-(hydroxymethyl)oxetan-3-yl)methoxy)-5-(pyrrolidin-1-yl)picolinamido)butanoate;

3-fluoropropyl-2-ethyl-2-(6-((3-(hydroxymethyl)oxetan-3-yl)methoxy)-5-(pyrrolidin-1-yl)picolinamido)butanoate;

(1,1,2,2,3,3-Hexadeuterio-3-fluoro-propyl) 2-ethyl-2-[[6-[[(1S,2S)-2-(hydroxymethyl)cyclopropyl]methoxy]-5-(3-methoxyazetidin-1-yl)pyridine-2-carbonyl]amino]butanoate;

3-Fluoropropyl 2-[[6-[[(1S,2S)-2-(hydroxymethyl)cyclopropyl]methoxy]-5-(3-methoxyazetidin-1-yl)pyridine-2-carbonyl]amino]-2-vinyl-but-3-enoate;

3-Fluoropropyl 3,4-dideuterio-2-(1,2-dideuterioethyl)-2-[[6-[[(1S,2S)-2-(hydroxymethyl)cyclopropyl]methoxy]-5-(3-methoxyazetidin-1-yl)pyridine-2-carbonyl]amino]butanoate;

(Rac)-trans-3-Fluoropropyl 2-[[6-[[(1S,2S)-2-(benzyloxymethyl)cyclopropyl]methoxy]-5-(3-hydroxyazetidin-1-yl)pyridine-2-carbonyl]amino]-2-ethyl-butanoate;

3-(p-Tolylsulfonyloxy)propyl 2-ethyl-2-[[6-[[(1S,2S)-2-(hydroxymethyl)cyclopropyl]methoxy]-5-(3-methoxyazetidin-1-yl)pyridine-2-carbonyl]amino]butanoate;

[1,1,2,2,3,3-Hexadeuterio-3-(p-tolylsulfonyloxy)propyl] 2-ethyl-2-[[6-[[(1S,2S)-2-(hydroxymethyl)cyclopropyl]methoxy]-5-(3-methoxyazetidin-1-yl)pyridine-2-carbonyl]amino]butanoate;

4-Fluorobutyl 2-ethyl-2-[[6-[[(1S,2S)-2-(hydroxymethyl)cyclopropyl]methoxy]-5-(3-methoxyazetidin-1-yl)pyridine-2-carbonyl]amino]butanoate;

N-[1-Ethyl-1-[[(1S)-1-(hydroxymethyl)-3-methyl-butyl]carbamoyl]propyl]-6-[[(1S,2S)-2-(hydroxymethyl)cyclopropyl]methoxy]-5-(3-methoxyazetidin-1-yl)pyridine-2-carboxamide;

N-[1-ethyl-1-[[(1S)-1-(hydroxymethyl)-3-methyl-butyl]carbamoyl]propyl]-5-(3-fluoroazetidin-1-yl)-6-[[(1R,2R)-2-(hydroxymethyl)cyclopropyl]methoxy]pyridine-2-carboxamide;

N-[1-Ethyl-1-[[(1S)-1-(hydroxymethyl)-3-methyl-butyl]carbamoyl]propyl]-5-(3-fluoroazetidin-1-yl)-6-[[(1S,2S)-2-(hydroxymethyl)cyclopropyl]methoxy]pyridine-2-carboxamide;

3-Fluoropropyl 2-ethyl-2-{[5-(3-fluoroazetidin-1-yl)-6-{[(1R,2R)-2-(hydroxymethyl)cyclopropyl]methoxy}pyridin-2-yl]formamido}butanoate;

3-Fluoropropyl 2-ethyl-2-{[5-(3-fluoroazetidin-1-yl)-6-{[(1S,2S)-2-(hydroxymethyl)cyclopropyl]methoxy}pyridin-2-yl]formamido}butanoate;

(Rac)-trans-3-fluoropropyl 2-ethyl-2-[[6-[[-2-(hydroxymethyl)cyclopropyl]methoxy]-5-[3-(p-tolylsulfonyloxy)azetidin-1-yl]pyridine-2-carbonyl]amino]butanoate;

3-Fluoropropyl 2-[[6-[[(1S,2S)-2-(benzyloxymethyl)cyclopropyl]methoxy]-5-(3-methoxyazetidin-1-yl)pyridine-2-carbonyl]amino]-2-ethyl-butanoate;

ethyl 2-ethyl-2-{[6-(2-fluoropropoxy)-5-(3-methoxyazetidin-1-yl)pyridine-2-carbonyl]amino}butanoate;

ethyl 2-ethyl-2-{[6-(3-fluoro-2-methylpropoxy)-5-(3-methoxyazetidin-1-yl)pyridine-2-carbonyl]amino}butanoate;

ethyl 2-ethyl-2-{[6-(3-fluoro-2,2-dimethylpropoxy)-5-(3-methoxyazetidin-1-yl)pyridine-2-carbonyl]amino}butanoate;

ethyl 2-ethyl-2-{[6-(3-fluoro-2-methylpropoxy)-5-(3-methoxyazetidin-1-yl)pyridine-2-carbonyl]amino}butanoate;

ethyl 2-ethyl-2-({6-[(1-fluorocyclopropyl)methoxy]-5-(3-methoxyazetidin-1-yl)pyridine-2-carbonyl}amino)butanoate;

ethyl 2-ethyl-2-({6-[(2-fluorocyclopropyl)methoxy]-5-(3-methoxyazetidin-1-yl)pyridine-2-carbonyl}amino)butanoate;

ethyl 2-ethyl-2-{[6-(2-fluoropropoxy)-5-(3-methoxyazetidin-1-yl)pyridine-2-carbonyl]amino}butanoate;

ethyl 2-ethyl-2-{[6-(3-fluoro-2-methylpropoxy)-5-(3-methoxyazetidin-1-yl)pyridine-2-carbonyl]amino}butanoate;

ethyl 2-ethyl-2-{[6-(3-fluoro-2-methylpropoxy)-5-(3-methoxyazetidin-1-yl)pyridine-2-carbonyl]amino}butanoate;

ethyl 2-ethyl-2-({6-[(1-fluorocyclopropyl)methoxy]-5-(3-methoxyazetidin-1-yl)pyridine-2-carbonyl}amino)butanoate; and ethyl 2-ethyl-2-({6-[(2-fluorocyclopropyl)methoxy]-5-(3-methoxyazetidin-1-yl)pyridine-2-carbonyl}amino)butanoate;

or a pharmaceutically acceptable salt thereof.

A compound according to the invention selected from

Ethyl 2-ethyl-2-{[6-({(1S,2S)-2-[(fluoromethoxy)methyl]cyclopropyl}methoxy)-5-(3-methoxyazetidin-1-yl)pyridine-2-carbonyl]amino}butanoate;

Ethyl 2-ethyl-2-{[6-({(1R,2R)-2-[(fluoromethoxy)methyl]cyclopropyl}methoxy)-5-(3-methoxyazetidin-1-yl)pyridine-2-carbonyl]amino}butanoate;

Ethyl 2-ethyl-2-{[6-({(1S,2S)-2-[(2-fluoroethoxy)methyl]cyclopropyl}methoxy)-5-(3-methoxyazetidin-1-yl)pyridine-2-carbonyl]amino}butanoate;

Ethyl 2-ethyl-2-{[6-({(1R,2R)-2-[(2-fluoroethoxy)methyl]cyclopropyl}methoxy)-5-(3-methoxyazetidin-1-yl)pyridine-2-carbonyl]amino}butanoate;

Ethyl 2-ethyl-2-{[6-{[(1R,2S)-2-(fluoromethyl)cyclopropyl]methoxy}-5-(3-methoxyazetidin-1-yl)pyridine-2-carbonyl]amino}butanoate;

Ethyl 2-ethyl-2-{[6-{[(1S,2R)-2-(fluoromethyl)cyclopropyl]methoxy}-5-(3-methoxyazetidin-1-yl)pyridine-2-carbonyl]amino}butanoate;

Ethyl 2-ethyl-2-{[6-({(1R,2S)-2-[(fluoromethoxy)methyl]cyclopropyl}methoxy)-5-(3-methoxyazetidin-1-yl)pyridine-2-carbonyl]amino}butanoate;

Ethyl 2-ethyl-2-{[6-({(1S,2R)-2-[(fluoromethoxy)methyl]cyclopropyl}methoxy)-5-(3-methoxyazetidin-1-yl)pyridine-2-carbonyl]amino}butanoate;

(+)-trans-Ethyl 2-ethyl-2-{[6-({-2-[(fluoromethoxy)methyl]cyclopropyl}methoxy)-5-(3-methoxyazetidin-1-yl)pyridine-2-carbonyl]amino}butanoate;

(+)-trans-Fluoromethyl 2-ethyl-2-{[6-{[-2-(hydroxymethyl)cyclopropyl]methoxy}-5-(3-methoxyazetidin-1-yl)pyridine-2-carbonyl]amino}butanoate;

3-Fluoropropyl 2-ethyl-2-{[6-{[(1S,2S)-2-(hydroxymethyl)cyclopropyl]methoxy}-5-(3-methoxyazetidin-1-yl)pyridine-2-carbonyl]amino}butanoate; and 3-Fluoropropyl 2-ethyl-2-{[6-{[(1R,2R)-2-(hydroxymethyl)cyclopropyl]methoxy}-5-(3-methoxyazetidin-1-yl)pyridine-2-carbonyl]amino}butanoate;

or a pharmaceutically acceptable salt thereof.

The invention further relates in particular to 3-fluoropropyl 2-ethyl-2-{[6-{[(1S,2S)-2-(hydroxymethyl)cyclopropyl]methoxy}-5-(3-methoxyazetidin-1-yl)pyridine-2-carbonyl]amino}butanoate.

The invention also relates in particular to (1,1,2,2,3,3-hexadeuterio-3-fluoro-propyl) 2-ethyl-2-[[6-[[(1S,2S)-2-(hydroxymethyl)cyclopropyl]methoxy]-5-(3-methoxyazetidin-1-yl)pyridine-2-carbonyl]amino]butanoate.

The synthesis of the compound of formula (I) can, for example, be accomplished according to the following schemes.

Following the procedure according to scheme 1, compound AA ($A^1$=CH, R'=H, methyl, ethyl, isopropyl, tert, butyl or another suitable protecting group described for example in T.W. Greene et al., Protective Groups in Organic Chemistry, John Wiley and Sons Inc. New York 1999, 3$^{rd}$ edition) can be used as starting material. AA is either commercially available, described in the literature or can be synthesized by a person skilled in the art.

Scheme 1

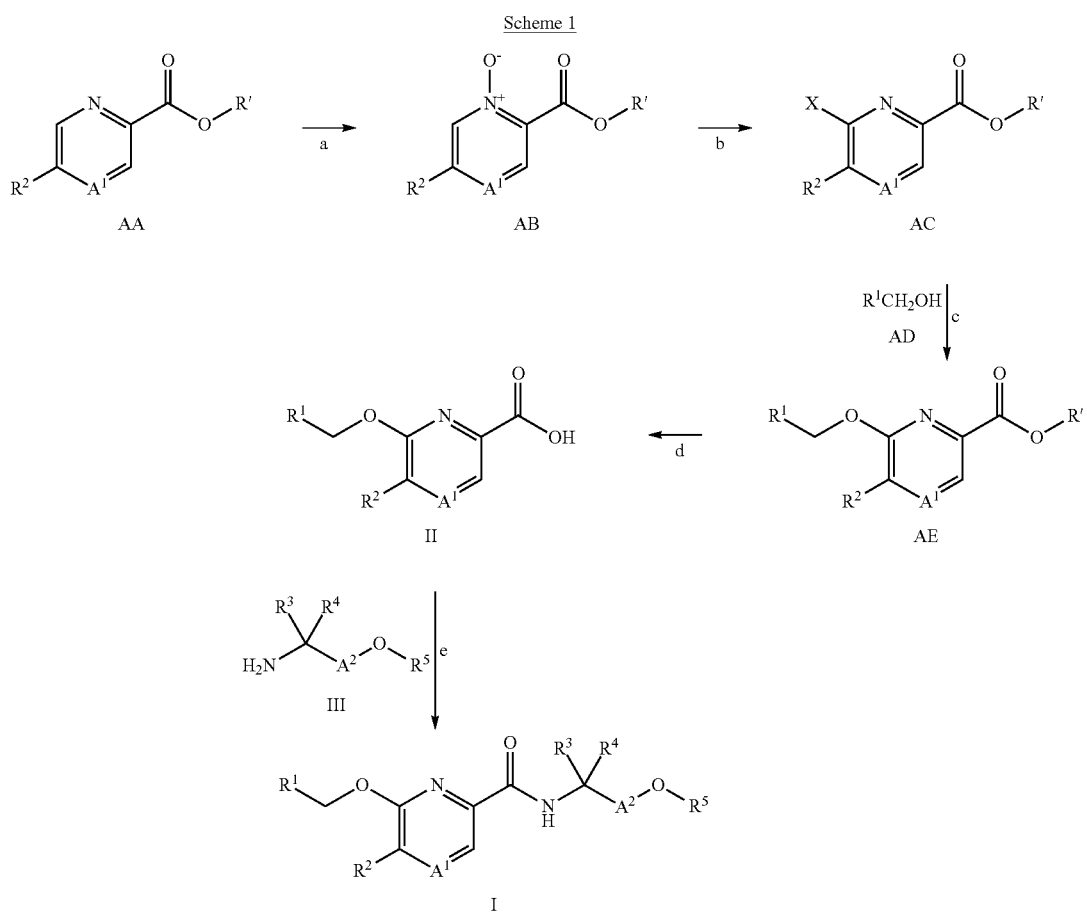

Compound AB can be prepared from AA by oxidation with a suitable oxidizing reagent under conditions known to a person skilled in the art (step a), e.g. by treatment with 3-chloro perbenzoic acid in dichloromethane at ambient temperature.

Conversion of compound AB to 6-chloro or 6-bromo-picoline AC (X=Cl, Br) can be achieved e.g. by treatment with phosphoryl trichloride or tribromide either without an additional solvent or in a suitable solvent such as chloroform at temperatures between 20° C. and the boiling point of the solvent, or by using other conditions known in the literature (step b).

6-Chloro- or bromo-picoline AC (X=Cl, Br) can be transformed to compound AE by reaction with a suitably substituted primary or secondary alcohol AD such as cyclopropylmethanol in the presence of a base, for example sodium hydride, with or without an inert solvent, for example dimethylformamide, at temperatures ranging from room temperature to the reflux temperature of the solvent, particularly at room temperature (step c).

The saponification of the ester of general formula AE (R'≠H) by methods well known to the ones skilled in the art—using e.g. aqueous LiOH, NaOH or KOH in tetrahydrofuran/ethanol or another suitable solvent at temperatures between 0° C. and the reflux temperature of the solvent employed—leads to an acid of general formula II (step d).

Compound I can be prepared from II and the corresponding amine of formula III by suitable amide bond forming reactions (step e). These reactions are known in the art. For example coupling reagents like N,N'-carbonyl-diimidazole (CDI), N,N'-dicyclohexylcarbodiimide (DCC). 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU), and O-benzotriazole-N,N,N',N'-tetramethyl-uronium-hexafluoro-phosphate (HBTU) can be employed to affect such transformation. A convenient method is to use for example HBTU and a base, for example N-methylmorpholine in an inert solvent such as for example dimethylformamide at room temperature.

Alternatively, compound AC (R'=methyl, ethyl, isopropyl, tert, butyl or another suitable protecting group described for example in T.W. Greene et al., Protective Groups in Organic Chemistry, John Wiley and Sons Inc. New York 1999, 3$^{rd}$ edition) can be: i) converted into its acid congener AC (R'=H) as described in step d; ii) transformed into the corresponding amide by treatment with amine III as described in step e; and iii) reacted with alcohol AD as described in step c to arrive at compound I.

Amines III and alcohols AD are either commercially available, described in the literature, can be synthesized by a person skilled in the art or as described in the experimental part.

If one of the starting materials, compounds of formulae AA, AD or III, contains one or more functional groups which are not stable or are reactive under the reaction conditions of one or more reaction steps, appropriate protecting groups (P) (as described e.g. in T.W. Greene et al., Protective Groups in Organic Chemistry, John Wiley and Sons Inc. New York 1999, $3^{rd}$ edition) can be introduced before the critical step applying methods well known in the art. Such protecting groups can be removed at a later stage of the synthesis using standard methods known in the art.

If one or more compounds of formulae AA to AE, AD, II or II contain chiral centers, picolines of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

Following the procedure according to scheme 2, compound BA ($A^1$=CH, R'=H, methyl, ethyl, isopropyl, tert. butyl or another suitable protecting group described for example in T.W. Greene et al., Protective Groups in Organic Chemistry, John Wiley and Sons Inc. New York 1999, $3^{rd}$ edition) can be used as starting material. BA is either commercially available (e.g. for R'=methyl: 5-bromo-6-chloro-pyridine-2-carboxylic acid methyl ester CAN 1214353-79-3), described in the literature or can be synthesized by a person skilled in the art.

described in step c of scheme 1; ii) saponification as described in step d of scheme 1; and iii) amide bond formation as described in step e of scheme 1.

Furthermore, compound BA can be converted into compound BC by treatment with compound AD as described in step c of scheme 1 (step b).

Subsequent transformation of compound BC into compound AE can be achieved as discussed for the conversion of BA into AC' (step a).

Compound AE can be further elaborated to compound I by: i) saponification as described in step d of scheme 1; ii) amide bond formation as described in step e of scheme 1.

Alternatively, compound BC (R'=methyl, ethyl, isopropyl, tert. butyl or another suitable protecting group described for example in T.W. Greene et al., Protective Groups in Organic Chemistry, John Wiley and Sons Inc. New York 1999, $3^{rd}$ edition) can be: i) converted into its acid congener BC (R'=H) as described in step d of scheme 1; ii) transformed into the corresponding amide BD by treatment with amine II as described in step e of scheme 1; and iii) reacted with BB as described in step a to arrive at compound I.

Furthermore, compound I can also be synthesized applying the following reaction sequence: i) saponification of compound BA (R'=methyl, ethyl, isopropyl, tert, butyl or another suitable protecting group described for example in T.W. Greene et al., Protective Groups in Organic Chemistry,

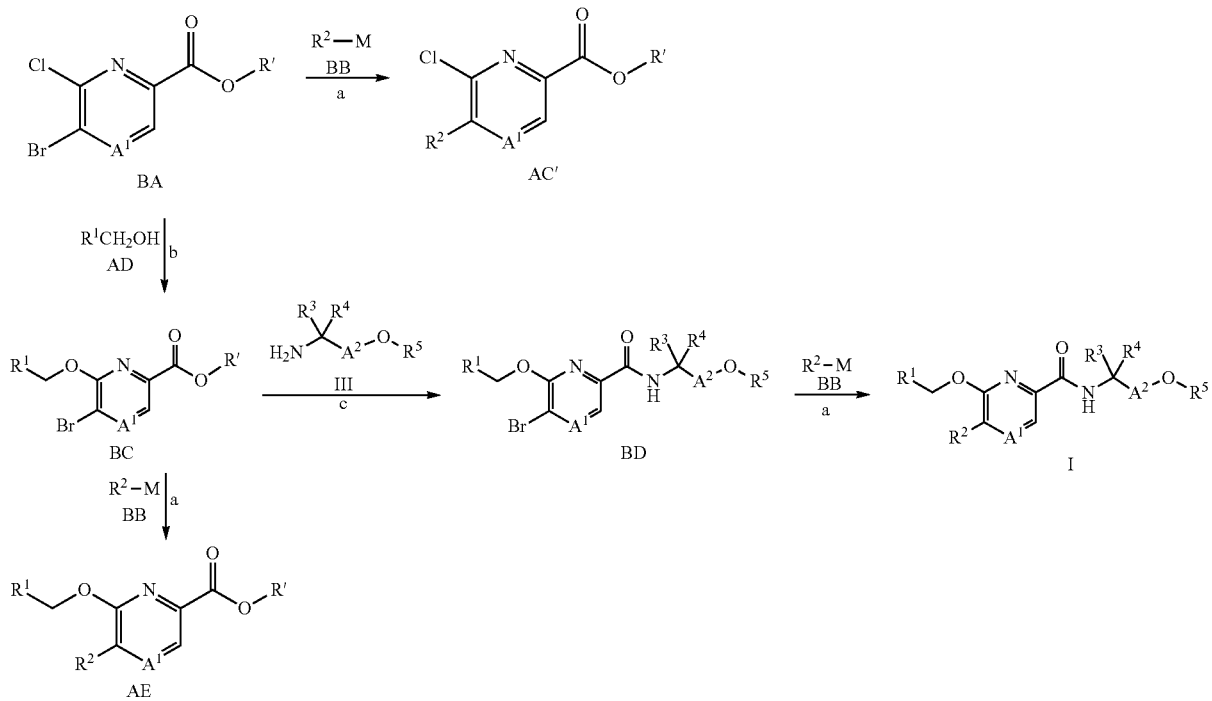

Scheme 2

Compound AC' can be prepared from BA by coupling with an amine BB (M is H) by methods well known to a person skilled in the art, e.g. using a palladium catalyst such as tris(dibenzylideneacetone)dipalladium/dimethylbisdiphenyl-phosphinoxanthene and a base such as cesium carbonate in a solvent such as 1,4-dioxane, preferentially at the boiling point of the solvent (step a).

Compound AC' can be further elaborated to compound I by: i) reaction with compound AD to form compound AE as John Wiley and Sons Inc. New York 1999, $3^{rd}$ edition) to its acid congener BA (R'=H) as described in step d of scheme 1; ii) conversion to the corresponding amide by treatment with amine III as described in step e of scheme 1; iii) reaction with compound BB as described in step a; and iv) reaction with compound AD as described in step b. Optionally step iii) and step iv) can be interchanged.

If one of the starting materials, compounds of formulae BA, BB, AD or II contains one or more functional groups which are not stable or are reactive under the reaction conditions of one or more reaction steps, appropriate protecting groups (P) (as described e.g. in T.W. Greene et al., Protective Groups in Organic Chemistry. John Wiley and Sons Inc. New York 1999, $3^{rd}$ edition) can be introduced before the critical step applying methods well known in the art. Such protecting groups can be removed at a later stage of the synthesis using standard methods known in the art.

If one or more compounds of formulae BA, BB, AD or II contain chiral centers, picolines of formula AC', AE, BC, BD and I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

Following the procedure according to scheme 3, compound CA (R'=H, methyl, ethyl, isopropyl, tert, butyl or another suitable protecting group described for example in T.W. Greene et al., Protective Groups in Organic Chemistry, John Wiley and Sons Inc. New York 1999, $3^{rd}$ edition) can be used as starting material. CA is either commercially available (e.g. for R'=methyl: 5-chloro-pyrazine-2-carboxylic acid methyl ester, CAN 33332-25-1), described in the literature or can be synthesized by a person skilled in the art.

Bromo-pyrazine CD can be transformed to compound CE by reaction with a suitably substituted primary or secondary alcohol AD such as substituted cyclopropylmethanol in the presence of a base, for example potassium hydroxide, with or without an inert solvent, for example DMSO, at temperatures ranging from room temperature to the reflux temperature of the solvent, particularly at room temperature (step d).

Compound I can be prepared from acid CE and the corresponding amine of formula III by suitable amide bond forming reactions (step e). These reactions are known in the art. For example coupling reagents like N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-JH-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU), and O-benzotriazole-N,N,N',N'-tetramethyl-uronium-hexafluoro-phosphate (HBTU) can be employed to affect such transformation. A convenient method is to use for example HBTU and a base, for example N-methylmorpholine in an inert solvent such as for example dimethylformamide at room temperature.

Amines III and alcohols AD are either commercially available, described in the literature, can be synthesized by a person skilled in the art or as described in the experimental part.

Scheme 3

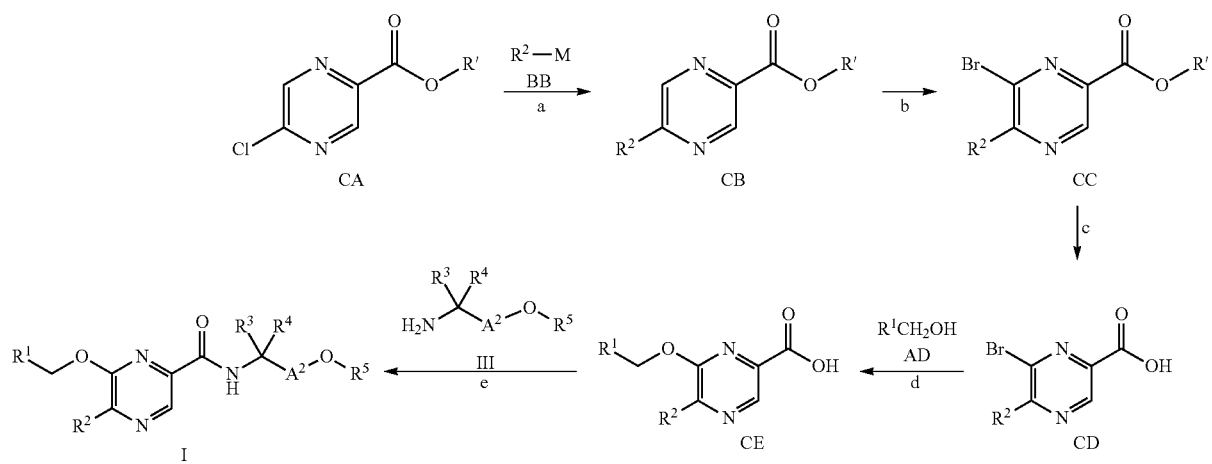

Compound CB can be prepared from CA by coupling with an amine BB (M is H) by methods well known to a person skilled in the art, e.g. by reacting with the corresponding amine BB (M is H) in the presence of a base, particularly triethylamine, in an inert solvent, particularly dioxane at temperatures ranging from room temperature to 45° C. (step a).

Conversion of compound CB to CC can be achieved by electrophilic aromatic bromination in a suitable solvent, particularly by bromination with N-bromosuccinimide in chloroform at elevated temperature, particularly at 60° C., or by using other conditions known in the literature (step b).

The saponification of the ester of general formula CC by methods well known to the ones skilled in the art—using e.g. aqueous LiOH, NaOH or KOH in tetrahydrofuran/ethanol or another suitable solvent at temperatures between 0° C. and the reflux temperature of the solvent employed—leads to the acid of general formula CD (step c).

If one of the starting materials, compounds of formulae CA, BB, AD or III contains one or more functional groups which are not stable or are reactive under the reaction conditions of one or more reaction steps, appropriate protecting groups (P) (as described e.g. in T.W. Greene et al., Protective Groups in Organic Chemistry, John Wiley and Sons Inc. New York 1999, $3^{rd}$ edition) can be introduced before the critical step applying methods well known in the art. Such protecting groups can be removed at a later stage of the synthesis using standard methods known in the art.

If one or more compounds of formulae CA, BB, AD or III contain chiral centers, pyrazines of formula CB to CE or I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

The invention thus also relates to a process for the preparation of a compound according to the invention comprising one of the following steps:
(a) the reaction of a compound of formula (A1)

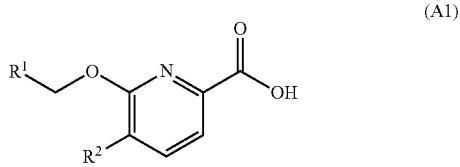

(A1)

with a compound of formula (A2)

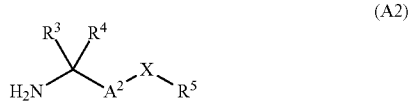

(A2)

in the presence of a coupling agent and a base;
(b) the reaction of a compound of formula (B)

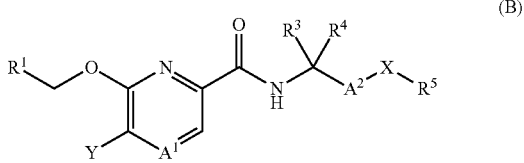

(B)

in the presence of $R^2M$, a palladium catalyst and a base; wherein $A^1$, $A^2$, $R^1$-$R^5$ and X are as defined above and Y is halogen.

The coupling agent of step (a) is conveniently an amide bond forming agent, like e.g. N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU) or and O-benzotriazole-N,N,N'N'-tetramethyl-uronium-hexafluoro-phosphate (HBTU).

N-methylmorpholine is a convenient base for step (a).

HBTU can advantageously be used in combination with N-methylmorpholine in step (a).

The solvent of step (a) can advantageously be dimethylformamide.

In step (b), the palladium catalyst can be for example tris(dibenzylideneacetone)dipalladium/dimethylbisdiphenyl-phosphinoxanthene.

In step (b) the base can be e.g. cesium carbonate.
In step (b), the solvent is advantageously 1,4-dioxane.
Y can conveniently be bromine.

The invention also relates to a compound according to the invention when manufactured according to a process of the invention.

Another embodiment of the invention provides a pharmaceutical composition or medicament containing a compound of the invention and a therapeutically inert carrier, diluent or excipient, as well as a method of using the compounds of the invention to prepare such composition and medicament. In one example, the compound of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compound of formula (I) is sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro. Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The invention also relates in particular to:
The use of a compound of formula (I) for the treatment or prophylaxis of pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis;

The use of a compound according of formula (I) for the preparation of a medicament for the treatment or prophylaxis of pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis; A compound of formula (I) for use in the treatment or prophylaxis of pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis; and A method for the treatment or prophylaxis of pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis, which method comprises administering an effective amount of a compound of formula (I) to a patient in need thereof.

The invention particularly relates to a compound of formula (I) for the treatment or prophylaxis of ischemia, reperfusion injury, liver fibrosis or kidney fibrosis, in particular ischemia or reperfusion injury.

The invention will now be illustrated by the following examples which have no limiting character.

EXAMPLES

Abbreviations

AcOH=acetic acid; rac-BINAP=racemic 2,2'-bis(diphenylphosphino)-1,1'-binaphthyl); CAN=chemical abstracts service number; DCM=dichloromethane; DEA=diethanolamine; DIPEA=N-ethyl-N-isopropylpropan-2-amine; DMF=dimethylformamide; DPPA=diphenylphosphoryl azide; EDC=1-ethyl-3-(3-dimethylaminopropyl)carbodiimide; EI=electron impact; EtOAc=ethyl acetate; HATU=2-(3H-[1,2,3]triazolo[4,5-b]pyridin-3-yl)-1,1,3,3-tetramethylisouronium hexafluoro-phosphate(V); HBTU=O-benzotriazole-N,N,N',N'-tetramethyl-uronium-hexafluoro-phosphate; HOBt=hydroxybenzotriazole; HPLC=LC=high performance liquid chromatography; ISP=ion spray, corresponds to ESI (electrospray); LAH=Lithiumaluminiumhydrid; LC=liquid chromatography; LiTMP=lithium tetramethylpiperidide; MS=mass spectrometry; NMR data are reported in parts per million (S) relative to internal tetramethylsilane and are referenced to the deuterium lock signal from the sample solvent ($d_6$-DMSO unless otherwise stated); coupling constants (J) are in Hertz; m-CPBA=meta-chloroperoxybenzoic acid; mp=melting point; PTSA=p-toluenesulfonic acid; RT=room temperature; Rt=retention time; SFC=supercritical fluid chromatography; SOR=specific optical rotation; TBAF=tetra-n-butylammonium fluoride; TBTU=O-(benzotriazol-1-yl)-N,N,N',N'-tetramethyl-uronium-tetrafluoroborate; THF=tetrahydrofuran.

Example 1

Ethyl 2-ethyl-2-{[6-({(1S,2S)-2-[(fluoromethoxy)methyl]cyclopropyl}methoxy)-5-(3-methoxyazetidin-1-yl)pyridine-2-carbonyl]amino}butanoate and ethyl 2-ethyl-2-{[6-({(1R,2R)-2-[(fluoromethoxy)methyl]cyclopropyl}methoxy)-5-(3-methoxyazetidin-1-yl)pyridine-2-carbonyl]amino}butanoate

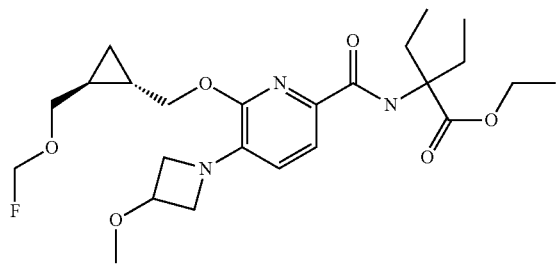

a) (Rac)-trans-5-bromo-6-((-2-(((tert-butyldimethylsilyl)oxy)methyl)cyclopropyl)methoxy)picolinic Acid

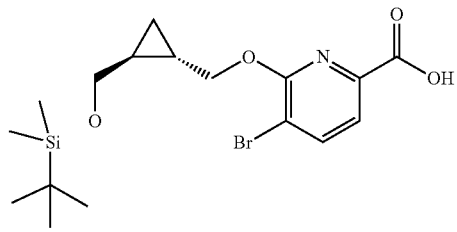

In a 250 mL round-bottomed flask, sodium hydride in mineral oil (507 mg, 12.7 mmol, Eq: 2) was combined with DMF (50 mL) to give a grey suspension, which was cooled to 0° C. (Rac)-trans-(-2-(((tert-butyldimethylsilyl)oxy)methyl)cyclopropyl)methanol (2.06 g, 9.52 mmol, Eq: 1.5) was dissolved in DMF (100 mL) and added to the reaction mixture, which was stirred at 0° C. for 1 h. 5-Bromo-6-chloropicolinic acid (CAN 959958-25-9, 1500 mg, 6.34 mmol, Eq: 1) was dissolved in DMF (20 mL) and added to the reaction mixture. Stirring was continued at RT for 20 h. 250 mg of sodium hydride was added and stirring was continued for 3 h. Another portion of 450 mg NaH and 300 mg of (rac)-trans-(-2-(((tert-butyldimethylsilyl)oxy)methyl)cyclopropyl)methanol were added. After 3 h of stirring at RT the reaction mixture was quenched by the addition of water and concentrated in vacuo. The residue was carefully acidified by the addition of HCl (1 M). The mixture was diluted with EtOAc and washed with brine (3×250 mL). The organic layers were dried over $Na_2SO_4$ and concentrated in vacuo resulting in a colorless oil. The crude product was purified by column chromatography ($SiO_2$, 50 g, hept./EtOAc) to give enriched title compound (1 g) which was sufficiently pure to be carried on to the next step, MS (ISP): 416.3 $[MH^+]$.

b) (Rac)-trans-ethyl 2-(5-bromo-6-((-2-(((tert-butyldimethylsilyl)oxy)methyl)cyclopropyl)methoxy)picolinamido)-2-ethylbutanoate

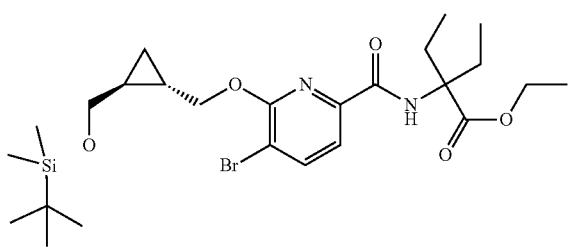

In a 50 mL round-bottomed flask, (rac)-trans-5-bromo-6-((-2-(((tert-butyldimethylsilyl)oxy)methyl)cyclopropyl)methoxy)picolinic acid (1.02 g, 2.45 mmol, Eq: 1.5) was combined with DMF (28.2 mL) to give a colorless solution. DIPEA (1.06 g, 1.43 mL, 8.18 mmol, Eq: 5) and TBTU (788 mg, 2.45 mmol, Eq: 1.5) were added. Ethyl 2-amino-2-ethylbutanoate hydrochloride (CAN 1135219-29-2, 320 mg, 1.64 mmol, Eq: 1) was added and the reaction mixture was stirred at RT for 1 h. The solvent was removed under reduced pressure and the residue dissolved in EtOAc. The organic layers were combined, washed with sat. $NaHCO_3$ (3×20 mL), 1 M HCl (3×20 mL), and sat. NaCl (3×20 mL). The organic layers were dried over $Na_2SO_4$ and concentrated in vacuo. The crude product was purified by column chromatography ($SiO_2$, 50 g, hept./EtOAc) to give the title compound (235 mg, 26%) as colorless oil, MS (ISP): 556.8 $[M–H^-]$.

c) (Rac)-trans-ethyl 2-(6-((-2-(((tert-butyldimethylsilyl)oxy)methyl)cyclopropyl)methoxy)-5-(3-methoxyazetidin-1-yl)picolinamido)-2-ethylbutanoate

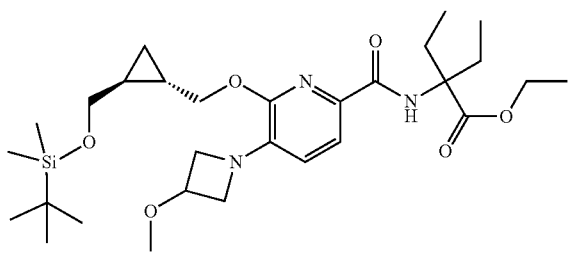 [SMILES: CCOC(=O)C(CC)(CC)NC(=O)c1ccc(N2CC(OC)C2)c(OC[C@H]2C[C@@H]2CO[Si](C)(C)C(C)(C)C)n1]

In a 20 mL sealed tube (rac)-trans-ethyl 2-(5-bromo-6-((-2-(((tert-butyldimethylsilyl)oxy)methyl)cyclopropyl)methoxy)picolinamido)-2-ethylbutanoate (228 mg, 409 µmol, Eq: 1) was combined with toluene (15 mL) to give a colorless solution. $Cs_2CO_3$ (400 mg, 1.23 mmol, Eq: 3) and 3-methoxyazetidine hydrochloride (CAN 148644-09-1, 75.5 mg, 613 µmol, Eq: 1.5) were added, rac-2,2'-Bis(diphenylphosphino)-1,1'-binaphthyl(50.9 mg, 81.8 µmol, Eq: 0.2) and palladium(II) acetate (18.4 mg, 81.8 µmol, Eq: 0.2) were added. The reaction mixture was stirred at 110° C. for 4 h, diluted with EtOAc and filtered through celite. The organic solvent was removed under reduced pressure and the residue dissolved in EtOAc. The organic layers were combined, washed with 1 M HCl (3×25 mL) and sat. NaCl (1×25 mL). The organic layers were dried over $Na_2SO_4$ and concentrated in vacuo. The crude product was purified by column chromatography ($SiO_2$, 20 g, hept./EtOAc) to give the title compound (207 mg, 90%) as colorless oil.

d) (Rac)-trans-ethyl 2-ethyl-2-(6-((-2-(hydroxymethyl)cyclopropyl)methoxy)-5-(3-methoxyazetidin-1-yl)picolinamido)butanoate

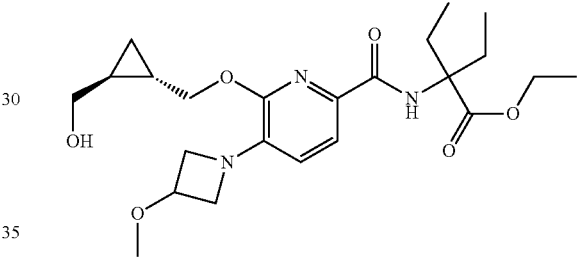

In a 50 mL round-bottomed flask, (rac)-trans-ethyl 2-(6-((-2-(((tert-butyldimethylsilyl)oxy)methyl)cyclopropyl)methoxy)-5-(3-methoxyazetidin-1-yl)picolinamido)-2-ethylbutanoate (200 mg, 355 µmol, Eq: 1) was combined with AcOH (3 mL), water (1 mL) and THF (1 mL) to give a colorless solution. The reaction mixture was stirred at RT for 1 h. The organic solvent was removed under reduced pressure and the residue diluted with EtOAc. The organic layers were combined, washed with sat. $NaHCO_3$ (3×10 mL) and sat. NaCl (1×25 mL). The organic layers were dried over $Na_2SO_4$ and concentrated in vacuo to give the title compound (186 mg, quant.) as coloreless oil which was used in the next step without further purification, MS (ISP): 450.343 $[MH^+]$.

e) Ethyl 2-ethyl-2-{[6-({(1S,2S)-2-[(fluoromethoxy)methyl]cyclopropyl}methoxy)-5-(3-methoxyazetidin-1-yl)pyridine-2-carbonyl]amino}butanoate and ethyl 2-ethyl-2-{[6-({(1R,2R)-2-[(fluoromethoxy)methyl]cyclopropyl}methoxy)-5-(3-methoxyazetidin-1-yl)pyridine-2-carbonyl]amino}butanoate In a 5 mL round-bottomed flask, (rac)-trans-ethyl 2-ethyl-2-(6-((-2-(hydroxymethyl)cyclopropyl)methoxy)-5-(3-methoxyazetidin-1-yl)picolinamido)butanoate (31 mg, 69 µmol, Eq: 1) was combined with DMF (1 mL) to give a light yellow solution. Sodium hydride on mineral oil (13.8 mg, 345 µmol, Eq: 5) was added and the reaction mixture was stirred for 30 min at RT. Fluoro-iodo-methane (55.1 mg, 23.3 µL, 345 µmol, Eq: 5) was added. The reaction mixture was stirred for 12 h at RT, diluted with EtOAc and washed with brine (3×10 mL). The organic layers were dried over Na$_2$SO$_4$ and concentrated in vacuo to give the title compounds (2.5 mg, 5.19 µmol, 8%) as colorless oil, MS (ISP): 482.370 [MH$^+$].

Example 2

Ethyl 2-ethyl-2-{[6-({(1S,2S)-2-[(2-fluoroethoxy) methyl]cyclopropyl}methoxy)-5-(3-methoxyazetidin-1-yl)pyridine-2-carbonyl]amino}butanoate and ethyl 2-ethyl-2-{[6-({(1R,2R)-2-[(2-fluoroethoxy) methyl]cyclopropyl}methoxy)-5-(3-methoxyazetidin-1-yl)pyridine-2-carbonyl]amino}butanoate

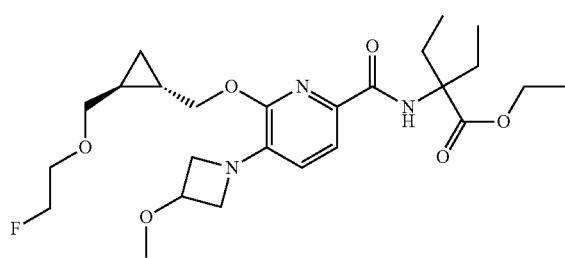 [SMILES: CCOC(=O)C(CC)(CC)NC(=O)c1ccc(N2CC(OC)C2)c(OC[C@H]2C[C@@H]2COCCF)n1]

In analogy to the procedure described in example 1 e, (rac)-trans-ethyl 2-ethyl-2-(6-((-2-(hydroxymethyl)cyclopropyl)methoxy)-5-(3-methoxyazetidin-1-yl)picolinamido) butanoate (example 1 d) was reacted with fluoro-iodo-ethane to give the title compounds as colorless oil, MS (ISP): 492.359 [MH$^+$].

Example 3

Ethyl 2-ethyl-2-{[6-{[(1S,2S)-2-(fluoromethyl)cyclopropyl]methoxy}-5-(3-methoxyazetidin-1-yl) pyridine-2-carbonyl]amino}butanoate and ethyl 2-ethyl-2-{[6-{[(1R,R)-2-(fluoromethyl)cyclopropyl]methoxy}-5-(3-methoxyazetidin-1-yl)pyridine-2-carbonyl]amino}butanoate

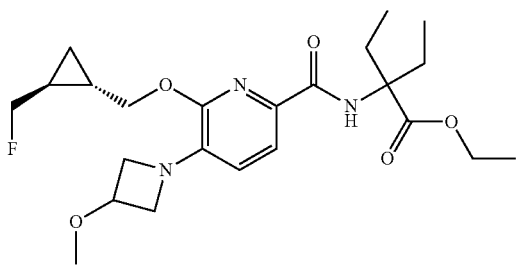 [SMILES: CCOC(=O)C(CC)(CC)NC(=O)c1ccc(N2CC(OC)C2)c(OC[C@H]2C[C@@H]2CF)n1]

a) (Rac)-trans-ethyl 2-ethyl-2-(5-(3-methoxyazetidin-1-yl)-6-((-2-(((methylsulfonyl)oxy)methyl)cyclopropyl)methoxy)picolinamido)butanoate

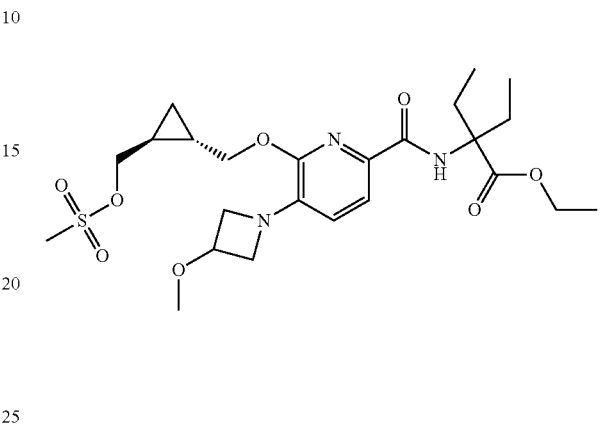

In a 5 mL round-bottomed flask, (rac)-trans-ethyl 2-ethyl-2-(6-((-2-(hydroxymethyl)cyclopropyl)methoxy)-5-(3-methoxyazetidin-1-yl)picolinamido)butanoate (example 1 d, 50 mg, 111 µmol, Eq: 1) was combined with CH$_2$Cl$_2$ (1000 µL) to give a colorless solution. The reaction mixture was cooled to 0° C. and triethylamine (33.8 mg, 46.5 µL, 334 µmol, Eq: 3) and methanesulfonyl chloride (25.5 mg, 17.3 µL, 222 µmol, Eq: 2) were added. The reaction mixture was stirred at RT for 2 h. Additional 10 uL of methanesulfonyl chloride were added and stirring was continued for 30 min. The reaction mixture was diluted with EtOAc and the organic layers were washed with 1 M HCl (3×10 mL), sat NaHCO$_3$(3×10 mL), and sat NaCl (1×20 mL). The organic layers were dried over Na$_2$SO$_4$ and concentrated in vacuo to give crude title compound which was used in the next step without further purification, LC-MS: 528.3 [MH$^+$].

b) Ethyl 2-ethyl-2-{[6-{[(1S,2S)-2-(fluoromethyl) cyclopropyl]methoxy}-5-(3-methoxyazetidin-1-yl) pyridine-2-carbonyl]amino}butanoate and ethyl 2-ethyl-2-{[6-{[(1R,R)-2-(fluoromethyl)cyclopropyl]methoxy}-5-(3-methoxyazetidin-1-yl)pyridine-2-carbonyl]amino}butanoate In a 20 mL sealed tube (rac)-trans-ethyl 2-ethyl-2-(5-(3-methoxyazetidin-1-yl)-6-((-2-(((methylsulfonyl)oxy) methyl)cyclopropyl)methoxy)picolinamido)butanoate (64 mg, 121 µmol, Eq: 1) was combined with acetonitrile (10 mL) under an atmosphere of argon to give a colorless solution. TBAF in THF (606 µL, 606 µmol, Eq: 5) was added and the reaction mixture was heated to 80° C. for 1 h. The mixture was diluted with EtOAc and washed with 1 M HCl (3×25 mL) and brine (1×25 mL). The crude product was purified by column chromatography (SiO$_2$, 5 g, hept./ EtOAc) to give the title compounds (19 mg, 35%) as colorless oil, MS (ISP): 452.351 [MH$^+$].

Example 4

Ethyl 2-ethyl-2-{[6-{[(1R,2S)-2-(fluoromethyl)cyclopropyl]methoxy}-5-(3-methoxyazetidin-1-yl)pyridine-2-carbonyl]amino}butanoate and ethyl 2-ethyl-2-{[6-{[(1S,2R)-2-(fluoromethyl)cyclopropyl]methoxy}-5-(3-methoxyazetidin-1-yl)pyridine-2-carbonyl]amino}butanoate

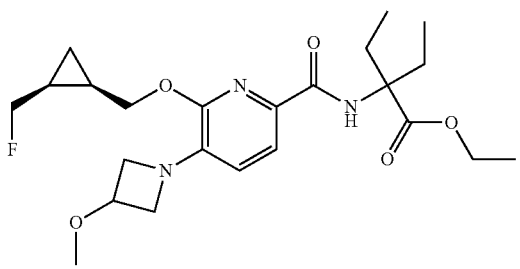 [SMILES: CCOC(=O)C(CC)(CC)NC(=O)c1ccc(N2CC(OC)C2)c(OC[C@@H]2C[C@@H]2CF)n1]

a) (Rac)-cis-5-bromo-6-((-2-(((tert-butyldimethylsilyl)oxy)methyl)cyclopropyl)methoxy)picolinic Acid

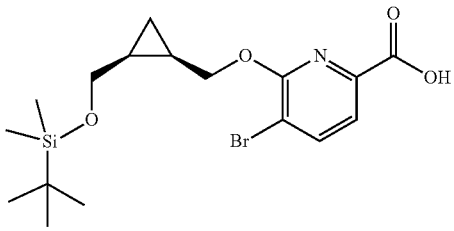 [SMILES: CC(C)(C)[Si](C)(C)OC[C@H]1C[C@H]1COc1nc(C(=O)O)ccc1Br]

In analogy to the procedure described in example 1 a, 5-bromo-6-chloropicolinic acid (CAN 959958-25-9) was reacted with (rac)-trans-(-2-(((tert-butyldimethylsilyl)methoxy)cyclopropyl)methanol (CAN 124200-37-9) to give the title compound as light yellow oil, MS (ISP): 418.162 [MH$^+$].

b) (Rac)-cis-ethyl 2-(5-bromo-6-((-2-(((tert-butyldimethylsilyl)oxy)methyl)cyclopropyl)methoxy)picolinamido)-2-ethylbutanoate

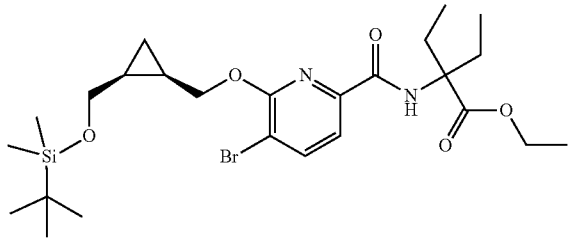 [SMILES: CCOC(=O)C(CC)(CC)NC(=O)c1ccc(Br)c(OC[C@@H]2C[C@@H]2CO[Si](C)(C)C(C)(C)C)n1]

In analogy to the procedure described in example 1 b, (rac)-cis-5-bromo-6-((-2-(((tert-butyldimethylsilyl)oxy)methyl)cyclopropyl)methoxy)picolinic acid was reacted with ethyl 2-amino-2-ethylbutanoate hydrochloride (CAN 1135219-29-2) to give the title compound as colorless oil, LC-MS (UV peak area/ESI) 90%, 559.2032 [MH$^+$].

c) (Rac)-cis-ethyl 2-(6-((-2-(((tert-butyldimethylsilyl)oxy)methyl)cyclopropyl)methoxy)-5-(3-methoxyazetidin-1-yl)picolinamido)-2-ethylbutanoate

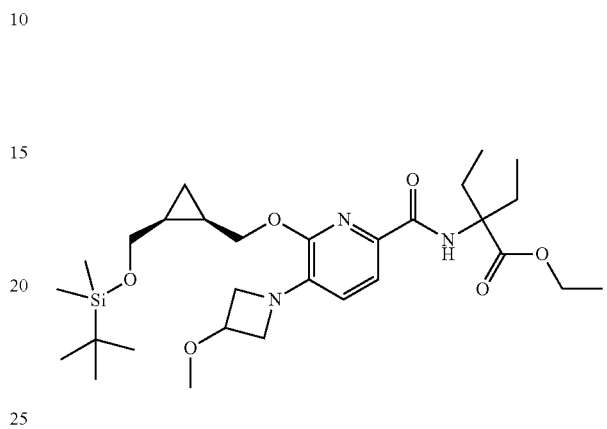

In analogy to the procedure described in example 1 c, (rac)-cis-ethyl 2-(5-bromo-6-((-2-(((tert-butyldimethylsilyl)oxy)methyl)cyclopropyl)methoxy)picolinamido)-2-ethylbutanoate was reacted with 3-methoxyazetidine hydrochloride (CAN 148644-09-1) to give the title compound (60 mg, 85%) as light yellow oil, LC-MS (UV peak area/ESI) 100%, 564.3469 [MH$^+$].

d) (Rac)-cis-ethyl 2-ethyl-2-(6-((-2-(hydroxymethyl)cyclopropyl)methoxy)-5-(3-methoxyazetidin-1-yl)picolinamido)butanoate

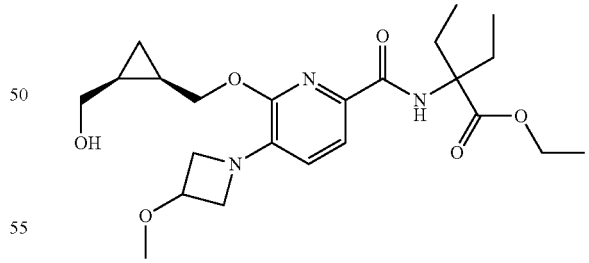

In analogy to the procedure described in example 1 d, (rac)-cis-ethyl 2-(6-((-2-(((tert-butyldimethylsilyl)oxy)methyl)cyclopropyl)methoxy)-5-(3-methoxyazetidin-1-yl)picolinamido)-2-ethylbutanoate was treated with AcOH to obtain crude title compound which was used in the next reaction step without further purification, MS (ISP): 550.343 [MH$^+$].

e) (Rac)-cis-ethyl 2-ethyl-2-(5-(3-methoxyazetidin-1-yl)-6-((-2-(((methylsulfonyl)oxy)methyl)cyclopropyl)methoxy)colinamido)butanoate

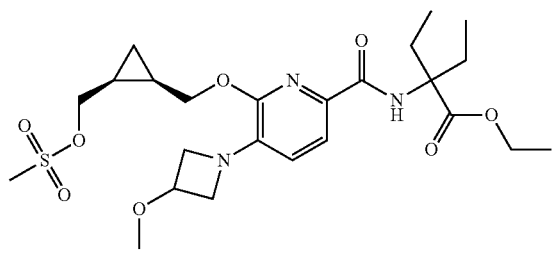 [SMILES: CCOC(=O)C(CC)(CC)NC(=O)c1ccc(N2CC(OC)C2)c(OC[C@@H]2C[C@@H]2COS(C)(=O)=O)n1]

In analogy to the procedure described in example 3 a, (rac)-cis-ethyl 2-ethyl-2-(6-((-2-(hydroxymethyl)cyclopropyl)methoxy)-5-(3-methoxyazetidin-1-yl)picolinamido)butanoate was reacted with methanesulfonyl chloride to obtain crude title compound which was used in the next reaction step without further purification, MS (ISP): 528.300 [MH⁺].

f) Ethyl 2-ethyl-2-{[6-{[(1R,2S)-2-(fluoromethyl)cyclopropyl]methoxy}-5-(3-methoxyazetidin-1-yl)pyridine-2-carbonyl]amino}butanoate and ethyl 2-ethyl-2-{[6-{[(1S,2R)-2-(fluoromethyl)cyclopropyl]methoxy}-5-(3-methoxyazetidin-1-yl)pyridine-2-carbonyl]amino}butanoate In analogy to the procedure described in example 3 b, (rac)-cis-ethyl 2-ethyl-2-(5-(3-methoxyazetidin-1-yl)-6-((-2-(((methylsulfonyl)oxy)methyl)cyclopropyl)methoxy)picolinamido)butanoate was reacted with TBAF to obtain the title compounds as colorless oil, MS (ISP): 452.351 [MH⁺].

Example 5

Ethyl 2-ethyl-2-{[6-({(1R,2S)-2-[(fluoromethoxy)methyl]cyclopropyl}methoxy)-5-(3-methoxyazetidin-1-yl)pyridine-2-carbonyl]amino}butanoate and ethyl 2-ethyl-2-{[6-({(1S,2R)-2-[(fluoromethoxy)methyl]cyclopropyl}methoxy)-5-(3-methoxyazetidin-1-yl)pyridine-2-carbonyl]amino}butanoate

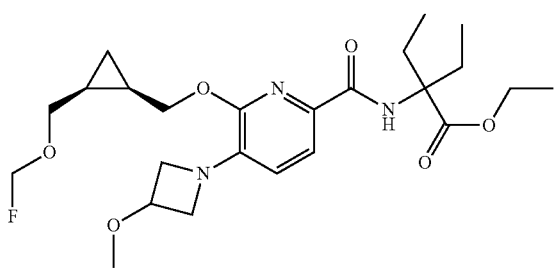 [SMILES: CCOC(=O)C(CC)(CC)NC(=O)c1ccc(N2CC(OC)C2)c(OC[C@@H]2C[C@@H]2COCF)n1]

In analogy to the procedure described in example 1 e, (rac)-cis-ethyl 2-ethyl-2-(6-((-2-(hydroxymethyl)cyclopropyl)methoxy)-5-(3-methoxyazetidin-1-yl)picolinamido)butanoate (example 4 d) was reacted with fluoro-iodo-methane to give the title compounds as colorless oil, MS (ISP): 482.370 [MH⁺].

Example 6

Ethyl 2-ethyl-2-{[6-({(1R,2S)-2-[(2-fluoroethoxy)methyl]cyclopropyl}methoxy)-5-(3-methoxyazetidin-1-yl)pyridine-2-carbonyl]amino}butanoate and ethyl 2-ethyl-2-{[6-({(1S,2R)-2-[(2-fluoroethoxy)methyl]cyclopropyl}methoxy)-5-(3-methoxyazetidin-1-yl)pyridine-2-carbonyl]amino}butanoate

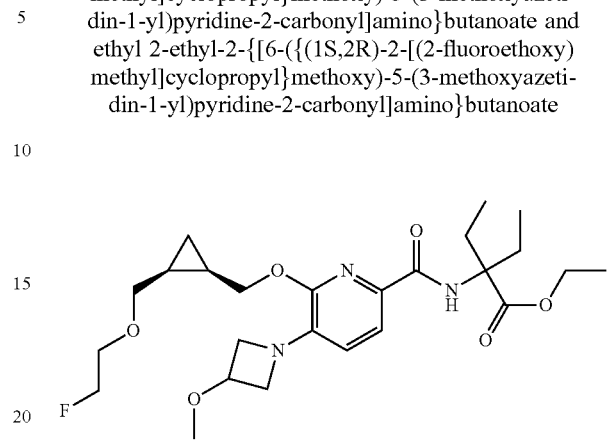

In analogy to the procedure described in example 1 e, (rac)-cis-ethyl 2-ethyl-2-(6-((-2-(hydroxymethyl)cyclopropyl)methoxy)-5-(3-methoxyazetidin-1-yl)picolinamido)butanoate (example 4 d) was reacted with fluoro-iodo-ethane to give the title compounds as colorless oil, MS (ISP): 496.324 [MH⁺].

Example 7

Ethyl 2-{[6-(cyclopropylmethoxy)-4-fluoro-5-(3-methoxyazetidin-1-yl)pyridine-2-carbonyl]amino}-2-ethylbutanoate

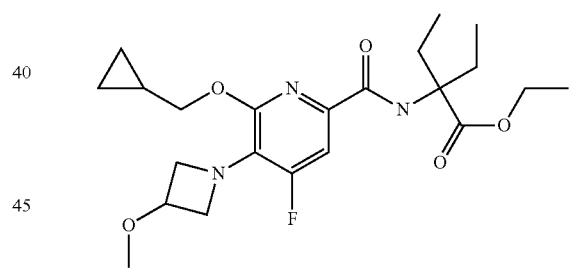

a) Ethyl 2-(4-bromo-6-(cyclopropylmethoxy)-5-(3-methoxyazetidin-1-yl)picolinamido)-2-ethylbutanoate

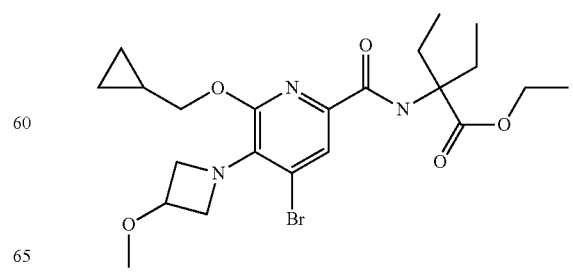

In a 5 mL round-bottomed flask, ethyl 2-(6-(cyclopropylmethoxy)-5-(3-methoxyazetidin-1-yl)picolinamido)-2-ethylbutanoate (CAN 1778678-14-0.28 mg, 66.7 µmol, Eq: 1) was combined with DMF (1.5 mL) to give a light yellow solution. N-Bromosuccinimide (23.8 mg, 133 µmol, Eq: 2) was added and the reaction was stirred at RT for 30 min. The mixture was diluted with EtOAc and washed with water/brine (1×15 mL) and brine (2×15 mL). The organic layers were dried over Na$_2$SO$_4$ and concentrated in vacuo. The crude product was purified by column chromatography (SiO$_2$, 5 g, hept.EtOAc) to give the title compound (21 mg, 63%) as colorless oil, MS (ISP): 498.229 [MH$^+$].

b) Ethyl 2-{[6-(cyclopropylmethoxy)-4-fluoro-5-(3-methoxyazetidin-1-yl)pyridine-2-carbonyl]amino}-2-ethylbutanoate In a 5 mL round-bottomed flask, ethyl 2-(4-bromo-6-(cyclopropylmethoxy)-5-(3-methoxyazetidin-1-yl)picolinamido)-2-ethylbutanoate (21 mg, 42.1 µmol, Eq: 1) and CsF (128 mg, 843 µmol, Eq: 20) were combined with DMSO (500 µL) to give a white suspension. The reaction mixture was heated to 120° C. for 7 d, diluted with EtOAc and washed with brine (3×15 mL). The organic layers were dried over Na$_2$SO$_4$ and concentrated in vacuo. The crude product was purified by prep. HPLC to give the title compound (0.7 mg, 4%) as white solid, LC-MS (UV peak area/ESI) 100%, 438.2417 [MH$^+$].

Example 8

Ethyl 2-ethyl-2-({6-[3-(fluoromethoxy)-2,2-dimethylpropoxy]-5-(3-methoxyazetidin-1-yl)pyridine-2-carbonyl}amino)butanoate

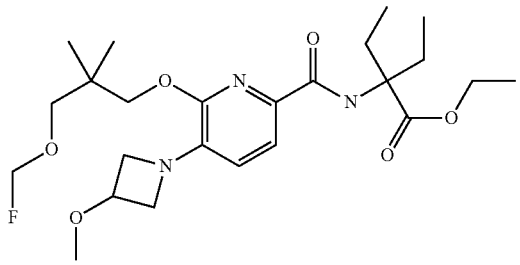 [SMILES: CCOC(=O)C(CC)(CC)NC(=O)c1ccc(N2CC(OC)C2)c(OCC(C)(C)COCF)n1]

a) 6-(3-(Benzyloxy)-2,2-dimethylpropoxy)-5-bromopicolinic Acid

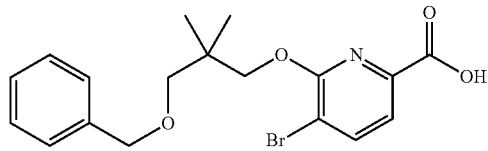 [SMILES: CC(C)(COCc1ccccc1)COc1nc(C(=O)O)ccc1Br]

In analogy to the procedure described in example 1 a, 5-bromo-6-chloropicolinic acid (CAN 959958-25-9) was reacted with 3-(benzyloxy)-2,2-dimethylpropan-1-ol (CAN 66582-32-9) to give the title compound as white solid, MS (ISP): 394.060 [MH$^+$].

b) Ethyl 2-(6-(3-(benzyloxy)-2,2-dimethylpropoxy)-5-bromopicolinamido)-2-ethylbutanoate

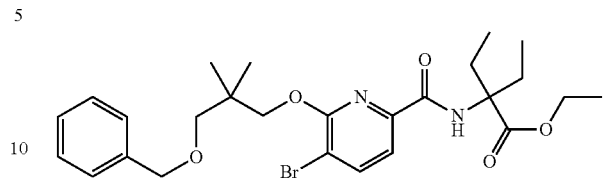

In analogy to the procedure described in example 1 b, 6-(3-(benzyloxy)-2,2-dimethylpropoxy)-5-bromopicolinic acid was reacted with ethyl 2-amino-2-ethylbutanoate hydrochloride (CAN 1135219-29-2) to give the title compound as yellow oil, MS (ISP): 535.200 [MH$^+$].

c) Ethyl 2-(6-(3-(benzyloxy)-2,2-dimethylpropoxy)-5-(3-methoxyazetidin-1-yl)picolinamido)-2-ethylbutanoate

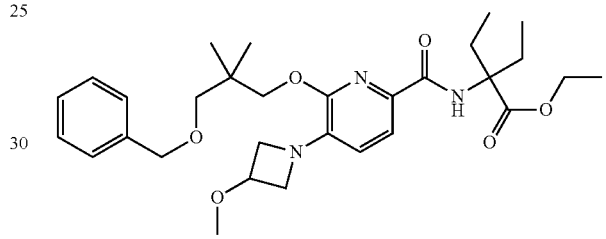

In analogy to the procedure described in example 1 c, ethyl 2-(6-(3-(benzyloxy)-2,2-dimethylpropoxy)-5-bromopicolinamido)-2-ethylbutanoate was reacted with 3-methoxyazetidine hydrochloride (CAN 148644-09-1) to give the title compound (680 mg, 88%) as light yellow oil, MS (ISP): 542.357 [MH$^+$].

d) Ethyl 2-ethyl-2-(6-(3-hydroxy-2,2-dimethylpropoxy)-5-(3-methoxyazetidin-1-yl)picolinamido)butanoate

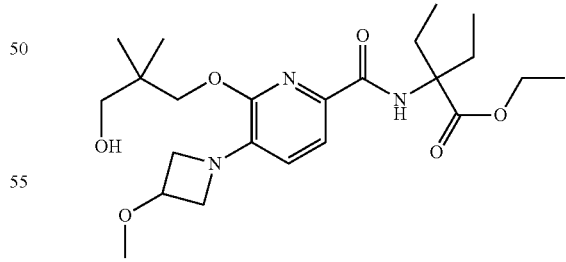

In a 100 mL round-bottomed flask, ethyl 2-(6-(3-(benzyloxy)-2,2-dimethylpropoxy)-5-(3-methoxyazetidin-1-yl)picolinamido)-2-ethylbutanoate (665 mg, 1.23 mmol, Eq: 1) was combined with EtOAc (30 mL) and MeOH (3 mL) to give a light yellow solution. Pd—C on charcoal (600 mg, 5.64 mmol, Eq: 4.59) was added. The mixture was stirred under hydrogen atmosphere for 48 h. The reaction mixture was filtered through celite and the organic solvent was removed under reduced pressure to give the target compound (523 mg, 94%) as white solid, MS (ISP): 452.351 [MH⁺].

e) Ethyl 2-ethyl-2-({6-[3-(fluoromethoxy)-2,2-dimethylpropoxy]-5-(3-methoxyazetidin-1-yl)pyridine-2-carbonyl}amino)butanoate In analogy to the procedure described in example 1 e, ethyl 2-ethyl-2-(6-(3-hydroxy-2,2-dimethylpropoxy)-5-(3-methoxyazetidin-1-yl)picolinamido)butanoate was reacted with fluoro-iodo-methane to give the title compound as colorless oil, MS (ISP): 484.237 [MH⁺].

Example 9

(+)-trans-Ethyl 2-ethyl-2-{[6-({-2-[(fluoromethoxy)methyl]cyclopropyl}methoxy)-5-(3-methoxyazetidin-1-yl)pyridine-2-carbonyl]amino}butanoate

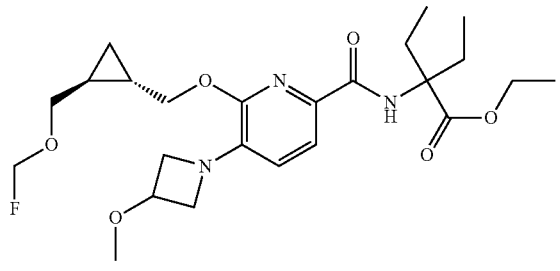 [SMILES: CCOC(=O)C(CC)(CC)NC(=O)c1ccc(N2CC(OC)C2)c(OC[C@H]2C[C@@H]2COCF)n1]

a) (+)-trans-Ethyl 2-ethyl-2-(6-((-2-(hydroxymethyl)cyclopropyl)methoxy)-5-(3-methoxyazetidin-1-yl)picolinamido)butanoate

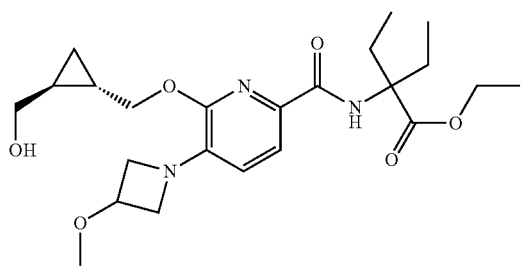 [SMILES: CCOC(=O)C(CC)(CC)NC(=O)c1ccc(N2CC(OC)C2)c(OC[C@H]2C[C@@H]2CO)n1]

(Rac)-trans-ethyl 2-ethyl-2-(6-((-2-(hydroxymethyl)cyclopropyl)methoxy)-5-(3-methoxyazetidin-1-yl)picolinamido)butanoate (example 1 d) was subjected to preparative chiral HPLC (column Chiralpak AD, 90% heptane/10% ethanol and NH₄OAc). The organic solvent was removed under reduced pressure and the residue diluted with EtOAc. The organic phase was washed with water (3×50 mL) and brine (1×50 mL). The organic layers were dried over Na₂SO₄ and concentrated in vacuo to give the title compound as light yellow oil, LC-MS (UV peak area/ESI) 100%, 450.2624 [MH⁺].

b) (+)-trans-Ethyl 2-ethyl-2-{[6-({-2-[(fluoromethoxy)methyl]cyclopropyl}methoxy)-5-(3-methoxyazetidin-1-yl)pyridine-2-carbonyl]amino}butanoate In a 5 mL round-bottomed flask, (+)-trans-ethyl 2-ethyl-2-(6-((-2-(hydroxymethyl)cyclopropyl)methoxy)-5-(3-methoxyazetidin-1-yl)picolinamido)butanoate (56 mg, 125 μmol, Eq: 1) was combined with DMF (1 mL) to give a light yellow solution. Sodium hydride on mineral oil (24.9 mg, 623 μmol, Eq: 5) was added and the reaction mixture was stirred for 30 min at RT. Fluoro-iodo-methane (99.6 mg, 42 μL, 623 μmol, Eq: 5) was added and stirring was continued for 90 min. The reaction mixture was diluted with EtOAc and washed with brine (3×10 mL). The organic layers were dried over Na₂SO₄ and concentrated in vacuo. The crude product was purified by column chromatography (SiO₂, 5 g, hept./EtOAc) to give the title compound (10 mg, 17%) as colorless oil, MS (ISP): 482.319 [MH⁺].

Example 10

(−)-trans-Ethyl 2-ethyl-2-{[6-({-2-[(fluoromethoxy)methyl]cyclopropyl}methoxy)-5-(3-methoxyazetidin-1-yl)pyridine-2-carbonyl]amino}butanoate

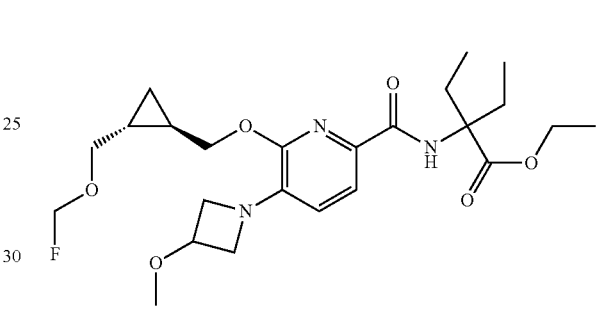

a) (−)-trans-Ethyl 2-ethyl-2-(6-((-2-(hydroxymethyl)cyclopropyl)methoxy)-5-(3-methoxyazetidin-1-yl)picolinamido)butanoate or Enantiomer

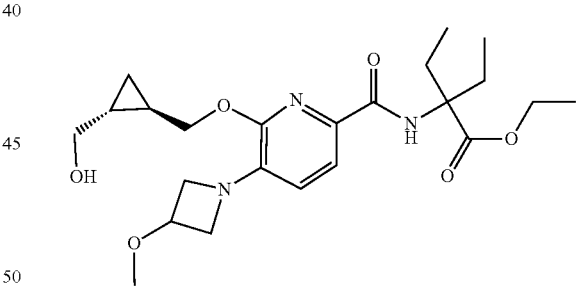

In analogy to the procedure described in example 9 a, (rac)-trans-ethyl 2-ethyl-2-(6-((-2-(hydroxymethyl)cyclopropyl)methoxy)-5-(3-methoxyazetidin-1-yl)picolinamido)butanoate (example 1 d) was subjected to preparative chiral HPLC to give the title compound as light yellow oil, LC-MS (UV peak area/ESI) 99%, 450.2631 [MH⁺].

b) (−)-trans-Ethyl 2-ethyl-2-{[6-({-2-[(fluoromethoxy)methyl]cyclopropyl}methoxy)-5-(3-methoxyazetidin-1-yl)pyridine-2-carbonyl]amino}butanoate In analogy to the procedure described in example 9 b, (−)-trans-ethyl 2-ethyl-2-(6-((-2-(hydroxymethyl)cyclopropyl)methoxy)-5-(3-methoxyazetidin-1-yl)picolinamido)butanoate was reacted with fluoro-iodo-methane to give the title compound as colorless oil, MS (ISP): 482.319 [MH⁺].

Example 11

(−)-trans-Fluoromethyl 2-ethyl-2-{[6-{[(1R,2R)-2-(hydroxymethyl)cyclopropyl]methoxy}-5-(3-methoxyazetidin-1-yl)pyridine-2-carbonyl]amino}butanoate

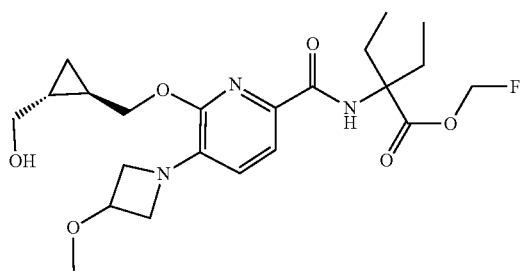 [SMILES: CCC(CC)(NC(=O)c1ccc(N2CC(OC)C2)c(OC[C@@H]2C[C@H]2CO)n1)C(=O)OCF]

a) (−)-trans-2-Ethyl-2-(6-((-2-(hydroxymethyl)cyclopropyl)methoxy)-5-(3-methoxyazetidin-1-yl)picolinamido)butanoic Acid

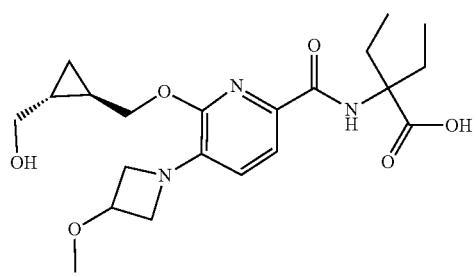 [SMILES: CCC(CC)(NC(=O)c1ccc(N2CC(OC)C2)c(OC[C@@H]2C[C@H]2CO)n1)C(=O)O]

In a 10 mL round-bottomed flask, (−)-trans-ethyl 2-ethyl-2-(6-((-2-(hydroxymethyl)cyclopropyl)methoxy)-5-(3-methoxyazetidin-1-yl)picolinamido)butanoate (example 10 a, 117 mg, 260 μmol, Eq: 1) was combined with THF (2 mL), MeOH (2.2 mL) and water (2 mL) to give a colorless solution. KOH (73 mg, 1.3 mmol, Eq: 5) was added. The mixture was stirred at 90° C. for 18 h. The organic solvent was removed under reduced pressure. The aqueous phase was adjusted to pH 2 (1 M HCl) and extracted with EtOAc (3×5 mL). The combined extracts were washed with brine (1×10 mL), dried over Na₂SO₄ and filtered. The solvent was removed under reduced pressure to give crude title compound (110 mg, quant.) as colorless oil which was used in the next reaction step without further purification, LC-MS (ES): 420.3 [M−H⁻].

b) (−)-trans-Fluoromethyl 2-ethyl-2-{[6-{[-2-(hydroxymethyl)cyclopropyl]methoxy}-5-(3-methoxyazetidin-1-yl)pyridine-2-carbonyl]amino}butanoate In a 50 mL test tube K₂CO₃ (32.5 mg, 235 μmol, Eq: 3) was combined with DMF (2 mL) to give a white suspension. (−)-trans-2-Ethyl-2-(6-((-2-(hydroxymethyl)cyclopropyl)methoxy)-5-(3-methoxyazetidin-1-yl)picolinamido)bu-tanoic acid (33 mg, 78.3 μmol, Eq: 1) and fluoro-iodo-methane (37.6 mg, 15.9 μL, 235 μmol, Eq: 3) were added. Stirring was continued for 2 h. The solvent was removed under reduced pressure. The crude product was purified by column chromatography (SiO₂, 5 g, hept./EtOAc) to give the title compound (23 mg, 65%) as colorless oil, MS (ISP): 454.308 [MH⁺].

Example 12

(+)-trans-Fluoromethyl 2-ethyl-2-{[6-{[-2-(hydroxymethyl)cyclopropyl]methoxy}-5-(3-methoxyazetidin-1-yl)pyridine-2-carbonyl]amino}butanoate

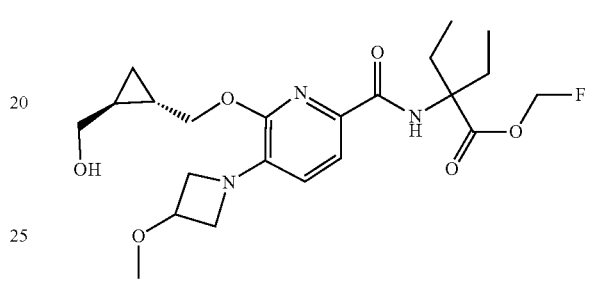

a)(+)-trans-2-Ethyl-2-(6-((-2-(hydroxymethyl)cyclopropyl)methoxy)-5-(3-methoxyazetidin-1-yl)picolinamido)butanoic Acid

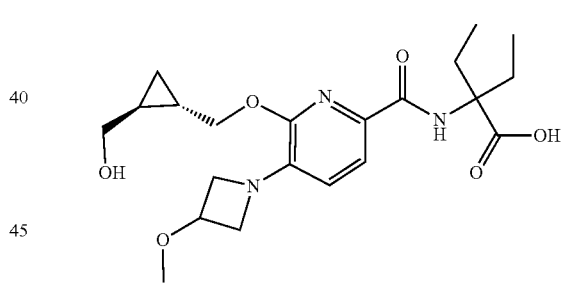

In analogy to the procedure described in example 11 a, (+)-trans-ethyl 2-ethyl-2-(6-((-2-(hydroxymethyl)cyclopropyl)methoxy)-5-(3-methoxyazetidin-1-yl)picolinamido)butanoate (example 9 a) was treated with KOH to give the title compound as white solid, MS (ISP): 422.281 [MH⁺].

b) (+)-trans-Fluoromethyl 2-ethyl-2-{[6-{[-2-(hydroxymethyl)cyclopropyl]methoxy}-5-(3-methoxyazetidin-1-yl)pyridine-2-carbonyl]amino}butanoate In analogy to the procedure described in example 11 b, (+)-trans-2-ethyl-2-(6-((-2-(hydroxymethyl)cyclopropyl)methoxy)-5-(3-methoxyazetidin-1-yl)picolinamido)bu-tanoic acid was reacted with fluoro-iodo-methane to give the title compound as colorless oil, MS (ISP): 454.308 [MH⁺].

Example 13

(+)-trans-2-Fluoroethyl 2-ethyl-2-{[6-{[-2-(hydroxymethyl)cyclopropyl]methoxy}-5-(3-methoxyazetidin-1-yl)pyridine-2-carbonyl]amino}butanoate

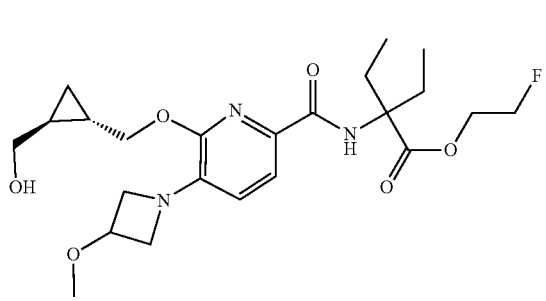 [SMILES: CCC(CC)(NC(=O)c1ccc(N2CC(OC)C2)c(OC[C@H]2C[C@@H]2CO)n1)C(=O)OCCF]

In analogy to the procedure described in example 11 b, (+)-trans-2-ethyl-2-(6-((-2-(hydroxymethyl)cyclopropyl)methoxy)-5-(3-methoxyazetidin-1-yl)picolinamido)butanoic acid (example 12 a) was reacted with fluoro-iodoethane to give the title compound as colorless oil, MS (ISP): 468.313 [MH$^+$].

Example 14

(−)-trans-2-Fluoroethyl 2-ethyl-2-{[6-{[-2-(hydroxymethyl)cyclopropyl]methoxy}-5-(3-methoxyazetidin-1-yl)pyridine-2-carbonyl]amino}butanoate

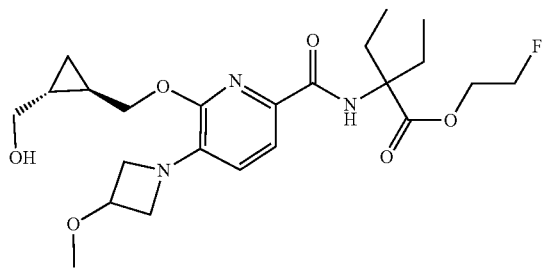 [SMILES: CCC(CC)(NC(=O)c1ccc(N2CC(OC)C2)c(OC[C@@H]2C[C@H]2CO)n1)C(=O)OCCF]

In analogy to the procedure described in example 11 b, (−)-trans-2-ethyl-2-(6-((-2-(hydroxymethyl)cyclopropyl)methoxy)-5-(3-methoxyazetidin-1-yl)picolinamido)butanoic acid (example 11 a) was reacted with fluoro-iodoethane to give the title compound as colorless oil, MS (ISP): 468.313 [MH$^+$].

Example 15

3-Fluoropropyl 2-ethyl-2-{[6-{[(1S,2S)-2-(hydroxymethyl)cyclopropyl]methoxy}-5-(3-methoxyazetidin-1-yl)pyridine-2-carbonyl]amino}butanoate

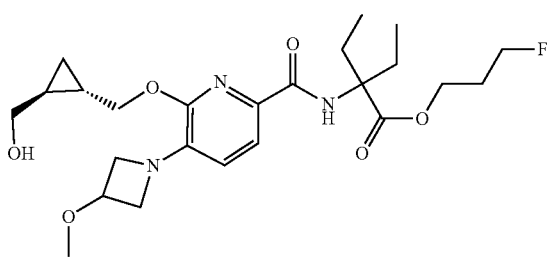 [SMILES: CCC(CC)(NC(=O)c1ccc(N2CC(OC)C2)c(OC[C@H]2C[C@@H]2CO)n1)C(=O)OCCCF]

a) Bis(1R,2S,5R)-5-methyl-2-(propan-2-yl)cyclohexyl Butanedioate

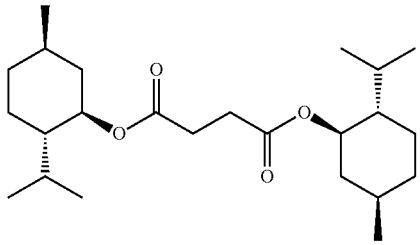 [SMILES: CC(C)[C@@H]1CC[C@@H](C)C[C@H]1OC(=O)CCC(=O)O[C@@H]1C[C@H](C)CC[C@H]1C(C)C]

A 2 L one-necked, round bottom flask was equipped with a stirrer, a Dean-Stark trap and a condenser. The flask was charged with succinic anhydride (64 g, 0.64 mol, 1 eq.), 1-menthol (199.88 g, 1.3 mol, 2 eq.), p-toluenesulfonic acid monohydrate (1.1 g, 6.39 mmol, 0.01 eq.) and tolune (576 mL). The mixture was heated under reflux for 24 h, cooled to 25° C., diluted with hexane (640 mL) and poured into a mixture of aqueous saturated sodium bicarbonate (800 mL), methanol (320 mL) and water (320 mL). The layers were separated and the aqueous phase was extracted with hexane (2×320 mL). The organic phases were combined, washed with brine (640 mL), dried over sodium sulphate and filtered. The solvent was removed under reduced pressure and the crude product was dissolved in methanol (240 mL). The solution was cooled to +4° C. for 16 h to form colorless crystals which were collected by filtration with suction. The crystals were purified by recrystallization from methanol (240 mL) to afford pure bis(1R,2S,5R)-5-methyl-2-(propan-2-yl)cyclohexyl butanedioate (212 g, 84%).

SOR value: [−87.64°] at ≅25° C., 1.0132% solution in CHCl$_3$.

b) 1,2-Bis(1R,2S,5R)-5-methyl-2-(propan-2-yl)cyclohexyl (1S,2S)-cyclopropane-1,2-dicarboxylate

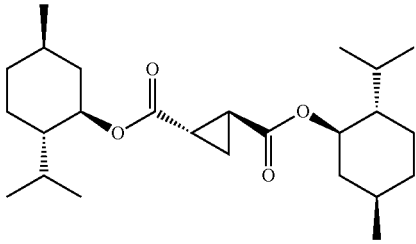 [SMILES: CC(C)[C@@H]1CC[C@@H](C)C[C@H]1OC(=O)[C@H]1C[C@@H]1C(=O)O[C@@H]1C[C@H](C)CC[C@H]1C(C)C]

A 1.8 M solution of butyllithium in THF (152.2 mmol, 84 mL) was added to 225 mL of THF at 0° C. under a N$_2$ atmosphere. Under stirring lithium tetramethylpiperidide (28.2 mL, 167 mmol) was added drop wise over a 20 min period. Stirring was continued at 0° C. for 1 h. Then the reaction mixture was cooled to −78° C. A solution of Bis(1R,2S,5R)-5-methyl-2-(propan-2-yl)cyclohexyl butanedioate (30 g, 76.1 mmol) in THF (60 mL) was added drop wise over a 20 min period. The yellow solution was stirred for 1 h.

Bromochloromethane (4.08 mL, 60.91 mmol) was added drop wise over a 20 min period. The mixture was stirred for 3 h at −78° C. A saturated aqueous solution of NH$_4$Cl (120 mL) was added. After stirring for 30 min at 25° C. the mixture was extracted with EtOAc (3×150 mL). The combined organic layers were washed with brine (200 mL), dried over Na$_2$SO$_4$, filtered, and concentrated in vacuo. The crude was purified by column chromatography (SiO$_2$, 100-200 mesh, 0.5-1% of ethyl acetate and hexane) to afford the title compound (38 g, 42%) as colorless crystals. Recrystallization of this material from methanol (380 mL) provided pure 1,2-bis(1R,2S,5R)-5-methyl-2-(propan-2-yl)cyclohexyl (1S,2S)-cyclopropane-1,2-dicarboxylate (27 g, 36%).

SOR value: [+18.18°] at ≅25° C., 1.0288% solution in CHCl$_3$.

c) (1S,2S)-Cyclopropane-1,2-dicarboxylic acid mono-((1R,2S,5R)-2-isopropyl-5-methyl-cyclohexyl) ester

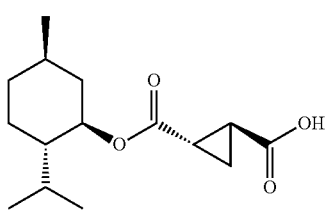 [SMILES: CC(C)[C@@H]1CC[C@@H](C)C[C@H]1OC(=O)[C@H]1C[C@@H]1C(=O)O]

To a solution of 1,2-bis(1R,2S,5R)-5-methyl-2-(propan-2-yl)cyclohexyl (1S,2S)-cyclopropane-1,2-dicarboxylate (25 g, 61.58 mmol) in isopropanol (250 mL) was added a 5 M solution of NaOH (13.54 mL, 67.73 mmol) at 25° C. The mixture was stirred at 70° C. for 16 h. The organic solvent was removed under reduced pressure. Water (200 mL) was added and the mixture was washed with diethyl ether (2×150 mL). The aqueous layer was acidified with 2 N HCl (pH~2) and extracted with ethyl acetate (3×250 mL). The combined organic layers were dried over Na$_2$SO$_4$, filtered and concentrated under reduced pressure to get (1S,2S)-2-({[(1R,2S,5R)-5-methyl-2-(propan-2-yl)cyclohexyl]oxy}carbonyl)cyclopropane-1-carboxylic acid (11.4 g, 69%) as off white semisolid.

d) (1R,2S,5R)-5-Methyl-2-(propan-2-yl)cyclohexyl (1S,2S)-2-(hydroxymethyl) cyclopropane-1-carboxylate

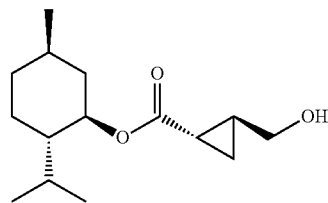 [SMILES: CC(C)[C@@H]1CC[C@@H](C)C[C@H]1OC(=O)[C@H]1C[C@@H]1CO]

To a stirred solution of (S,2S)-cyclopropane-1,2-dicarboxylic acid mono-((1R,2S,5R)-2-isopropyl-5-methyl-cyclohexyl) ester (20 g, 74.63 mmol) in THF (200 mL) was added a 1 M solution of borane in THF (56 mL) drop wise at −78° C. The mixture was stirred for 1 h at 25° C. and quenched with aq. NH$_4$Cl solution (150 mL). The organic solvent was removed under reduced pressure. Water was added (50 mL) and the mixture was extracted with ethyl acetate (2×100 mL). The combined organic layers were washed with brine (80 mL), dried over Na$_2$SO$_4$, filtered and concentrated under reduced pressure. The crude was purified by silica gel column chromatography (15-19% ethyl acetate/hexane) to get (1R,2S,5R)-5-methyl-2-(propan-2-yl) cyclohexyl (1S,2S)-2-(hydroxymethyl)cyclopropane-1-carboxylate (13.66 g, 72%) as yellowish semi solid.

e) (1R,2S,5R)-5-Methyl-2-(propan-2-yl)cyclohexyl (1S,2S)-2-[(benzyloxy) methyl]cyclopropane-1-carboxylate

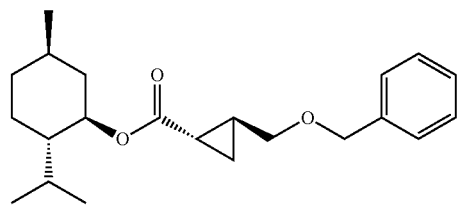 [SMILES: CC(C)[C@@H]1CC[C@@H](C)C[C@H]1OC(=O)[C@H]1C[C@@H]1COCc1ccccc1]

To a stirred solution of (1R,2S,5R)-5-methyl-2-(propan-2-yl)cyclohexyl (1S,2S)-2-(hydroxymethyl) cyclopropane-1-carboxylate (20 g, 78.74 mmol) in DMF (140 mL) was added NaH (4.72 g, 118.11 mmol) at 0° C. The mixture was stirred at 25° C. for 30 min. Benzylbromide (18.70 mL, 157.48 mmol) was added and stirring was continued at 25° C. for 30 min. Aqueous NH$_4$Cl solution (150 mL) was added and the mixture was extracted with EtOAc (2×150 mL). The combined organic layers were washed with water (3×120 mL), dried over Na$_2$SO$_4$, filtered and concentrated under reduced pressure. The crude was purified by silica gel column chromatography (1.9% EtOAc/hexane) to get (R,2S,5R)-5-methyl-2-(propan-2-yl)cyclohexyl (1S,2S)-2-[(benzyloxy)methyl]cyclopropane-1-carboxylate (22 g, 81%) as light yellow oil.

f) [(1S,2S)-2-[(Benzyloxy)methyl]cyclopropyl]methanol

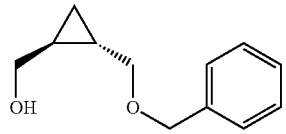 [SMILES: OC[C@H]1C[C@@H]1COCc1ccccc1]

To a stirred solution of (1R,2S,5R)-5-methyl-2-(propan-2-yl)cyclohexyl (1S,2S)-2-[(benzyloxy) methyl] cyclopropane-1-carboxylate (10 g, 29.07 mmol) in THF (200 mL) was added LAH (58.14 mL, 1 M in THF) at 0° C. The reaction mixture was stirred for 40 min at 0° C. and quenched with aq NH₄Cl solution (100 mL). The organic solvent was removed under reduced pressure. The solution was extracted with ethyl acetate (3×100 mL). The combined organic layers were brought to dryness and the crude was purified using silica gel column chromatography (30-35% ethyl acetate/hexane) to get [(1S,2S)-2-[(benzyloxy)methyl]cyclopropyl]methanol (5.33 g, 95%) as light yellow oil.

g) 6-{[(1S,2S)-2-[(Benzyloxy)methyl]cyclopropyl]methoxy}-5-bromopyridine-2-carboxylic Acid

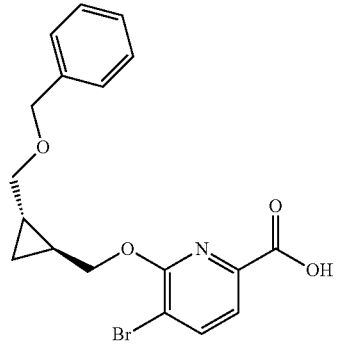 [SMILES: O=C(O)c1ccc(Br)c(OC[C@H]2C[C@@H]2COCc2ccccc2)n1]

To a solution of 5-bromo-6-chloropyridine-2-carboxylic acid (CAN 959958-25-9, 4 g, 19.80 mmol) in DMF (45 mL) was added NaH (2.77 g, 69.31 mmol) portion wise at 0° C. and stirred for 20 min at 0° C. [(S,2S)-2-[(Benzyloxy)methyl]cyclopropyl]methanol (4.18 g, 21.78 mmol) in DMF (15 mL) was added drop wise at 0° C. The mixture was stirred for 15 min at 25° C., heated to 80° C. for 3 h, cooled to 25° C. and quenched with 2 N aq. HCl to pH~2. Waster (100 mL) was added and the mixture was extracted with EtOAc (3×150 mL). The combined organic layers were washed with water (4×50 mL) and brine (50 mL), dried over Na₂SO₄ and concentrated under reduced pressure to get 6-{[(S,2S)-2-[(benzyloxy)methyl]cyclopropyl]methoxy}-5-bromopyridine-2-carboxylic acid (7.7 g, 99%) as off white sticky liquid.

LCMS:

Column Zorbax Ext C 18 (50×4.6 mm), 5μ, (mobile phase: from 90% [10 mM NH₄OAc in water] and 10% [CH₃CN] to 70% [10 mM NH₄OAc in water] and 30% [CH₃CN] in 1.5 min, further to 10% [10 mM NH₄OAc in water] and 90% [CH₃CN] in 3.0 min, held this mobile phase composition to 4 min and finally back to initial condition in 5 min). Purity is 76.78%, Rt=2.60 min, MS calculate: 391, MS found: 391.8[M+H⁺].

h) Ethyl 2-[(6-{[(1S,2S)-2-[(benzyloxy)methyl]cyclopropyl]methoxy}-5-bromopyridin-2-yl)formamido]-2-ethylbutanoate

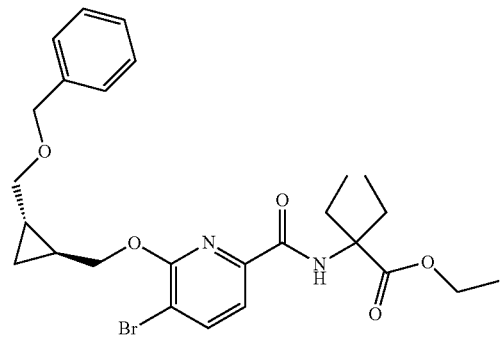 [SMILES: CCOC(=O)C(CC)(CC)NC(=O)c1ccc(Br)c(OC[C@H]2C[C@@H]2COCc2ccccc2)n1]

To a solution of 6-{[(1S,2S)-2-[(benzyloxy)methyl]cyclopropyl]methoxy}-5-bromopyridine-2-carboxylic acid (15.5 g, 39.54 mmol) in DMF (100 mL) were added DIPEA (27.49 mL, 158.16 mmol), ethyl 2-amino-2-ethylbutanoate (CAN 189631-96-7, 7.73 g, 39.54 mmol) and TBTU (15.25 g, 47.449 mmol). The reaction mixture was stirred at 25° C. for 16 h, poured into water (170 mL) and extracted with EtOAc (3×200 mL). The combined organic layers were washed with water (4×120 mL) and brine (100 mL), dried over Na₂SO₄, filtered and brought to dryness. The crude was purified via silica gel column chromatography (25% ethyl acetate/hexanes) to get ethyl 2-[(6-{[(1S,2S)-2-[(benzyloxy)methyl]cyclopropyl]methoxy}-5-bromopyridin-2-yl)formamido]-2-ethylbutanoate (20.5 g, 97%) as light brown oil.

LCMS:

Column Zorbax Ext C 18 (50×4.6 mm), 5μ, (mobile phase: from 90% [10 mM NH₄OAc in water] and 10% [CH₃CN] to 70% [10 mM NH₄OAc in water] and 30% [CH₃CN] in 1.5 min, further to 10% [10 mM NH₄OAc in water] and 90% [CH₃CN] in 3.0 min, held this mobile phase composition to 4 min and finally back to initial condition in 5 min). Purity is 91.47%, Rt=2.58 min, MS calculate: 533, MS found: 533.0 [M+H⁺].

i) Ethyl 2-[(6-{[(1S,2S)-2-[(benzyloxy) methyl]cyclopropyl]methoxy}-5-(3-methoxyazetidin-1-yl)pyridin-2-yl)formamido]-2-ethylbutanoate

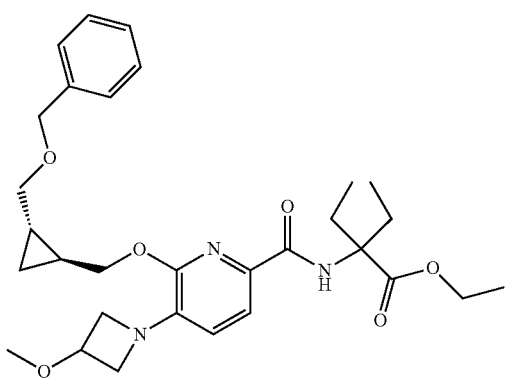 [SMILES: CCOC(=O)C(CC)(CC)NC(=O)c1ccc(N2CC(OC)C2)c(OC[C@H]2C[C@@H]2COCc2ccccc2)n1]

To a solution ethyl 2-[(6-{[(1S,2S)-2-[(benzyloxy)methyl]cyclopropyl]methoxy}-5-bromopyridin-2-yl)formamido]-2-ethylbutanoate (4 g, 7.50 mmol) in toluene (160 mL) were added 3-methoxyazetidine (1.39 g, 11.26 mmol) and cesium carbonate (7.33 g, 22.51 mmol). The mixture was degassed with argon for 10 min. Rac-BINAP (0.935 g, 1.50 mmol) and Pd(II)acetate (0.34 g, 1.50 mmol) were added. The mixture was heated to 110° C. for 3 h, diluted with EtOAc (100 mL), filtered through a celite bed and washed with EtOAc (3×100 mL). The filtrate was concentrated and the crude purified through silica gel column chromatography (42-50% ethyl acetate/hexanes) to get ethyl 2-[(6-{[(1S,2S)-2-[(benzyloxy)methyl]cyclopropyl]methoxy}-5-(3-methoxyazetidin-1-yl)pyridin-2-yl)formamido]-2-ethylbutanoate (3.1 g, 76%) as light brown oil.
LCMS:
Column Zorbax Ext C 18 (50×4.6 mm), 5μ, (mobile phase: from 90% [10 mM NH₄OAc in water] and 10% [CH₃CN] to 70% [10 mM NH₄OAc in water] and 30% [CH₃CN] in 1.5 min, further to 10% [10 mM NH₄OAc in water] and 90% [CH₃CN] in 3.0 min, held this mobile phase composition to 4 min and finally back to initial condition in 5 min). Purity is 96.74%, Rt=2.37 min, MS calculate: 539, MS found: 539.9 [M+H⁺].

j) Ethyl 2-ethyl-2-[(6-{[(1S,2S)-2-(hydroxymethyl)cyclopropyl]methoxy}-5-(3-methoxyazetidin-1-yl)pyridin-2-yl)formamido]butanoat

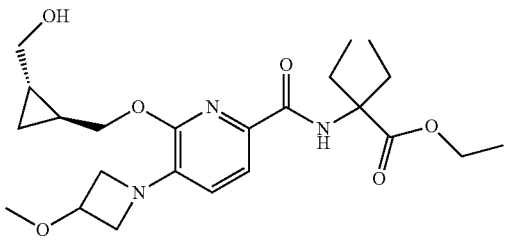 [SMILES: CCOC(=O)C(CC)(CC)NC(=O)c1ccc(N2CC(OC)C2)c(OC[C@H]2C[C@@H]2CO)n1]

A stirred solution of ethyl 2-[(6-{[(S,2S)-2-[(benzyloxy)methyl]cyclopropyl]methoxy}-5-(3-methoxyazetidin-1-yl)pyridin-2-yl)formamido]-2-ethylbutanoate (26 g, 48.24 mmol) in 735 mL EtOAc:MeOH (10:1) was degassed for 30 min. Pd/C (10%) (6.5 g) was added. The mixture was hydrogenated under a hydrogen atmosphere at 40 PSI for 28 h at 25° C., filtered through a celite bed and washed with 10% MeOH/EtOAc (4×200 mL). The filtrate was evaporated under reduced pressure to get the crude. The crude was purified applying silica gel column chromatography (10-50% EtOAc:hexanes) to get ethyl 2-ethyl-2-[(6-{[(1S,2S)-2-(hydroxymethyl)cyclopropyl]methoxy}-5-(3-methoxyazetidin-1-yl)pyridin-2-yl)formamido] butanoate (19.3 g, 89%) as colorless sticky liquid.
SOR value:
[+15.51°] at ≅20° C., 0.2514% in MeOH.
LCMS:
Column Zorbax Ext C 18 (50×4.6 mm), 5μ, (mobile phase: from 90% [10 mM NH₄OAc in water] and 10% [CH₃CN] to 70% [10 mM NH₄OAc in water] and 30% [CH₃CN] in 1.5 min, further to 10/a [10 mM NH₄OAc in water] and 90/[CH₃CN] in 3.0 min, held this mobile phase composition to 4 min and finally back to initial condition in 5 min). Purity is 98.93%, Rt=3.26 min, MS calculate: 449, MS found: 449.9 [M+H⁺].

k) 2-Ethyl-2-[(6-{[(1S,2S)-2-(hydroxymethyl)cyclopropyl]methoxy}-5-(3-methoxyazetidin-1-yl)pyridin-2-yl)formamido]butanoic Acid

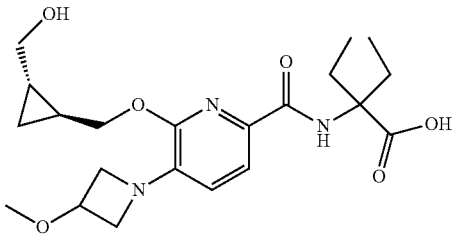 [SMILES: CCC(CC)(NC(=O)c1ccc(N2CC(OC)C2)c(OC[C@H]2C[C@@H]2CO)n1)C(=O)O]

In a 25 ml round-bottomed flask, ethyl 2-ethyl-2-[(6-{[(1S,2S)-2-(hydroxymethyl)cyclopropyl]methoxy}-5-(3-methoxyazetidin-1-yl)pyridin-2-yl)formamido]butanoate (100 mg, 0.22 mmol) was combined with THF (2.0 mL), MeOH (2.2 mL) and water (2.0 mL) to give a light yellow solution. KOH pellets (62 mg, 1.11 mmol) were added. The mixture was heated to 90° C. After 18 h the organic solvent was removed under reduced pressure. The aqueous phase was diluted with water (20 mL) and extracted with diethyl ether (2×10 mL). The combined organic layers were discarded. The aqueous phase was adjusted to pH~2 (1 M HCl) and extracted with EtOAc (3×15 mL). The combined organic layers were washed with brine (10 mL), dried, filtered and brought to dryness under reduced pressure to get pure 2-ethyl-2-[(6-{[(1S,2S)-2-(hydroxymethyl)cyclopropyl]methoxy}-5-(3-methoxyazetidin-1-yl)pyridin-2-yl)formamido]butanoic acid (90 mg, 96%) as colorless sticky mass.
LCMS:
Column Zorbax Ext C 18 (50×4.6 mm), 5μ, (mobile phase: from 90% [10 mM NH₄OAc in water] and 10% [CH₃CN] to 70% [10 mM NH₄OAc in water] and 30% [CH₃CN] in 1.5 min, further to 10% [10 mM NH₄OAc in water] and 90% [CH₃CN] in 3.0 min, held this mobile phase composition to 4 min and finally back to initial condition in 5 min). Purity is 95.49%, Rt=2.00 min, MS calculate: 419, MS found: 420.4 [M+H⁺].

l) 3-{[(4-Methylbenzene)sulfonyl]oxy}propyl 2-ethyl-2-[(6-{[(1S,2S)-2-(hydroxymethyl)cyclopropyl]methoxy}-5-(3-methoxyazetidin-1-yl)pyridin-2-yl)formamido]butanoate

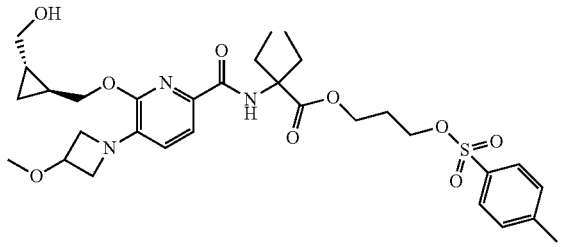

To a solution of 2-ethyl-2-{[(6-[(S,2S)-2-(hydroxymethyl)cyclopropyl]methoxy}-5-(3-methoxyazetidin-1-yl)pyridin-2-yl)formamido]butanoic acid (260 mg, 0.62 mmol) in DMF (5 mL) were added K₂CO₃ (256 mg, 1.85 mmol) and 3-{[(4-methylbenzene)sulfonyl]oxy}propyl 4-methylbenzene-1-sulfonate (711 mg, 1.85 mmol). The reaction mixture was stirred for 16 h at 25° C., poured into water, quenched with aq. 1 (N) HCl and extracted with EtOAc (3×40 mL). The combined organic layers were washed with brine (30 mL), dried, filtered and concentrated in vacuo to get crude product which was purified by combiflash using silica column and 20-80% EtOAc in hexane to get pure 3-{[(4-methylbenzene)sulfonyl]oxy}propyl 2-ethyl-2-[(6-{[(1S,2S)-2-(hydroxymethyl)cyclopropyl]methoxy}-5-(3-methoxyazetidin-1-yl)pyridin-2-yl)formamido]butanoate (255 mg, 65%) as colorless sticky mass.

LCMS:

Column Zorbax Ext C 18 (50×4.6 mm), 5μ, (mobile phase: from 90% [10 mM NH$_4$OAc in water] and 10% [CH$_3$CN] to 70% [10 mM NH$_4$OAc in water] and 30% [CH$_3$CN] in 1.5 min, further to 10% [10 mM NH$_4$OAc in water] and 90% [CH$_3$CN] in 3.0 min, held this mobile phase composition to 4 min and finally back to initial condition in 5 min). Purity is 90.68%, Rt=3.48 min, MS calculate: 633, MS found: 634.4 [M+H$^+$].

m) 3-Fluoropropyl 2-ethyl-2-{[6-{[(1S,2S)-2-(hydroxymethyl)cyclopropyl]methoxy}-5-(3-methoxyazetidin-1-yl)pyridine-2-carbonyl]amino}butanoate In analogy to the procedure described in example 11 b, 2-ethyl-2-(6-(((1S,2S)-2-(hydroxymethyl)cyclopropyl)methoxy)-5-(3-methoxyazetidin-1-yl)picolinamido)butanoic acid (example 12 a) was reacted with fluoro-iodopropane to give the title compound as colorless oil, MS (ISP): 482.370 [MH$^+$].

Example 16

3-Fluoropropyl 2-ethyl-2-{[6-{[(1R,2R)-2-(hydroxymethyl)cyclopropyl]methoxy}-5-(3-methoxyazetidin-1-yl)pyridine-2-carbonyl]amino}butanoate

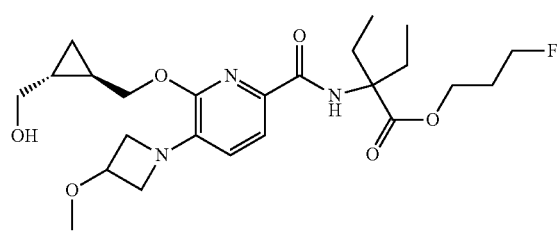 [SMILES: CCC(CC)(NC(=O)c1ccc(N2CC(OC)C2)c(OC[C@@H]2C[C@H]2CO)n1)C(=O)OCCCF]

In analogy to the procedure described in example 11 b, (−)-trans-2-ethyl-2-(6-((-2-(hydroxymethyl)cyclopropyl)methoxy)-5-(3-methoxyazetidin-1-yl)picolinamido)butanoic acid (example 11 a) was reacted with fluoro-iodopropane to give the title compound as colorless oil, MS (ISP): 482.319 [MH$^+$].

Example 17

N-[(2S)-1-(2-Fluoroethoxy)-4-methylpentan-2-yl]-5-(3-methoxyazetidin-1-yl)-6-[(oxetan-3-yl)methoxy]pyridine-2-carboxamide

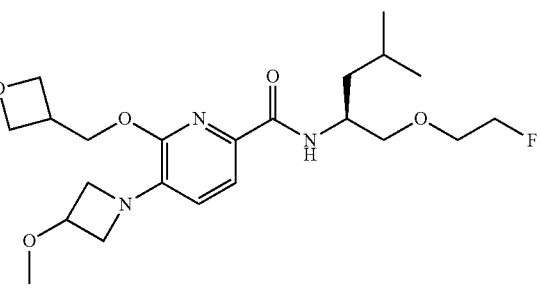

a) 5-Bromo-6-(oxetan-3-ylmethoxy)picolinic Acid

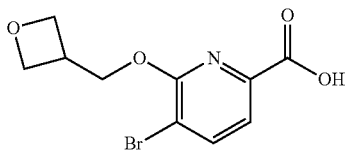 [SMILES: O=C(O)c1ccc(Br)c(OCC2COC2)n1]

In analogy to the procedure described in example 1 a, 5-bromo-6-chloropicolinic acid (CAN 959958-25-9) was reacted with 3-oxetanemethanol (CAN 6246-06-6) to give the title compound as light brown solid, MS (ISP): 287.998 [MH$^+$].

b) Methyl 5-bromo-6-(oxetan-3-ylmethoxy)picolinate

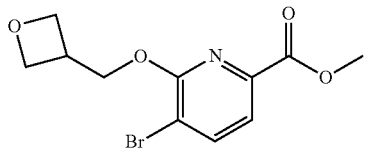 [SMILES: COC(=O)c1ccc(Br)c(OCC2COC2)n1]

In analogy to the procedure described in example 11 b, 5-bromo-6-(oxetan-3-ylmethoxy)picolinic acid was reacted with iodomethane to give the title compound as colorless oil, MS (ISP): 302.003 [MW].

c) Methyl 5-(3-methoxyazetidin-1-yl)-6-(oxetan-3-ylmethoxy)picolinate

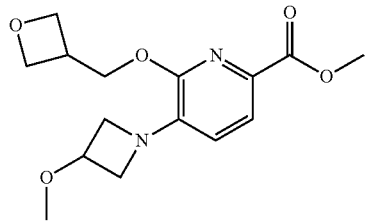 [SMILES: COC(=O)c1ccc(N2CC(OC)C2)c(OCC2COC2)n1]

In analogy to the procedure described in example 1 c, methyl 5-bromo-6-(oxetan-3-ylmethoxy)picolinate was reacted with 3-methoxyazetidine hydrochloride (CAN 148644-09-1) to give the title compound as light yellow oil, MS (ISP): 309.209 [MH$^+$].

d) 5-(3-Methoxyazetidin-1-yl)-6-(oxetan-3-yl-methoxy)picolinic Acid

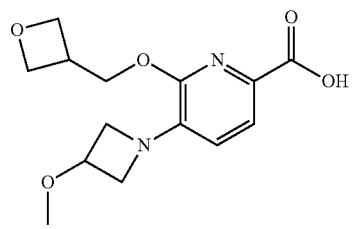 [SMILES: COC1CN(c2ccc(C(=O)O)nc2OCC2COC2)C1]

In analogy to the procedure described in example 1 a, methyl 5-(3-methoxyazetidin-1-yl)-6-(oxetan-3-ylmethoxy) picolinate was treated with KOH to give crude title compound which was used in the next reaction step without further purification.

e) (S)-N-(1-Hydroxy-4-methylpentan-2-yl)-5-(3-methoxyazetidin-1-yl)-6-(oxetan-3-ylmethoxy)picolinamide

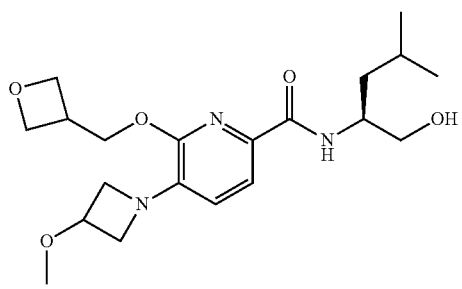 [SMILES: COC1CN(c2ccc(C(=O)N[C@H](CO)CC(C)C)nc2OCC2COC2)C1]

In a 5 mL round-bottomed flask, 5-(3-methoxyazetidin-1-yl)-6-(oxetan-3-ylmethoxy)picolinic acid (45 mg, 153 µmol, Eq: 1) was combined with DMF (1 mL) to give a light yellow solution. TBTU (58.9 mg, 183 µmol, Eq: 1.2) and DIPEA (98.8 mg, 134 µL, 765 µmol, Eq: 5) were added. L-Leucinol (CAN 7533-40-6, 53.8 mg, 58.6 µL, 459 µmol, Eq: 3) was added and the mixture was stirred at RT for 30 min. The solvent was removed under reduced pressure and the crude product was purified by column chromatography (SiO$_2$, 10 g, hept./EtOAc) to give the title compound (44 mg, 73%) as colorless solid, MS (ISP): 394.326 [MH$^+$].

f) N-[(2S)-1-(2-Fluoroethoxy)-4-methylpentan-2-yl]-5-(3-methoxyazetidin-1-yl)-6-[(oxetan-3-yl)methoxy]pyridine-2-carboxamide In a 10 mL round-bottomed flask, (S)-N-(1-hydroxy-4-methylpentan-2-yl)-5-(3-methoxyazetidin-1-yl)-6-(oxetan-3-ylmethoxy)picolinamide (45 mg, 114 µmol, Eq: 1) was combined with DMF (1 mL) to give a yellow solution which was cooled to 0° C. Sodium hydride, disperision on mineral oil (13.7 mg, 343 µmol, Eq: 3) was added and the mixture was allowed to warm to RT. After 15 min 1-fluoro-2-iodoethane (99.5 mg, 47.4 µL, 572 µmol, Eq: 5) was added and stirring was continued at RT. The addition of sodium hydride (Eq: 3) and 1-fluoro-2-iodoethane (Eq: 5) was repeated after 15, 17 and 20 h. After additional 2 h stirring at RT the reaction mixture was diluted with EtOAc and washed with brine (3×10 mL). The organic layers were dried over Na$_2$SO$_4$ and concentrated in vacuo. The crude product was purified by prep. HPLC to obtain the title compound (6 mg, 12%) as colorless oil, LC-MS (UV peak area/ESI) 99%, 440.2561 [MH$^+$].

Example 18

N-[(2S)-1-(2-Fluoroethoxy)-4-methylpentan-2-yl]-6-[(oxetan-3-yl)methoxy]-5-(pyrrolidin-1-yl)pyridine-2-carboxamide

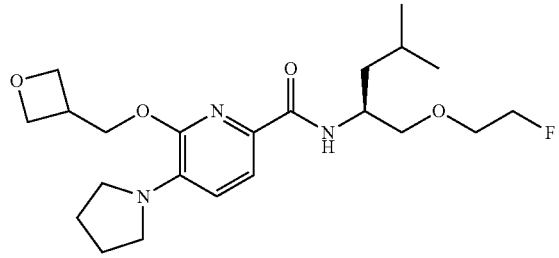 [SMILES: CC(C)C[C@@H](COCCF)NC(=O)c1ccc(N2CCCC2)c(OCC2COC2)n1]

a) Methyl 6-(oxetan-3-ylmethoxy)-5-(pyrrolidin-1-yl)picolinate

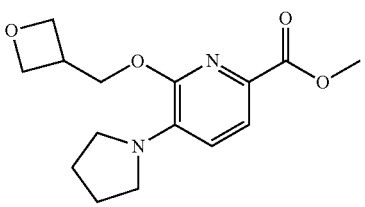 [SMILES: COC(=O)c1ccc(N2CCCC2)c(OCC2COC2)n1]

In analogy to the procedure described in example 1 c, methyl 5-bromo-6-(oxetan-3-ylmethoxy)picolinate (example 17 b) was reacted with pyrrolidine (CAN 123-75-1) to give the title compound as light yellow oil, MS (ISP): 293.162 [MH$^+$].

b) 5-(3-Methoxyazetidin-1-yl)-6-(oxetan-3-yl-methoxy)picolinic Acid

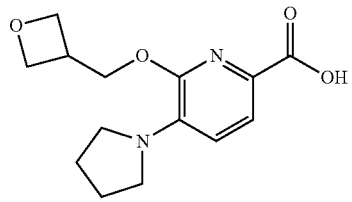 [SMILES: O=C(O)c1ccc(N2CCCC2)c(OCC2COC2)n1]

In analogy to the procedure described in example 11 a, methyl 6-(oxetan-3-ylmethoxy)-5-(pyrrolidin-1-yl)picolinate was treated with KOH to give crude title compound which was used in the next reaction step without further purification, LC-MS (ES): 279.2 [MH$^+$].

c) (S)-N-(1-Hydroxy-4-methylpentan-2-yl)-6-(oxetan-3-ylmethoxy)-5-(pyrrolidin-1-yl)picolinamide

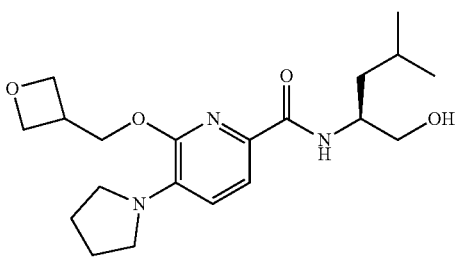 [SMILES: CC(C)C[C@@H](CO)NC(=O)c1ccc(N2CCCC2)c(OCC2COC2)n1]

In analogy to the procedure described in example 17 e, 5-(3-methoxyazetidin-1-yl)-6-(oxetan-3-ylmethoxy)picolinic acid was reacted with L-leucinol to give the title compound as light yellow oil, MS (ISP): 378.327 [MH$^+$].

d) N-[(2S)-1-(2-Fluoroethoxy)-4-methylpentan-2-yl]-6-[(oxetan-3-yl)methoxy]-5-(pyrrolidin-1-yl)pyridine-2-carboxamide In analogy to the procedure described in example 17 f, (S)-N-(1-hydroxy-4-methylpentan-2-yl)-6-(oxetan-3-yl-methoxy)-5-(pyrrolidin-1-yl)picolinamide was reacted with 1-fluoro-2-iodoethane to obtain the title compound as as colorless oil, MS (ISP): 424.387 [MH$^+$].

Example 19

(1,1,2,2,3,3-Hexadeuterio-3-fluoro-propyl) 2-ethyl-2-[[6-[[(1S,2S)-2-(hydroxymethyl)cyclopropyl]methoxy]-5-(3-methoxyazetidin-1-yl)pyridine-2-carbonyl]amino]butanoate

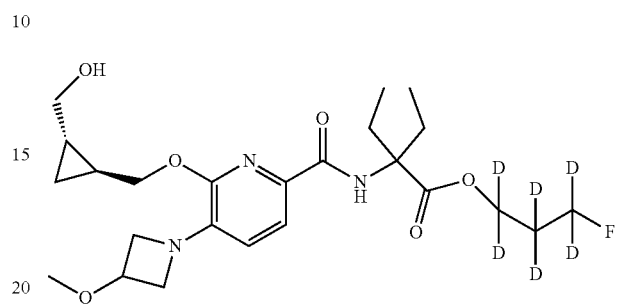

a) (1,1,2,2,3,3-Hexadeuterio-3-hydroxy-propyl) 4-methylbenzenesulfonate

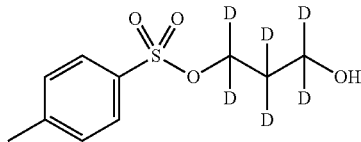 [SMILES: [2H]C([2H])(O)C([2H])([2H])C([2H])([2H])OS(=O)(=O)c1ccc(C)cc1]

To a solution of 1,1,2,2,3,3-hexadeuteriopropane-1,3-diol (46 mg, 0.55 mmol) in DCM (1 mL) were added 2,6-lutidine (0.2 mL, 1.64 mmol) and tosyl chloride (156 mg, 0.82 mmol, 1.5 eq.). The reaction mixture was stirred for 17 h at 25° C., diluted with DCM (15 mL), washed with aq. 1 N HCl (10 mL and water (10 mL), dried, filtered and concentrated in vacuo. The crude was purified by column chromatography on silica gel (5-30% EtOAc in hexane) to get the title compound (50 mg, 41%) as colorless liquid.
LCMS:
Column Zorbax Ext C 18 (50×4.6 mm), 5μ, (mobile phase: from 90% [10 mM NH$_4$OAc in water] and 10% [CH$_3$CN] to 70% [10 mM NH$_4$OAc in water] and 30% [CH$_3$CN] in 1.5 min, further to 10% [10 mM NH$_4$OAc in water] and 90% [CH$_3$CN] in 3.0 min, held this mobile phase composition to 4 min and finally back to initial condition in 5 min). Purity is 99.72%, Rt=2.75 min, MS calculate: 236, MS found: 237.1 [M+H$^+$].

b) (1,1,2,2,3,3-Hexadeuterio-3-fluoro-propyl) 4-methylbenzenesulfonate

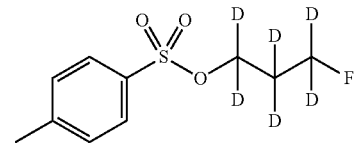 [SMILES: [2H]C([2H])(F)C([2H])([2H])C([2H])([2H])OS(=O)(=O)c1ccc(C)cc1]

Triethylamine.3HF (0.09 mL, 0.55 mmol) and XtalFluor-E® (94 mg, 0.41 mmol) were added to dichloromethane (5.0 mL). (1,1,2,2,3,3-Hexadeuterio-3-hydroxy-propyl) 4-methylbenzenesulfonate (65 mg, 0.27 mmol) was added and the reaction mixture was stirred for 17 h at 25° C. The reaction was quenched with 5% aq. NaHCO₃ solution. The layers were separated and the aqueous layer was extracted with DCM (2×10 mL). The combined organic layers were washed with brine (10 mL), dried, filtered and concentrated in vacuo. The crude was purified by column chromatography on silica gel (5-10% EtOAc in hexane) to get the title compound (50 mg, 80%) as colorless liquid which was used in the next reaction step without further purification.

c) (1,1,2,2,3,3-Hexadeuterio-3-fluoro-propyl) 2-ethyl-2-[[6-[[(1S,2S)-2-(hydroxymethyl)cyclopropyl]methoxy]-5-(3-methoxyazetidin-1-yl)pyridine-2-carbonyl]amino]butanoate To a solution of 2-ethyl-2-[(6-{[(1S,2S)-2-(hydroxymethyl)cyclopropyl]methoxy}-5-(3-methoxyazetidin-1-yl)pyridin-2-yl)formamido]butanoic acid (example 15 k, 40 mg, 0.09 mmol) in DMF (1.5 mL) were added K₂CO₃ (39 mg, 0.29 mmol) and (1,1,2,2,3,3-hexadeuterio-3-fluoropropoxy)methylbenzene (45 mg, 0.19 mmol). The reaction mixture was stirred for 17 h, quenched with water (20 mL) and extracted with EtOAc (3×20 mL). The combined organic layers were washed with brine (20 mL), dried, filtered and concentrated in vacuo. The crude was purified by column chromatography on silica gel (20-80% EtOAc in hexane) to obtain the title compound (35 mg, 77%) as colorless liquid.

LCMS:

Column Zorbax Ext C 18 (50×4.6 mm), 5μ, (mobile phase: from 90% [10 mM NH₄OAc in water] and 10% [CH₃CN] to 70% [10 mM NH₄OAc in water] and 30% [CH₃CN] in 1.5 min, further to 10% [10 mM NH₄OAc in water] and 90% [CH₃CN] in 3.0 min, held this mobile phase composition to 4 min and finally back to initial condition in 5 min). Purity is 83.98%, Rt=3.21 min, MS calculate: 487, MS found: 488.2 [M+H⁺].

Example 20

3-Fluoropropyl 2-[6-[[(1S,2S)-2-(hydroxymethyl)cyclopropyl]methoxy]-5-(3-methoxyazetidin-1-yl)pyridine-2-carbonylamino]-2-vinyl-but-3-enoate

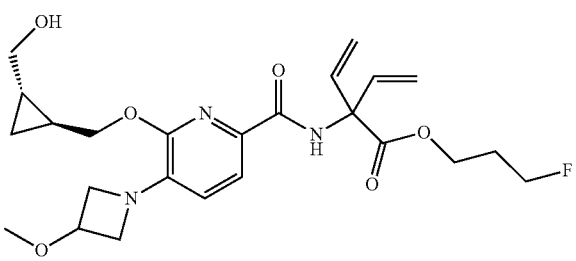 [SMILES: C=CC(C=C)(NC(=O)c1ccc(N2CC(OC)C2)c(OC[C@H]2C[C@@H]2CO)n1)C(=O)OCCCF]

a) 2-Ethyl-2-(6-(((1S,2S)-2-(hydroxymethyl)cyclopropyl)methoxy)-5-(3-methoxyazetidin-1-yl)picolinamido)butanoyl Azide

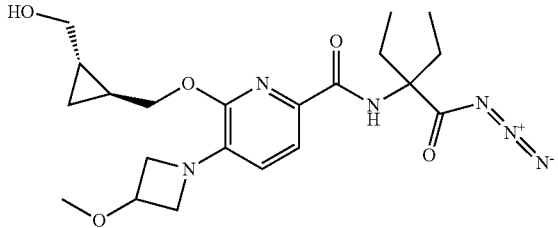 [SMILES: CCC(CC)(NC(=O)c1ccc(N2CC(OC)C2)c(OC[C@H]2C[C@@H]2CO)n1)C(=O)N=[N+]=[N-]]

In a 30 mL round bottom flask 2-ethyl-2-(6-(((1S,2S)-2-(hydroxymethyl)cyclopropyl)methoxy)-5-(3-methoxyazetidin-1-yl)picolinamido)butanoic acid (example 15 k, 338 mg, 802 μmol, 1 eq.) was dissolved in toluene (14 mL). Triethylamine (81 mg, 116 μL, 802 μmol, 1 eq.) and DPPA (221 mg, 173 μL, 802 μmol, 1 eq.) were added. The reaction mixture was stirred for 24 h at ambient temperature, poured onto water (20 mL) and extracted with AcOEt (3×30 mL). The combined organic layers were dried over sodium sulfate and concentrated in vacuo. The crude material was purified by flash chromatography (SiO₂, 120 g, 10-70% AcOEt in heptane) to give the title compound (177 mg, 0.396 mmol, 48%) as a off white solid.

¹H NMR (600 MHz, CDCl₃): δ ppm 8.32 (s, 2H, NH), 7.54-7.59 (d, ³J=7.9 Hz, 1H, $N_{Py}$—$C_q$—CH—CH), 6.46-6.53 (d, ³J=7.9 Hz, 1H, $N_{Py}$—$C_q$—$C_H$), 4.09-4.30 (m, 8H, m, O—CH₂, CH₂—N—CH₂, PO₃.O—CH₂, O—CH), 3.72-3.84 (m, 2H, CH₂—N—CH₂), 3.23 (s, 3H, O—CH₃), 2.35-2.51 (m, 2H, N₃—CO—$C_q$—CH₂), 1.68-1.89 (m, 2H, N₃—CO—$C_q$—CH₂), 1.24-1.34 (m, 2H, CH—CH₂—CH), 0.74 (t, 3-7.5 Hz, 6H, N₃—CO—$C_q$—CH₂—CH₃), 0.63-0.72 (m, 2H, CH—CH₂—CH)

HRMS (ESI): C₂₁H₃₀N₆O₅ [M+H]⁺ calculated=447.2304; found=447.2296.

b) 6-(((1S,2S)-2-(Hydroxymethyl)cyclopropyl)methoxy)-5-(3-methoxyazetidin-1-yl)picolinamide

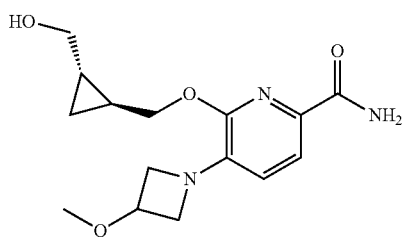 [SMILES: COC1CN(c2ccc(C(N)=O)nc2OC[C@H]2C[C@@H]2CO)C1]

In a 25 mL round bottom flask 2-ethyl-2-(6-(((1S,2S)-2-(hydroxymethyl)cyclopropyl)methoxy)-5-(3-methoxyazetidin-1-yl)picolinamido)butanoyl azide (177 mg, 0.396 mmol, 1 eq.) was dissolved in toluene (10.0 mL). The reaction mixture was heated to 110° C. upon stirring for 3 h and then concentrated in vacuo. THF (3 mL) and 3N NaOH (7 mL) were added. The reaction mixture was heated to 90° C. for 1 h upon stirring, poured onto water (10 mL) and extracted with AcOEt (3×40 mL). The combined organic layers were dried over sodium sulfate and concentrated in vacuo to give the title compound (85 mg, 0.277 mmol, 70%) as a light orange oil. The crude material was used in the next step without further purification.

$^1$H NMR (600 MHz, CDCl$_3$): δ ppm 8.18 (CO—NH$_2$), 7.74 (d, $^3$J=8.0 Hz, 1H, N$_{Py}$—C$_q$—CH—CH), 6.56 (d, $^3$J=8.0 Hz, 1H, N$_{Py}$—C$_q$—CH), 3.99-4.41 (m, 7H, O—CH$_2$, CH$_2$—N—CH$_2$, O—CH, HO—CH), 3.95-4.00 (m, 2H, CH$_2$—N—CH$_2$), 3.29 (m, 3H, O—CH$_3$), 1.20-1.36 (CH—CH$_2$—CH), 0.54-0.79 (m, 2H, CH—CH$_2$—CH)

MS (ESI): C$_{15}$H$_{21}$N$_3$O$_4$ [M+H]$^+$ calculated=308.14; found=308.20.

c) 6-(((1S,2S)-2-(Hydroxymethyl)cyclopropyl)methoxy)-5-(3-methoxyazetidin-1-yl)picolinic Acid

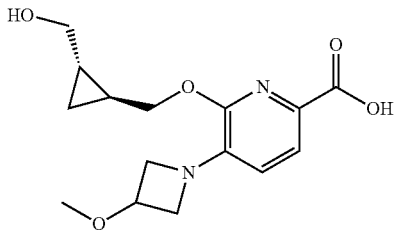 [SMILES: COC1CN(c2ccc(C(=O)O)nc2OC[C@H]2C[C@@H]2CO)C1]

In a 25 mL round bottom flask 6-(((1S,2S)-2-(hydroxymethyl)cyclopropyl)methoxy)-5-(3-methoxyazetidin-1-yl)picolinamide (85 mg, 0.277 mmol, 1 eq.) was dissolved in methanol (3 mL) and water (5 mL). Sodium hydroxide (55 mg, 1.38 mmol, 5 eq.) was added. The reaction mixture was heated to 85° C. for 12 h upon stirring, poured onto water (10 mL) and 1N HCl (3 mL) and extracted with AcOEt (3×20 mL). The combined organic layers were dried over sodium sulfate and concentrated in vacuo. The crude material was purified by flash chromatography (SiO$_2$, 12 g, 40-100% AcOEt in heptane) to give the title compound (64 mg, 0.207 mmol, 75%) as a light orange solid.

$^1$H NMR (600 MHz, CDCl$_3$): δ ppm 7.72 (dd, 3J=7.9 Hz, 4J=2.9 Hz, H, N$_{Py}$—C$_q$—CH—CH), 6.56 (d, $^3$J=7.9 Hz, 1H, N$_{Py}$—C$_q$—CH), 3.99-4.41 (m, 7H, O—CH$_2$, CH$_2$—N—CH$_2$, O—CH, HO—CH), 3.97-3.99 (m, 2H, CH$_2$—N—CH$_2$), 3.28 (m, 3H, O—CH$_3$), 1.18-1.32 (CH—CH$_2$—CH), 0.56-0.81 (m, 2H, CH—CH$_2$—CH)

HRMS (ESI): C$_{15}$H$_{20}$N$_2$O$_5$ [M+H]$^+$ calculated=309.1379; found=309.1451.

d) 3-Fluoropropyl 2-amino-2-vinylbut-3-enoate

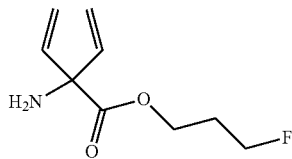

3-Fluoropropan-1-ol (1.55 g, 1.61 mL, 19.8 mmol, Eq.: 18) and 2-amino-2-vinylbut-3-enoic acid hydrochloride (CAN 1865695-91-5, 180 mg, 1.1 mmol, Eq.: 1) were added to a round bottom flask. Sulfurous dichloride (1.31 g, 798 μL, 11 mmol, Eq.: 10) was added. The reaction mixture was stirred for 1 h at 80° C., poured onto water (10 mL) and extracted with CH$_2$Cl$_2$ (2×20 mL). The organic layers were combined, dried over sodium sulfate, filtered and concentrated in vacuo. The crude material was purified by flash chromatography (silica gel, 12 g, 20% to 70% AcOEt in heptane) to give the title compound as colorless oil, LC-MS (UV peak area/ESI) 94%, 187.1083 [MH+].

e) 3-Fluoropropyl 2-(1,2-ditritioethyl)-2-[[6-[[(1S,2S)-2-(hydroxymethyl)cyclopropyl]methoxy]-5-(3-methoxyazetidin-1-yl)pyridine-2-carbonyl]amino]-3,4-ditritio-butanoate 6-(((1S,2S)-2-(Hydroxymethyl)cyclopropyl)methoxy)-5-(3-methoxyazetidin-1-yl)picolinic acid (19.8 mg, 64.1 μmol, Eq.: 0.8) and 3-fluoropropyl 2-amino-2-vinylbut-3-enoate (15 mg, 80.1 μmol, Eq.: 1) were dissolved in CH$_2$Cl$_2$ (1.34 mL). N-Ethyl-N-isopropylpropan-2-amine (41.4 mg, 55.2 μL, 320 μmol, Eq.: 4) followed by 1-(bis(dimethylamino)methylene)-1H-[1,2,3]triazolo[4,5-b]pyridine-1-ium 3-oxide hexafluorophosphate(V) (36.6 mg, 96.1 μmol, Eq.: 1.2) were added. The reaction mixture was stirred for 1 h at ambient temperature, poured onto water (10 mL) and extraced with CH$_2$Cl$_2$ (4×20 mL). The organic layers were combined, dried over sodium sulfate, filtered and concentrated in vacuo. The crude material was purified by flash chromatography (silica gel, 12 g, 20% to 70% AcOEt in heptane) to give the title compound as colorless oil, LC-MS (UV peak area/ESI) 98%, 478.2399 [MH+].

Example 21

3-Fluoropropyl 3,4-didenterio-2-(1,2-dideterio-ethyl)-2-[[6-[[(S,2S)-2-(hydroxymethyl)cyclopropyl]methoxy]-5-(3-methoxyazetidin-1-yl)pyridine-2-carbonyl]amino]butanoate

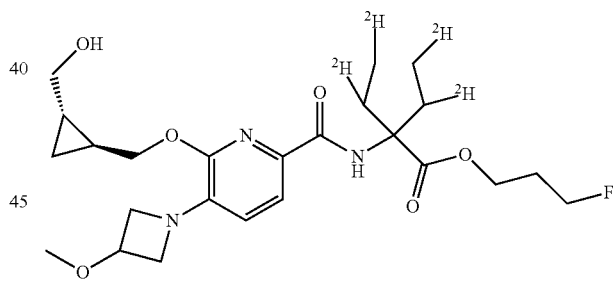

In a 2 ml deuteration flask, 3-Fluoropropyl 2-[[6-[[(1S,2S)-2-(hydroxymethyl)cyclopropyl]methoxy]-5-(3-methoxyazetidin-1-yl)pyridine-2-carbonyl]amino]-2-vinylbut-3-enoate (1.0 mg, 2.09 μmol, 1.0 eq.) and Pd/C (10%) (1.11 mg, 1.05 μmol, 0.5 eq.) was suspended in dimethylformamide (0.5 ml). The flask was attached to the deuterium manifold (RC-TRITEC) and degassed by freeze-pump-thaw.

Deuterium gas was introduced, and the black suspension was vigorously stirred for 2.5 hours under an atmosphere of deuterium at 600 mbar. The black suspension was filtered over a 17 mm Titan HPLC filter (0.45 μm, PTFE) and washed with methanol (3×2 ml). The colorless solution was concentrated to give 1 mg of the titel compound in >98% purity, as determined by HPLC (SunFire C18, 5 μm, 4.6×250 mm; eluent: acetonitrile [A], 5% acetonitrile in water [B]; gradient: 10% [A], 90% [B] to 99% [A], 1%[B] in 12 min, hold for 3 min, then back to initial conditions for 5 min). MS m/z: 483.4 [M(²H)+H]⁺ (4%), 484.4 [M(²H₂)+H]⁺ (9%), 485.4 [M(²H₃)+H]⁺ (14%), 486.4 [M(²H₄)+H]⁺ (27%), 487.4 [M(²H₅)+H]⁺ (21%), 488.4 [M(²H₆)+H]⁺ (18%), 489.4 [M(²H₇)+H]⁺ (7%).

Example 22

(Rac)-trans-3-Fluoropropyl 2-[[6-[[-2-(benzyloxymethyl)cyclopropyl]methoxy]-5-(3-hydroxyazetidin-1-yl)pyridine-2-carbonyl]amino]-2-ethyl-butanoate

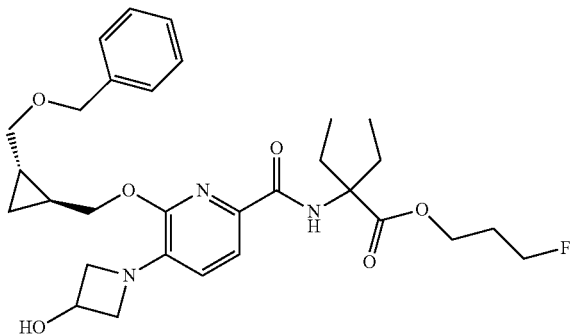 [SMILES: CCC(CC)(NC(=O)c1ccc(N2CC(O)C2)c(OC[C@H]2C[C@@H]2COCc2ccccc2)n1)C(=O)OCCCF]

a) (Rac)-trans-6-(-2-benzyloxymethyl-cyclopropylmethoxy)-5-bromo-pyridine-2-carboxylic Acid

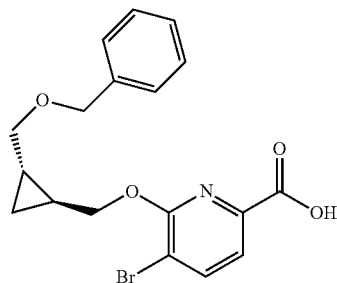 [SMILES: O=C(O)c1ccc(Br)c(OC[C@H]2C[C@@H]2COCc2ccccc2)n1]

A solution of 5-bromo-6-chloro-pyridine-2-carboxylic acid (2.0 g, 8.5 mmol) in DMF (35 mL) was cooled to 0° C. under argon. NaH (60% oil suspension, 1.01 g, 25.4 mmol) was added and the mixture was stirred for 20 minutes at 0° C. A solution of (rac)-trans-[-2-[(benzyloxy)methyl]cyclopropyl]methanol (2.277 g, 11.8 mmol) in DMF (5 mL) was slowly added. The mixture was heated to 80° C. for 3 h, cooled to 25° C. and adjusted to pH-2 with 2 N aq. HC solution. Water was added (400 mL) and the mixture was extracted with EtOAc (3×200 mL). The combined organic layers were washed with brine (150 mL), dried, filtered and concentrated in vacuo to give crude title compound as light yellow gum which was used in the next step without further purification.

LCMS:

Column Zorbax Ext C 18 (50×4.6 mm), 5μ, (mobile phase: from 90% [10 mM NH₄OAc in water] and 10% [CH₃CN] to 70% [10 mM NH₄OAc in water] and 30% [CH₃CN] in 1.5 min, further to 10% [10 mM NH₄OAc in water] and 90% [CH₃CN] in 3.0 min, held this mobile phase composition to 4 min and finally back to initial condition in 5 min). Purity is 71.32%, Rt=2.67 min, MS calculate: 392, MS found: 392.1 [M–H⁻].

b) (Rac)-trans-ethyl 2-[[6-[[-2-(benzyloxymethyl)cyclopropyl]methoxy]-5-bromo-pyridine-2-carbonyl]amino]-2-ethyl-butanoate

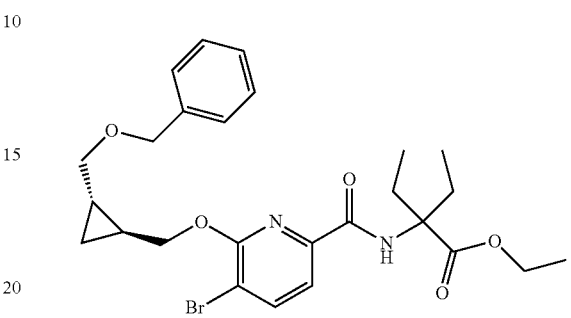

To a solution of (rac)-trans-6-(-2-benzyloxymethyl-cyclopropylmethoxy)-5-bromo-pyridine-2-carboxylic acid (3.3 g, 8.4 mmol) in DMF (15 mL) were added DIPEA (5.9 mL, 33.7 mmol), ethyl 2-amino-2-ethylbutanoate hydrochloride (1.646 g, 8.4 mmol) and TBTU (2.701 g, 8.4 mmol). The reaction mixture was stirred at 25° C. for 16 h, poured into water (200 mL) and extracted with EtOAc (3×100 mL). The combined organic layers were washed with brine (100 mL), dried, filtered and concentrated in vacuo. The crude material was purified by flash chromatography (silica gel, 0% to 5% AcOEt in hexane) to give the title compound (2.95 g, 66%) as colorless gum.

LCMS:

Column Zorbax Ext C 18 (50×4.6 mm), 5μ, (mobile phase: from 90% [10 mM NH₄OAc in water] and 10% [CH₃CN] to 70% [10 mM NH₄OAc in water] and 30% [CH₃CN] in 1.5 min, further to 10% [10 mM NH₄OAc in water] and 90% [CH₃CN] in 3.0 min, held this mobile phase composition to 4 min and finally back to initial condition in 5 min). Purity is 96.75%, Rt=4.65 min, MS calculate: 533, MS found: 534.8 [M+H⁺].

c) (Rac)-trans-2-[[6-[[-2-(benzyloxymethyl)cyclopropyl]methoxy]-5-bromo-pyridine-2-carbonyl]amino]-2-ethyl-butanoic Acid

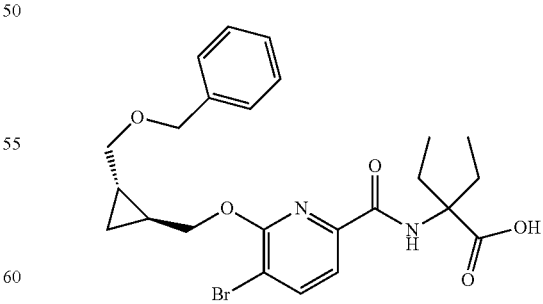

KOH (282 mg, 2.34 mmol) was added to a solution of (rac)-trans-ethyl 2-[(6-{[-2-[(benzyloxy)methyl]cyclopropyl]methoxy}-5-bromopyridin-2-yl)formamido]-2-ethylbutanoate (250 mg, 0.46 mmol) in THF (4 mL), MeOH (4.4 mL) and water (4.0 mL).

The mixture was heated to 90° C. for 18 h. The organic solvents were removed under reduced pressure. The pH of the remaining aqueous phase was adjusted to 2 using 1 M HC. Extraction with EtOAc (3×25 mL) followed. The combined organic layers were washed with brine (1×30 mL), dried, filtered and brought to dryness under reduced pressure to obtain the title compound (230 mg, 97%) as light yellow sticky mass.
LCMS:
Column Zorbax Ext C 18 (50×4.6 mm), 5μ, (mobile phase: from 90% [10 mM NH$_4$OAc in water] and 10% [CH$_3$CN] to 70% [10 mM NH$_4$OAc in water] and 30% [CH$_3$CN] in 1.5 min, further to 10% [10 mM NH$_4$OAc in water] and 90% [CH$_3$CN] in 3.0 min, held this mobile phase composition to 4 min and finally back to initial condition in 5 min). Purity is 99.03%, Rt=2.8 min, MS calculate: 505, MS found: 503.3[M+H$^+$].

d) (Rac)-trans-3-fluoropropyl 2-[(6-{[-2-[(benzyloxy)methyl]cyclopropyl]methoxy}-5-bromopyridin-2-yl)formamido]-2-ethylbutanoate

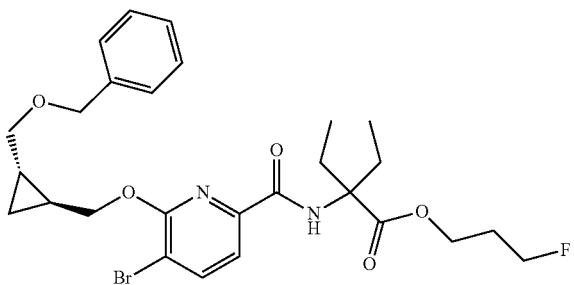 [SMILES: CCC(CC)(NC(=O)c1ccc(Br)c(OC[C@H]2C[C@@H]2COCc2ccccc2)n1)C(=O)OCCCF]

In a Round bottom flask K$_2$CO$_3$ (230 mg, 1.66 mmol) was suspended in DMF (8 mL). (Rac)-trans-2-[(6-{[-2-[(benzyloxy)methyl]cyclopropyl]methoxy}-5-bromopyridin-2-yl)formamido]-2-ethylbutanoic acid (280 mg, 0.55 mmol) and 1-iodo-3-fluoro-propane (313 mg, 1.66 mmol) were added. The mixture was stirred for 2 h at 25° C. Ice cold water was added and the mixture was extracted with EtOAc (3×50 mL). The combined organic layers were washed with brine (20 mL), dried, and concentrated in vacuo. The crude material was purified by flash chromatography (silica gel, 0% to 30% AcOEt in hexane) to give the title compound (225 mg, 72%) as colorless sticky mass.
LCMS:
Column Zorbax Ext C 18 (50×4.6 mm), 5μ, (mobile phase: from 90% [10 mM NH$_4$OAc in water] and 10% [CH$_3$CN] to 70% [10 mM NH$_4$OAc in water] and 30% [CH$_3$CN] in 1.5 min, further to 10% [10 mM NH$_4$OAc in water] and 90% [CH$_3$CN] in 3.0 min, held this mobile phase composition to 4 min and finally back to initial condition in 5 min). Purity is 99.38%, Rt=2.41 min, MS calculate: 565, MS found: 565.3 [M+H$^+$].

e) 3-Fluoropropyl 2-amino-2-vinylbut-3-enoate

To a solution of (rac)-trans-3-fluoropropyl 2-[(6-{[-2-[(benzyloxy)methyl]cyclopropyl]methoxy}-5-bromopyridin-2-yl)formamido]-2-ethylbutanoate (225 mg, 0.39 mmol) in toluene (5 mL) were added azetidin-3-ol-HCl (87 mg, 0.79 mmol) and cesium carbonate (519 mg, 1.59 mmol). The mixture was degassed with argon for 10 minutes. BINAP (100 mg, 0.16 mmol) and Pd(H) acetate (36 mg, 0.16 mmol) were added and the mixture was heated at 110° C. for 3 h. The reaction mixture was diluted with EtOAc (30 mL), filtered through a bed of celite and the celite bad was washed with EtOAc (30 mL). The solvent was removed in vacuo. The crude material was purified by flash chromatography (silica gel, 10% to 70% EtOAc in heptane) followed by SFC purification to give the title compound (130 mg, 59%) as yellowish sticky solid.
LCMS:
Column Zorbax Ext C 18 (50×4.6 mm), 5μ, (mobile phase: from 90% [10 mM NH$_4$OAc in water] and 10% [CH$_3$CN] to 70% [10 mM NH$_4$OAc in water] and 30% [CH$_3$CN] in 1.5 min, further to 10% [10 mM NH$_4$OAc in water] and 90% [CH$_3$CN] in 3.0 min, held this mobile phase composition to 4 min and finally back to initial condition in 5 min). Purity is 98.28%, Rt=3.63 min, MS calculate: 557, MS found: 558.0 [M+H$^+$].

Example 23

3-(p-Tolylsulfonyloxy)propyl 2-ethyl-2-[[6-[[(1S,2S)-2-(hydroxymethyl)cyclopropyl]methoxy]-5-(3-methoxyazetidin-1-yl)pyridine-2-carbonyl]amino]butanoate

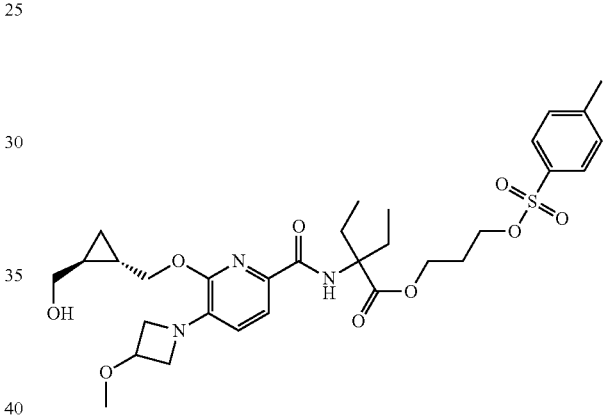

a) 3-{[(4-Methylbenzene)sulfonyl]oxy}propyl 4-methylbenzene-1-sulfonate

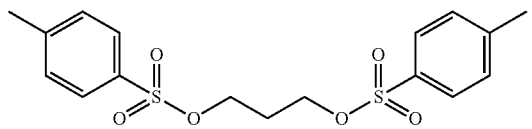

To a solution of propane-1,3-diol (500 mg, 6.58 mmol) in DCM (5 mL) were added 2,6-lutidine (2.3 mL, 19.74 mmol) and tosyl chloride (2.508 g, 13.16 mmol). The reaction mixture was stirred for 17 h at 25° C., diluted with DCM (50 mL), washed with aq. 1 HCl, water (20 mL), dried, filtered and concentrated in vacuo. The crude material was purified by flash chromatography (silica gel, 5% to 30% EtOAc in heptane) to obtain the title compound (1000 mg, 40%) as as white solid.
LCMS:
Column Zorbax Ext C 18 (50×4.6 mm), 5μ, (mobile phase: from 90% [10 mM NH$_4$OAc in water] and 10% [CH$_3$CN] to 70% [10 mM NH$_4$OAc in water] and 30% [CH$_3$CN] in 1.5 min, further to 10% [10 mM NH$_4$OAc in water] and 90% [CH$_3$CN] in 3.0 min, held this mobile phase composition to 4 min and finally back to initial condition in 5 min). Purity is 97.88%, Rt=3.56 min, MS calculate: 384, MS found: 402.1 [M+NH$_4^+$].

b) 3-(p-Tolylsulfonyloxy)propyl 2-ethyl-2-[[6-[[(1S,2S)-2-(hydroxymethyl)cyclopropyl]methoxy]-5-(3-methoxyazetidin-1-yl)pyridine-2-carbonyl]amino]butanoate To a solution of 2-ethyl-2-[(6-{[(1S,2S)-2-(hydroxymethyl)cyclopropyl]methoxy}-5-(3-methoxyazetidin-1-yl)pyridin-2-yl)formamido]butanoic acid (example 15 k, 260 mg, 0.62 mmol) in DMF (5 mL) were added K$_2$CO$_3$ (256 mg, 1.85 mmol) and 3-{[(4-methylbenzene)sulfonyl]oxy}propyl 4-methylbenzene-1-sulfonate (711 mg, 1.85 mmol). The reaction mixture was stirred for 16 h at 25° C., poured onto water, quenched with aq. 1 N HCl and extracted with EtOAc (3×40 mL). The combined organic layers were washed with brine (30 mL), dried, filtered and concentrated in vacuo. The crude material was purified by flash chromatography (silica gel, 20% to 80% EtOAc in heptane) to obtain the title compound (255 mg, 65%) as colorless sticky mass.
LCMS:
Column Zorbax Ext C 18 (50×4.6 mm), 5µ, (mobile phase: from 90% [10 mM NH$_4$OAc in water] and 10% [CH$_3$CN] to 70% [10 mM NH$_4$OAc in water] and 30% [CH$_3$CN] in 1.5 min, further to 10% [10 mM NH$_4$OAc in water] and 90% [CH$_3$CN] in 3.0 min, held this mobile phase composition to 4 min and finally back to initial condition in 5 min). Purity is 90.68%, Rt=3.48 min, MS calculate: 633, MS found: 634.4 [M+H$^+$].

Example 24

[1,1,2,2,3,3-Hexadeuterio-3-(p-tolylsulfonyloxy)propyl] 2-ethyl-2-[[6-[[(1S,2S)-2-(hydroxymethyl)cyclopropyl]methoxy]-5-(3-methoxyazetidin-1-yl)pyridine-2-carbonyl]amino]butanoate

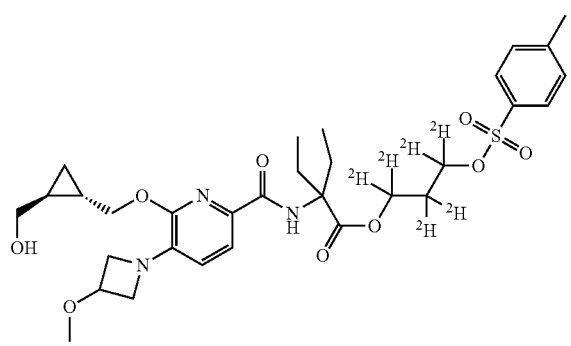 [SMILES: [2H]C([2H])(OC(=O)C(CC)(CC)NC(=O)c1ccc(N2CC(OC)C2)c(OC[C@H]2C[C@@H]2CO)n1)C([2H])([2H])C([2H])([2H])OS(=O)(=O)c1ccc(C)cc1]

a) [1,1,2,2,3,3-Hexadeuterio-3-(p-tolylsulfonyloxy)propyl] 4-methylbenzenesulfonate

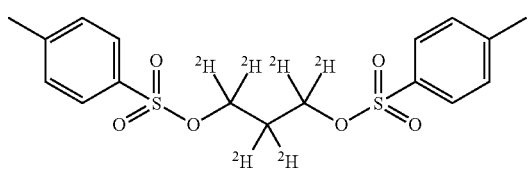

To a solution of propane-1,3-diol (d$_6$) (73 mg, 0.87 mmol) in DCM (1 mL) were added 2,6-lutidine (0.5 mL, 4.34 mmol) and tosyl chloride (496 mg, 2.6 mmol, 3 eq.). The reaction mixture was stirred for 17 h at 25° C., diluted with DCM (20 mL), washed with aq. 1 N HCl solution and water (10 mL), dried, filtered and concentrated in vacuo. The crude material was purified by flash chromatography (silica gel, 5% to 30% EtOAc in hexane) to obtain the title compound (205 mg, 61%) as white solid.
LCMS:
Column Zorbax Ext C 18 (50×4.6 mm), 5µ, (mobile phase: from 90% [10 mM NH$_4$OAc in water] and 10% [CH$_3$CN] to 70% [10 mM NH$_4$OAc in water] and 30% [CH$_3$CN] in 1.5 min, further to 10% [10 mM NH$_4$OAc in water] and 90% [CH$_3$CN] in 3.0 min, held this mobile phase composition to 4 min and finally back to initial condition in 5 min). Purity is 99.84%, Rt=3.48 min, MS calculate: 390, MS found: 408.1 [M+NH$_4^+$].

b) [1,1,2,2,3,3-Hexadeuterio-3-(p-tolylsulfonyloxy)propyl] 2-ethyl-2-[[6-[[(1S,2S)-2-(hydroxymethyl)cyclopropyl]methoxy]-5-(3-methoxyazetidin-1-yl)pyridine-2-carbonyl]amino]butanoate To a solution of 2-ethyl-2-[(6-{[(S,2S)-2-(hydroxymethyl)cyclopropyl]methoxy}-5-(3-methoxyazetidin-1-yl)pyridin-2-yl)formamido]butanoic acid (example 15 k, 50 mg, 0.12 mmol) in DMF (5.0 mL) were added K$_2$CO$_3$ (49 mg, 0.35 mmol) and [1,1,2,2,3,3-hexadeuterio-3-(p-tolylsulfonyloxy)propyl] 4-methylbenzenesulfonate (93 mg, 0.24 mmol). The reaction mixture was stirred for 17 h at 25° C., quenched with water (30 mL) and extracted with EtOAc (3×20 mL). The combined organic layers were washed with brine (20 mL), dried, filtered and concentrated in vacuo. The crude material was purified by flash chromatography (silica gel, 30% a to 80% EtOAc in hexane) to obtain the title compound (50 mg, 67%) as colorless liquid.
LCMS:
Column Zorbax Ext C 18 (50×4.6 mm), 5µ, (mobile phase: from 90% [10 mM NH$_4$OAc in water] and 10% [CH$_3$CN] to 70% [10 mM NH$_4$OAc in water] and 30% [CH$_3$CN] in 1.5 min, further to 10% [10 mM NH$_4$OAc in water] and 90% [CH$_3$CN] in 3.0 min, held this mobile phase composition to 4 min and finally back to initial condition in 5 min). Purity is 95.50%, Rt=3.47 min, MS calculate: 639, MS found: 640.3 [M+H$^+$].

Example 25

4-Fluorobutyl 2-ethyl-2-[[6-[[(1S,2S)-2-(hydroxymethyl)cyclopropyl]methoxy]-5-(3-methoxyazetidin-1-yl)pyridine-2-carbonyl]amino]butanoate

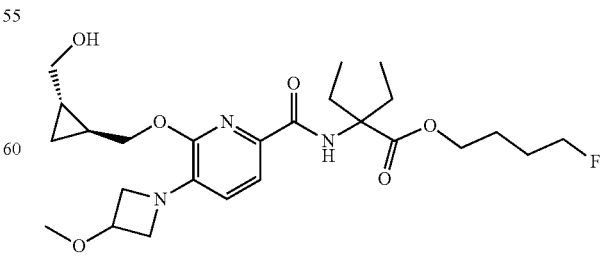

To a solution of 2-ethyl-2-[(6-{[(S,2S)-2-(hydroxymethyl)cyclopropyl]methoxy}-5-(3-methoxyazetidin-1-yl)

pyridin-2-yl)formamido]butanoic acid (example 15 k, 60 mg, 0.14 mmol) in DMF (5 mL) were added K$_2$CO$_3$ (59 mg, 0.43 mmol) and 1-bromo-4-fluorobutane (66 mg, 0.43 mmol). The reaction mixture was stirred for 2 h at 25° C., poured into water, quenched with aq. 1 N HCl solution and extracted with EtOAc (3×15 mL). The combined organic layers were washed with brine (10 mL), dried, filtered and concentrated in vacuo. The crude material was purified by flash chromatography (silica gel, 10% to 40% EtOAc in hexane) to obtain the title compound (26 mg, 37%) as colorless liquid.

LCMS:

Column Zorbax Ext C 18 (50×4.6 mm), 5μ, (mobile phase: from 90% [10 mM NH$_4$OAc in water] and 10% [CH$_3$CN] to 70% [10 mM NH$_4$OAc in water] and 30% [CH$_3$CN] in 1.5 min, further to 10% [10 mM NH$_4$OAc in water] and 90% [CH$_3$CN] in 3.0 min, held this mobile phase composition to 4 min and finally back to initial condition in 5 min). Purity is 92.73%, Rt=1.39 min, MS calculate: 495, MS found: 495.6 [M+H$^+$].

Example 26

N-[1-Ethyl-1-[[(1S)-1-(hydroxymethyl)-3-methyl-butyl]carbamoyl]propyl]-6-[[(1S,2S)-2-(hydroxymethyl)cyclopropyl]methoxy]-5-(3-methoxyazetidin-1-yl)pyridine-2-carboxamide

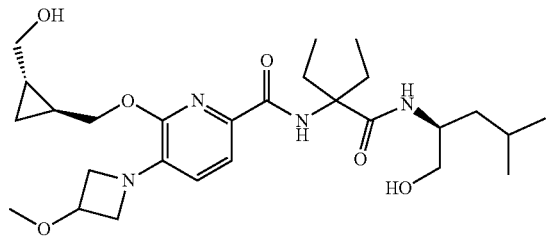 [SMILES: CCC(CC)(NC(=O)c1ccc(N2CC(OC)C2)c(OC[C@H]2C[C@@H]2CO)n1)C(=O)N[C@H](CO)CC(C)C]

To a solution of 2-ethyl-2-[(6-{[(S,2S)-2-(hydroxymethyl)cyclopropyl]methoxy}-5-(3-methoxyazetidin-1-yl)pyridin-2-yl)formamido]butanoic acid (example 15 k, 30 mg, 0.06 mmol) in DCM (5.0 mL) were added EDC.HCl (18 mg, 0.09 mmol) and HOBt (8 mg, 0.06 mmol). The reaction mixture was stirred at 25° C. for 30 min. (2S)-2-Amino-4-methylpentan-1-ol (11 mg, 0.09 mmol) and DIPEA (0.02 mL, 0.09 mmol) were added. The mixture was stirred at 25° C. for 12 h, diluted with DCM (10 mL) and washed with water (2×5 mL) and brine (5 mL). The combined extracts were dried, filtered and concentrated in vacuo. The crude material was purified by flash chromatography (silica gel, 0% to 70% EtOAc in hexane) to obtain the title compound (14 mg, 45%) as colorless sticky mass.

LCMS:

Column Zorbax Ext C 18 (50×4.6 mm), Sp, (mobile phase: from 90% [10 mM NH$_4$OAc in water] and 10% [CH$_3$CN] to 70% [10 mM NH$_4$OAc in water] and 30% [CH$_3$CN] in 1.5 min, further to 10% [10 mM NH$_4$OAc in water] and 90% [CH$_3$CN] in 3.0 min, held this mobile phase composition to 4 min and finally back to initial condition in 5 min). Purity is 78.15%, Rt=3.06 min, MS calculate: 520, MS found: 521.2 [M+H$^+$].

Example 27

N-[1-Ethyl-1-[[(1S)-1-(hydroxymethyl)-3-methyl-butyl]carbamoyl]propyl]-5-(3-fluoroazetidin-1-yl)-6-[[(1R,2R)-2-(hydroxymethyl)cyclopropyl]methoxy]pyridine-2-carboxamide or N-[1-ethyl-1-[[(1S)-1-(hydroxymethyl)-3-methyl-butyl]carbamoyl]propyl]-5-(3-fluoroazetidin-1-yl)-6-[[(1S,2S)-2-(hydroxymethyl)cyclopropyl]methoxy]pyridine-2-carboxamide

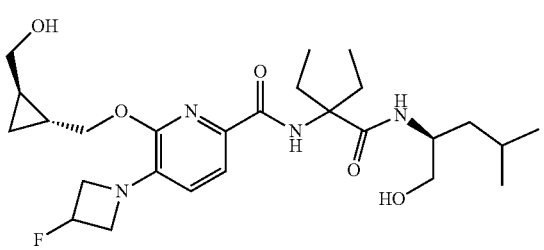 [SMILES: CCC(CC)(NC(=O)c1ccc(N2CC(F)C2)c(OC[C@@H]2C[C@H]2CO)n1)C(=O)N[C@H](CO)CC(C)C]

a) (Rac)-trans-ethyl 2-[(6-{[-2-[(benzyloxy)methyl]cyclopropyl]methoxy}-5-(3-fluoroazetidin-1-yl)pyridin-2-yl) formamido]-2-ethylbutanoate

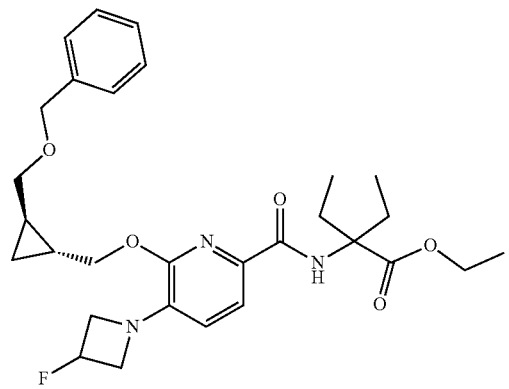 [SMILES: CCOC(=O)C(CC)(CC)NC(=O)c1ccc(N2CC(F)C2)c(OC[C@@H]2C[C@H]2COCc2ccccc2)n1]

To a solution of (rac)-trans-ethyl 2-[(6-{[-2-[(benzyloxy)methyl]cyclopropyl]methoxy}-5-bromopyridin-2-yl)formamido]-2-ethylbutanoate (example 22 b, 250 mg, 0.47 mmol) in toluene (12 mL) were added 3-fluorozetidine hydrochloride (78 mg, 0.70 mmol) and cesium carbonate (458 mg, 1.41 mmol). The mixture was degassed with argon for 10 minutes. Rac-BINAP (58 mg, 0.09 mmol) and Pd(II) acetate (21 mg, 0.09 mmol) were added and the mixture was heated to 110° C. for 3 h. The reaction mixture was diluted with EtOAc (30 mL), filtered through a celite bed and the bed was washed with EtOAc (30 mL). The filtrate was concentrated in vacuo. The crude material was purified by flash chromatography (silica gel, 10% to 20% EtOAc in hexane) to obtain the title compound (205 mg, 83%) as brown liquid.
LCMS:
Column Zorbax Ext C 18 (50×4.6 mm), 5μ, (mobile phase: from 90% [10 mM NH₄OAc in water] and 10% [CH₃CN] to 70% [10 mM NH₄OAc in water] and 30% [CH₃CN] in 1.5 min, further to 10% [10 mM NH₄OAc in water] and 90% [CH₃CN] in 3.0 min, held this mobile phase composition to 4 min and finally back to initial condition in 5 min). Purity is 98.26%, Rt=4.21 min, MS calculate: 527, MS found: 527.9 [M+H⁺].

b) (Rac)-trans-2-[(6-{[-2-[(benzyloxy)methyl]cyclopropyl]methoxy}-5-(3-fluoroazetidin-1-yl)pyridin-2-yl) formamido]-2-ethylbutanoic Acid

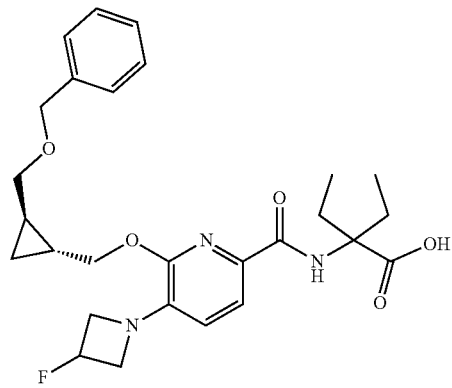 [SMILES: CCC(CC)(NC(=O)c1ccc(N2CC(F)C2)c(OC[C@@H]2C[C@H]2COCc2ccccc2)n1)C(=O)O]

In a 25 mL round-bottomed flask (rac)-trans-ethyl 2-[(6-{[-2-[(benzyloxy)methyl]cyclopropyl]methoxy}-5-(3-fluoroazetidin-1-yl) pyridin-2-yl) formamido]-2-ethylbutanoate (290 mg, 0.55 mmol) was combined with THF (2.5 mL), MeOH (2.8 mL) and water (2.5 mL) to give a light yellow solution. KOH pellets (154 mg, 2.75 mmol) were added. The mixture was heated to 90° C. for 18 h. The organic solvent was removed under reduced pressure. The aqueous phase was diluted with water (30 mL) and extracted with diethyl ether (2×10 mL). The organic part was discarded, the aqueous phase was adjusted to pH~2 (1 M HCl) and extracted with EtOAc (3×25 mL). The combined organic layers were washed with brine (1×20 mL), dried, filtered and concentrated in vacuo to obtain the title compound (260 mg, 95%) as brown sticky mass.
LCMS:
Column Zorbax Ext C 18 (50×4.6 mm), 5μ, (mobile phase: from 90% [10 mM NH₄OAc in water] and 10% [CH₃CN] to 70% [10 mM NH₄OAc in water] and 30% [CH₃CN] in 1.5 min, further to 10% [10 mM NH₄OAc in water] and 90% [CH₃CN] in 3.0 min, held this mobile phase composition to 4 min and finally back to initial condition in 5 min). Purity is 100%, Rt=2.70 min, MS calculate: 497, MS found: 498.4 [M+H⁺].

c) trans-2-[(6-{[-2-[(Benzyloxy)methyl]cyclopropyl]methoxy}-5-(3-fluoroazetidin-1-yl)pyridin-2-yl) formamido]-2-ethyl-N-[(2S)-1-hydroxy-4-methylpentan-2-yl]butanamide

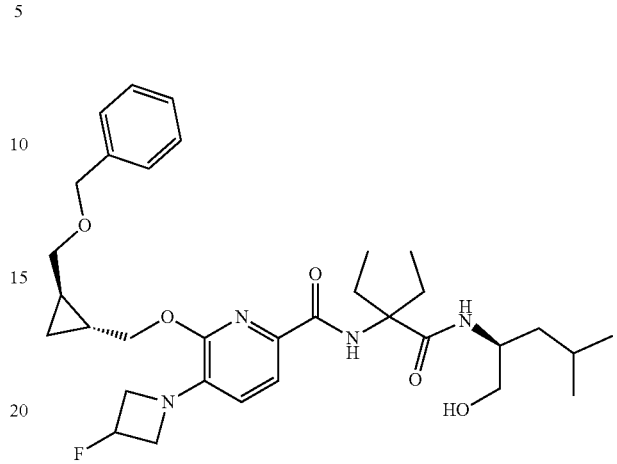

To a solution of (rac)-trans-2-[(6-{[-2-[(benzyloxy)methyl]cyclopropyl]methoxy}-5-(3-fluoroazetidin-1-yl) pyridin-2-yl) formamido]-2-ethylbutanoic acid (180 mg, 0.36 mmol) in DCM (12 mL) were added EDC.HCl (104 mg, 0.54 mmol) and HOBt (49 mg, 0.36 mmol). The reaction mixture was stirred at 25° C. for 30 min. (S)-2-Amino-4-methyl-pentan-1-ol (63 mg, 0.54 mmol) and DIPEA (0.09 mL, 0.54 mmol) were added. The mixture was stirred at 25° C. for 12 h, diluted with DCM (30 mL) and washed with water (20 mL) and brine (10 mL). The combined extracts were dried, filtered and concentrated in vacuo. The crude material was purified by flash chromatography (silica gel, 0% to 70% EtOAc in hexane) to obtain the title compound (160 mg, 74%) as sticky solid.
LCMS:
Column Zorbax Ext C 18 (50×4.6 mm), 5μ, (mobile phase: from 90% [10 mM NH₄OAc in water] and 10% [CH₃CN] to 70% [10 mM NH₄OAc in water] and 30% [CH₃CN] in 1.5 min, further to 10% [10 mM NH₄OAc in water] and 90% [CH₃CN] in 3.0 min, held this mobile phase composition to 4 min and finally back to initial condition in 5 min). Purity is 89.65%, Rt=3.77 min, MS calculate: 598, MS found: 599.1 [M+H⁺].

d) N-[1-Ethyl-1-[[(1S)-1-(hydroxymethyl)-3-methylbutyl]carbamoyl]propyl]-5-(3-fluoroazetidin-1-yl)-6-[[(1R,2R)-2-(hydroxymethyl)cyclopropyl]methoxy]pyridine-2-carboxamide or N-[1-ethyl-1-[[(1S)-1-(hydroxymethyl)-3-methyl-butyl]carbamoyl]propyl]-5-(3-fluoroazetidin-1-yl)-6-[[(1S,2S)-2-(hydroxymethyl)cyclopropyl]methoxy]pyridine-2-carboxamide A solution of trans-2-[(6-{[-2-[(benzyloxy)methyl]cyclopropyl]methoxy}-5-(3-fluoroazetidin-1-yl)pyridin-2-yl) formamido]-2-ethyl-N-[(2S)-1-hydroxy-4-methylpentan-2-yl] butanamide (160 mg, 0.27 mmol) in EtOAc (6 mL) and methanol (0.6 mL) was degassed for 10 minutes. Pd—C (10%) (80 mg) was added and degassing was continued for another 2 minutes. The mixture was then put under a hydrogen atmosphere at balloon pressure and stirred for 17 h at 25° C., filtered through a celite bed and concentrated in vacuo to get crude trans-2-ethyl-2-{[5-(3-fluoroazetidin-1-yl)-6-{[-2-(hydroxymethyl)cyclopropyl]methoxy}pyridin- 2-yl] formamido}-N-[(2S)-1-hydroxy-4-methylpentan-2-yl] butanamide (130 mg, 86%) as colorless gum. The crude was purified by preparative chiral HPLC (column: Chiralpak IE (250×4.6 mm), Si; mobile phase: hexane/EtOH/DEA: 90/10/0.1; flow rate: 1.0 mL/min) to obtain the title compound (27 mg, 20/a, 100% ee).
LCMS:
Column Zorbax Ext C 18 (50×4.6 mm), 5μ, (mobile phase: from 90% [10 mM NH$_4$OAc in water] and 10% [CH$_3$CN] to 70% [10 mM NH$_4$OAc in water] and 30% [CH$_3$CN] in 1.5 min, further to 10% [10 mM NH$_4$OAc in water] and 90% [CH$_3$CN] in 3.0 min, held this mobile phase composition to 4 min and finally back to initial condition in 5 min). Purity is 97.62%, Rt=3.09 min, MS calculate: 508, MS found: 509.1 [M+H$^+$].

Example 28

N-[1-Ethyl-1-[[(1S)-1-(hydroxymethyl)-3-methyl-butyl]carbamoyl]propyl]-5-(3-fluoroazetidin-1-yl)-6-[[(1S,2S)-2-(hydroxymethyl)cyclopropyl]methoxy] pyridine-2-carboxamide or N-[1-ethyl-1-[[(1S)-1-(hydroxymethyl)-3-methyl-butyl]carbamoyl]propyl]-5-(3-fluoroazetidin-1-yl)-6-[[(1R,2R)-2-(hydroxymethyl)cyclopropyl]methoxy]pyridine-2-carboxamide

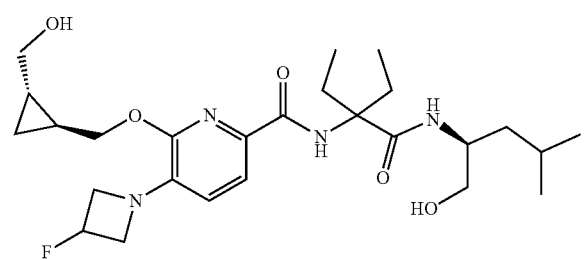 [SMILES: CCC(CC)(NC(=O)c1ccc(N2CC(F)C2)c(OC[C@H]2C[C@@H]2CO)n1)C(=O)N[C@H](CO)CC(C)C]

A solution of trans-2-[(6-{[-2-[(benzyloxy)methyl]cyclopropyl]methoxy}-5-(3-fluoroazetidin-1-yl)pyridin-2-yl) formamido]-2-ethyl-N-[(2S)-1-hydroxy-4-methylpentan-2-yl] butanamide (160 mg, 0.27 mmol) in EtOAc (6 mL) and methanol (0.6 mL) was degassed for 10 minutes. Pd—C (10%) (80 mg) was added and degassing was continued for another 2 minutes. The mixture was then put under a hydrogen atmosphere at balloon pressure and stirred for 17 h at 25° C., filtered through a celite bed and concentrated in vacuo to get crude trans-2-ethyl-2-{[5-(3-fluoroazetidin-1-yl)-6-{[-2-(hydroxymethyl)cyclopropyl]methoxy}pyridin-2-yl] formamido}-N-[(2S)-1-hydroxy 4-methylpentan-2-yl] butanamide (130 mg, 86%) as colorless gum. The crude was purified by preparative chiral HPLC (column: Chiralpak IE (250×4.6 mm), 51; mobile phase: hexane/EtOH/DEA: 90/10/0.1; flow rate: 1.0 mL/min) to obtain the title compound (27 mg, 20%, 89% ee).
LCMS:
Column Zorbax Ext C 18 (50×4.6 mm), 5μ, (mobile phase: from 90% [10 mM NH$_4$OAc in water] and 10% [CH$_3$CN] to 70% [10 mM NH$_4$OAc in water] and 30% [CH$_3$CN] in 1.5 min, further to 10% [10 mM NH$_4$OAc in water] and 90% [CH$_3$CN] in 3.0 min, held this mobile phase composition to 4 min and finally back to initial condition in 5 min). Purity is 95.79%, Rt=3.09 min, MS calculate: 508, MS found: 509.3 [M+H$^+$].

Example 29

3-Fluoropropyl 2-ethyl-2-{[5-(3-fluoroazetidin-1-yl)-6-{[(1R,2R)-2-(hydroxymethyl)cyclopropyl] methoxy}pyridin-2-yl]formamido}butanoate or 3-fluoropropyl 2-ethyl-2-{[5-(3-fluoroazetidin-1-yl)-6-{[(1S,2S)-2-(hydroxymethyl)cyclopropyl] methoxy}pyridin-2-yl]formamido}butanoate

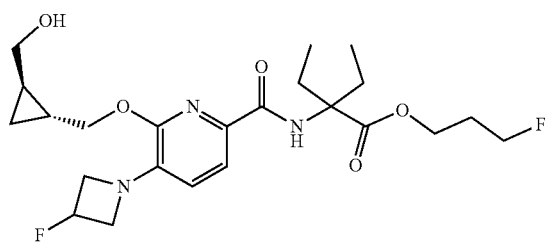 [SMILES: CCC(CC)(NC(=O)c1ccc(N2CC(F)C2)c(OC[C@@H]2C[C@H]2CO)n1)C(=O)OCCCF]

a) (Rac)-trans-3-fluoropropyl 2-[(6-{[-2-[(benzyloxy)methyl]cyclopropyl]methoxy}-5-(3-fluoroazetidin-1-yl)pyridin-2-yl)formamido]-2-ethylbutanoate

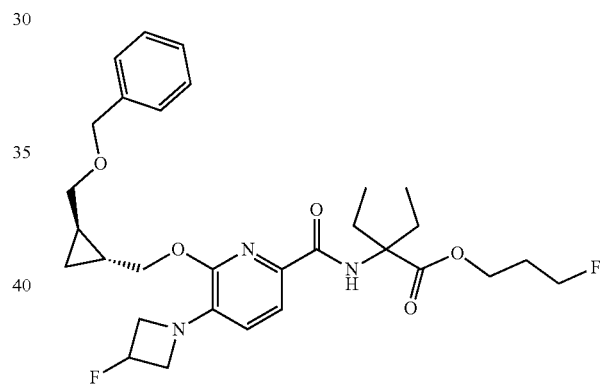

To a solution of (rac)-trans-2-[(6-{[-2-[(benzyloxy)methyl]cyclopropyl]methoxy}-5-(3-fluoroazetidin-1-yl) pyridin-2-yl)formamido]-2-ethylbutanoic acid (example 27 b, 170 mg, 0.34 mmol) in DMF (10 mL) were added K$_2$CO$_3$ (141 mg, 1.02 mmol) and 1-fluoro-3-iodo-propane (192 mg, 1.02 mmol). The mixture was stirred for 2 h at 25° C., diluted with water (100 mL) and extracted with EtOAc (3×50 mL). The combined organic layers were washed with brine (30 mL), dried, filtered and concentrated in vacuo to obtain the title compound (170 mg) as yellow gum which was used in the next reaction step without further purification.
LCMS:
Column Zorbax Ext C 18 (50×4.6 mm), 5μ, (mobile phase: from 90% [10 mM NH$_4$OAc in water] and 10% [CH$_3$CN] to 70% [10 mM NH$_4$OAc in water] and 30% [CH$_3$CN] in 1.5 min, further to 10% [10 mM NH$_4$OAc in water] and 90% [CH$_3$CN] in 3.0 min, held this mobile phase composition to 4 min and finally back to initial condition in 5 min). Purity is 63.82%, Rt=4.02 min, MS calculate: 559, MS found: 560.1 [M+H$^+$].

b) 3-Fluoropropyl 2-ethyl-2-{[5-(3-fluoroazetidin-1-yl)-6-{[(1R,2R)-2-(hydroxymethyl)cyclopropyl]methoxy}pyridin-2-yl]formamido}butanoate or 3-fluoropropyl 2-ethyl-2-{[5-(3-fluoroazetidin-1-yl)-6-{[(1S,2S)-2-(hydroxymethyl)cyclopropyl]methoxy}pyridin-2-yl]formamido}butanoate A solution of (rac)-trans-3-fluoropropyl 2-[(6-{[-2-[(benzyloxy)methyl]cyclopropyl]methoxy}-5-(3-fluoroazetidin-1-yl)pyridin-2-yl)formamido]-2-ethylbutanoate (160 mg, 0.29 mmol) in EtOAc (6 mL) and methanol (0.6 mL) was degassed for 10 minutes. Pd—C (10%, 80 mg) was added and degassing was continued for another 2 minutes. The mixture was put under a hydrogen atmosphere at balloon pressure and stirred for 17 h at 25° C. The reaction mixture was filtered through a celite bed and concentrated in vacuo to get crude (rac)-trans-3-fluoropropyl 2-ethyl-2-{[5-(3-fluoroazetidin-1-yl)-6-{[-2-(hydroxymethyl) cyclopropyl]methoxy}pyridin-2-yl]formamido}butanoate (140 mg) as colorless gum. The crude was purified by preparative chiral HPLC (column: Chiralpak IC (250×4.6 mm), 51; mobile phase: hexane/EtOH/isopropylamine: 80/20/0.1; flow rate: 1.0 mL/min) to obtain the title compound (34 mg, 24%) as colorless sticky mass.

LCMS:

Column Zorbax Ext C 18 (50×4.6 mm), 5μ, (mobile phase: from 90% [10 mM NH₄OAc in water] and 10% [CH₃CN] to 70% [10 mM NH₄OAc in water] and 30% [CH₃CN] in 1.5 min, further to 10% [10 mM NH₄OAc in water] and 90% [CH₃CN] in 3.0 min, held this mobile phase composition to 4 min and finally back to initial condition in 5 min). Purity is 98.47%, Rt=3.26 min, MS calculate: 469, MS found: 470.1 [M+H⁺].

Example 30

3-Fluoropropyl 2-ethyl-2-{[5-(3-fluoroazetidin-1-yl)-6-{[(1S,2S)-2-(hydroxymethyl)cyclopropyl]methoxy}pyridin-2-yl]formamido}butanoate or 3-fluoropropyl 2-ethyl-2-{[5-(3-fluoroazetidin-1-yl)-6-{[(1R,2R)-2-(hydroxymethyl)cyclopropyl]methoxy}pyridin-2-yl]formamido}butanoate

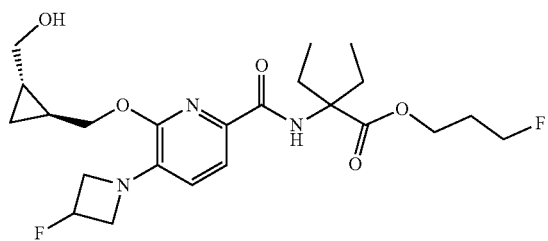 [SMILES: CCC(CC)(NC(=O)c1ccc(N2CC(F)C2)c(OC[C@H]2C[C@@H]2CO)n1)C(=O)OCCCF]

A solution of (rac)-trans-3-fluoropropyl 2-[(6-[{-2-[(benzyloxy)methyl]cyclopropyl]methoxy}-5-(3-fluoroazetidin-1-yl)pyridin-2-yl)formamido]-2-ethylbutanoate (160 mg, 0.29 mmol) in EtOAc (6 mL) and methanol (0.6 mL) was degassed for 10 minutes. Pd—C (10%, 80 mg) was added and degassing was continued for another 2 minutes. The mixture was put under a hydrogen atmosphere at balloon pressure and stirred for 17 h at 25° C. The reaction mixture was filtered through a celite bed and concentrated in vacuo to get crude (rac)-trans-3-fluoropropyl 2-ethyl-2-{[5-(3-fluoroazetidin-1-yl)-6-{[-2-(hydroxymethyl) cyclopropyl]methoxy}pyridin-2-yl]formamido}butanoate (140 mg) as colorless gum. The crude was purified by preparative chiral HPLC (column: Chiralpak IC (250×4.6 mm), 51; mobile phase: hexane/EtOH/isopropylamine: 80/20/0.1; flow rate: 1.0 mL/min) to obtain the title compound (37 mg, 26%) as colorless sticky mass.

LCMS:

Column Zorbax Ext C 18 (50×4.6 mm), 5μ, (mobile phase: from 90% [10 mM NH₄OAc in water] and 10% [CH₃CN] to 70% [10 mM NH₄OAc in water] and 30% [CH₃CN] in 1.5 min, further to 10% [10 mM NH₄OAc in water] and 90% [CH₃CN] in 3.0 min, held this mobile phase composition to 4 min and finally back to initial condition in 5 min). Purity is 98.46%, Rt=3.28 min, MS calculate: 469, MS found: 470.1 [M+H⁺].

Example 31

(Rac)-trans-3-fluoropropyl 2-ethyl-2-[[6-[[-2-(hydroxymethyl)cyclopropyl]methoxy]-5-[3-(p-tolylsulfonyloxy)azetidin-1-yl]pyridine-2-carbonyl]amino]butanoate

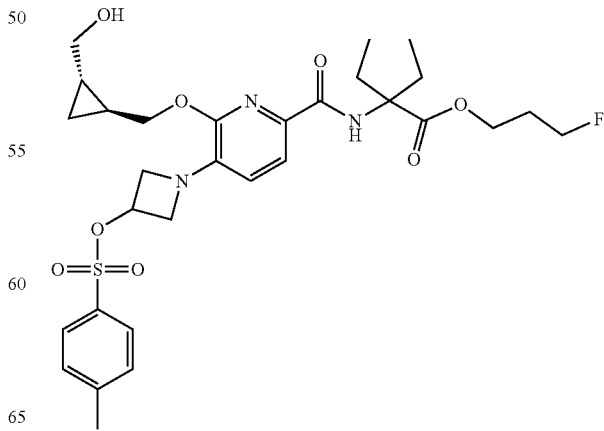

a) (Rac)-trans-3-fluoropropyl 2-[(6-{[-2-[(benzyloxy)methyl] cyclopropyl]methoxy}-5-(3-{[(4-methylbenzene)sulfonyl]oxy}azetidin-1-yl)pyridin-2-yl)formamido]-2-ethylbutanoate

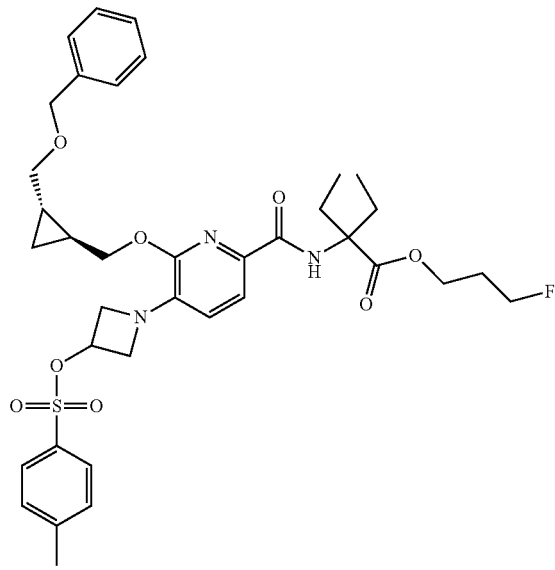 [SMILES: CCC(CC)(NC(=O)c1ccc(N2CC(OS(=O)(=O)c3ccc(C)cc3)C2)c(OC[C@H]2C[C@@H]2COCc2ccccc2)n1)C(=O)OCCCF]

To a solution of (rac)-trans-3-fluoropropyl 2-[(6-{[-2-[(benzyloxy)methyl]cyclopropyl]methoxy}-5-(3-hydroxyazetidin-1-yl)pyridin-2-yl)formamido]-2-ethylbutanoate (example 22 e, 225 mg, 0.40 mmol) in DCM (5 mL) in a sealed tube were added 2,6-lutidine (0.25 mL, 2.02 mmol) and tosyl chloride (230 mg, 1.21 mmol). The reaction mixture was stirred for 16 h at 50° C., diluted with DCM (20 mL) and washed with aq. 1 N HCl and water (10 mL). The organic layer was dried, filtered and concentrated in vacuo. The crude purified by prep. HPLC to obtain the title compound as yellowish solid (16 mg, 6%).

LCMS:
Column Zorbax Ext C 18 (50×4.6 mm), 5µ, (mobile phase: from 90/a [10 mM NH₄OAc in water] and 10% [CH₃CN] to 70% [10 mM NH₄OAc in water] and 30% [CH₃CN] in 1.5 min, further to 10% [10 mM NH₄OAc in water] and 90% [CH₃CN] in 3.0 min, held this mobile phase composition to 4 min and finally back to initial condition in 5 min). Purity:crude material, Rt=2.44 min, MS calculate: 711, MS found: 712.5 [M+H⁺].

b) (Rac)-trans-3-fluoropropyl 2-ethyl-2-[[6-[[-2-(hydroxymethyl)cyclopropyl]methoxy]-5-[3-(p-tolylsulfonyloxy)azetidin-1-yl]pyridine-2-carbonyl]amino]butanoate A solution of (rac)-trans-3-fluoropropyl 2-[(6-{[-2-[(benzyloxy)methyl]cyclopropyl]methoxy}-5-(3-{[(4-methylbenzene)sulfonyl]oxy}azetidin-1-yl)pyridin-2-yl)formamido]-2-ethylbutanoate (16.0 mg, 0.02 mmol) in EtOAc (2 mL) was degassed. Pd/C (10 wt %, 8.0 mg) was added. The mixture was degassed, charged with H₂, and stirred for 16 h at ambient temperature. The mixture was filtered through celite and the celite bed was washed with EtOAc. The filtrate was dried over anhydrous Na₂SO₄, filtered and concentrated in vacuo to yield the title compound (10.1 mg, 72%) as colourless sticky mass.

LCMS:
Column Zorbax Ext C 18 (50×4.6 mm), 5µ, (mobile phase: from 90% [10 mM NH₄OAc in water] and 10% [CH₃CN] to 70% [10 mM NH₄OAc in water] and 30% [CH₃CN] in 1.5 min, further to 10% [10 mM NH₄OAc in water] and 90% [CH₃CN] in 3.0 min, held this mobile phase composition to 4 min and finally back to initial condition in 5 min). Purity is 89.55%, Rt=3.53 min, MS calculate: 621, MS found: 622.2 [M+H⁺].

Example 32

3-Fluoropropyl 2-[[6-[[(1S,2S)-2-(benzyloxymethyl)cyclopropyl]methoxy]-5-(3-methoxyazetidin-1-yl)pyridine-2-carbonyl]amino]-2-ethyl-butanoate

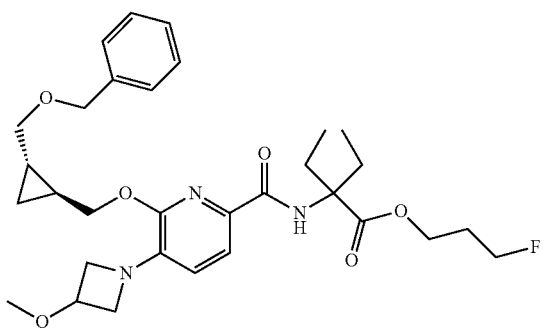 [SMILES: CCC(CC)(NC(=O)c1ccc(N2CC(OC)C2)c(OC[C@H]2C[C@@H]2COCc2ccccc2)n1)C(=O)OCCCF]

a) 2-[(6-{[(1S,2S)-2-[(Benzyloxy)methyl]cyclopropyl]methoxy}-5-(3-methoxyazetidin-1-yl)pyridin-2-yl)formamido]-2-ethylbutanoic Acid

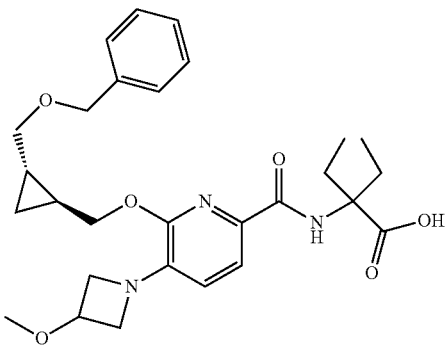 [SMILES: CCC(CC)(NC(=O)c1ccc(N2CC(OC)C2)c(OC[C@H]2C[C@@H]2COCc2ccccc2)n1)C(=O)O]

To a solution of 3-fluoropropyl 2-ethyl-2-[(6-{[(1S,2S)-2-(hydroxymethyl)cyclopropyl]methoxy}-5-(3-methoxyazetidin-1-yl)pyridin-2-yl)formamido]butanoate (example 15 m, 20 mg, 0.04 mmol) in DMF (1.0 mL) was added benzyl bromide (7 mg, 0.04 mmol). The mixture was cooled to 0° C. and put under an argon atmosphere. Sodium hydride (3 mg, 0.08 mmol) was added. The reaction mixture was stirred at ambient temperature for 15 h, poured onto water (10 mL), acidified with aqueous HCl and extracted with EtOAc (3×10 mL). The combined organic layers were washed with brine (10 mL), dried, filtered and concentrated in vacuo to obtain the title compound (20 mg, 94%) as yellow sticky mass.

LCMS:

Column Zorbax Ext C 18 (50×4.6 mm), 5μ, (mobile phase: from 90% [10 mM NH₄OAc in water] and 10% [CH₃CN] to 70% [10 mM NH₄OAc in water] and 30% [CH₃CN] in 1.5 min, further to 10/a [10 mM NH₄OAc in water] and 90% [CH₃CN] in 3.0 min, held this mobile phase composition to 4 min and finally back to initial condition in 5 min). Purity is 84.14%, Rt=0.54 min, MS calculate: 511, MS found: 512.0 [M+H⁺].

b) 3-Fluoropropyl 2-[[6-[[(1S,2S)-2-(benzyloxymethyl)cyclopropyl]methoxy]-5-(3-methoxyazetidin-1-yl)pyridine-2-carbonyl]amino]-2-ethyl-butanoate To a solution of 2-[(6-{[(1S,2S)-2-[(benzyloxy)methyl]cyclopropyl]methoxy}-5-(3-methoxyazetidin-1-yl)pyridin-2-yl)formamido]-2-ethylbutanoic acid (20 mg, 0.04 mmol) in DMF (1.0 mL) were added K₂CO₃ (16 mg, 0.12 mmol) and 1-iodo-3-fluoro-propane (22 mg, 0.12 mmol). The reaction mixture was stirred for 2 h at 25° C., poured onto water and quenched with aq. 1 N HCl solution and extracted with EtOAc (3×15 mL). The combined extracts were washed with brine (10 mL), dried, filtered and concentrated in vacuo. The crude was purified by preparative TLC (20% EtOAc in hexane) to obtain the title compound (11 mg, 49%) as colorless liquid.

LCMS:

Column Zorbax Ext C 18 (50×4.6 mm), 5μ, (mobile phase: from 90% [10 mM NH₄OAc in water] and 10% [CH₃CN] to 70% [10 mM NH₄OAc in water] and 30% [CH₃CN] in 1.5 min, further to 10% [10 mM NH₄OAc in water] and 90% [CH₃CN] in 3.0 min, held this mobile phase composition to 4 min and finally back to initial condition in 5 min). Purity is 98.02%, Rt=4.07 min, MS calculate: 571, MS found: 572.1 [M+H⁺].

Example 33

Fluoromethyl 2-ethyl-2-[[6-[[3-(hydroxymethyl)oxetan-3-yl]methoxy]-5-pyrrolidin-1-yl-pyridine-2-carbonyl]amino]butanoate

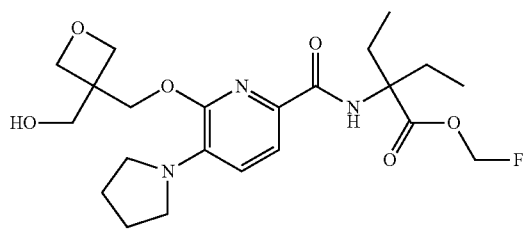 [SMILES: CCC(CC)(NC(=O)c1ccc(N2CCCC2)c(OCC2(CO)COC2)n1)C(=O)OCF]

a) Methyl 6-((3-((benzyloxy)methyl)oxetan-3-yl)methoxy)-5-bromopicolinate

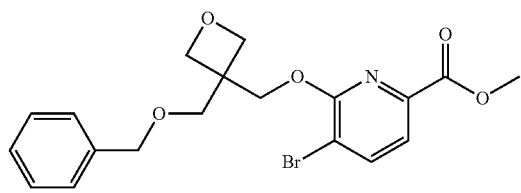 [SMILES: COC(=O)c1ccc(Br)c(OCC2(COCc3ccccc3)COC2)n1]

In a 250 mL three-necked flask, 5-bromo-6-chloropicolinic acid (CAN 959958-25-9, 1.8 g, 7.61 mmol, Eq: 1) was combined with DMF (100 mL) to give a colorless solution. The mixture was cooled to 0° C. and sodium hydride (913 mg, 22.8 mmol, Eq: 3) was added. The reaction mixture was stirred at 0° C. for 20 min. In a 10 mL round-bottomed flask, (3-((benzyloxy)methyl)oxetan-3-yl)methanol (CAN 142731-84-8, 2.06 g, 9.9 mmol, Eq: 1.3) was combined with DMF (10 mL) to give a colorless solution, which was slowly added to the reaction mixture. The reaction mixture was heated to 80° C. for 4 h and cooled to ambient temperature. Methyl iodide (3.24 g, 1.43 mL, 22.8 mmol, Eq: 3) was added and stirring was continued for 18 h. The solvent was removed under reduced pressure. The residue was diluted with EtOAc (100 mL) and water (100 mL). The layers were separated and the aqueous phase was extracted with EtOAc (2×40 mL). The combined organic layers were washed with brine (1×100 mL), dried over Na₂SO₄, filtered and brought to dryness under reduced pressure. The crude product was purified by column chromatography (SiO₂, 50 g, hept./EtOAc) to give the title compound (2.82 g, 88%) as colorless oil, MS (ISP): 424.121 [MH⁺].

b) Methyl 6-((3-((benzyloxy)methyl)oxetan-3-yl)methoxy)-5-(pyrrolidin-1-yl)picolinate

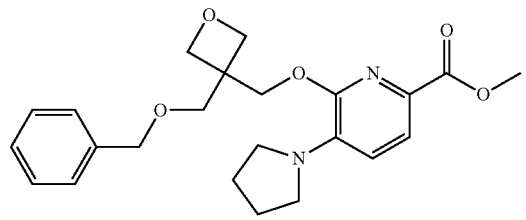 [SMILES: COC(=O)c1ccc(N2CCCC2)c(OCC2(COCc3ccccc3)COC2)n1]

In analogy to the procedure described in example 1 c, methyl 6-((3-((benzyloxy)methyl)oxetan-3-yl)methoxy)-5-bromopicolinate was reacted with pyrrolidine to give the title compound as light brown oil, MS (ISP): 413.365 [MH⁺].

c) 6-((3-((Benzyloxy)methyl)oxetan-3-yl)methoxy)-5-(pyrrolidin-1-yl)picolinic acid

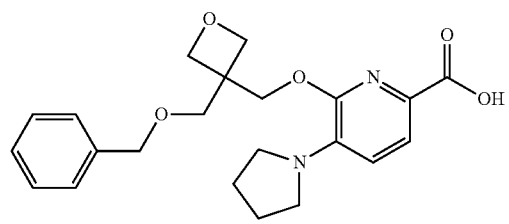 [SMILES: O=C(O)c1ccc(N2CCCC2)c(OCC2(COCc3ccccc3)COC2)n1]

In analogy to the procedure described in example 11 a, methyl 6-((3-((benzyloxy)methyl)oxetan-3-yl)methoxy)-5-(pyrrolidin-1-yl)picolinate was hydrolyzed with KOH to give the title compound as white solid which was used in the next reaction step without further purification, MS (ISP): 399.305 [MH⁺].

d) Ethyl 2-(6-((3-((benzyloxy)methyl)oxetan-3-yl)methoxy)-5-(pyrrolidin-1-yl)picolinamido)-2-ethylbutanoate

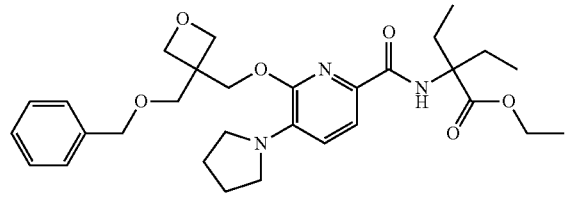 [SMILES: CCOC(=O)C(CC)(CC)NC(=O)c1ccc(N2CCCC2)c(OCC2(COCc3ccccc3)COC2)n1]

In a 25 mL round-bottomed flask, 6-((3-((benzyloxy)methyl)oxetan-3-yl)methoxy)-5-(pyrrolidin-1-yl)picolinic acid (660 mg, 1.66 mmol, Eq: 1) was combined with DMF (10 mL) to give a light yellow solution. TBTU (532 mg, 1.66 mmol, Eq: 1) and DIPEA (856 mg, 1.16 mL, 6.63 mmol, Eq: 4) were added. Ethyl 2-amino-2-ethylbutanoate hydrochloride (CAN 1135219-29-2, 389 mg, 1.99 mmol, Eq: 1.2) was added and the reaction mixture was stirred at ambient temperature for 17 h. Additional 0.12 equivalents of ethyl 2-amino-2-ethylbutanoate hydrochloride and 0.1 equivalents of TBTU were added and stirring was continued for 2 h. The reaction mixture was diluted with EtOAc and washed with sat. NaHCO$_3$ (3×25 mL), 1 M HCl (3×25 mL) and sat. NaCl (1×25 mL). The organic layer was dried over Na$_2$SO$_4$ and concentrated in vacuo. The crude product was purified by column chromatography (SiO$_2$, 50 g, hept./EtOAc) to give the title compound (587 mg, 66%) as colorless oil, MS (ISP): 540.432 [MH$^+$].

e) Ethyl 2-ethyl-2-(6-((3-(hydroxymethyl)oxetan-3-yl)methoxy)-5-(pyrrolidin-1-yl)picolinamido)butanoate

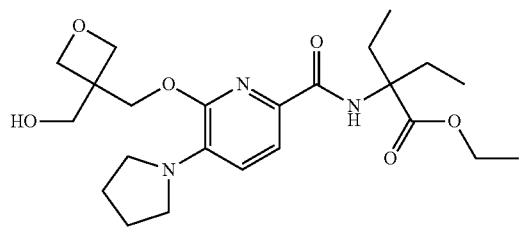 [SMILES: CCOC(=O)C(CC)(CC)NC(=O)c1ccc(N2CCCC2)c(OCC2(CO)COC2)n1]

In a 25 mL round-bottomed flask, ethyl 2-(6-((3-((benzyloxy)methyl)oxetan-3-yl)methoxy)-5-(pyrrolidin-1-yl)picolinamido)-2-ethylbutanoate (556 mg, 1.03 mmol, Eq: 1) was combined with ethyl acetate (5 mL) and MeOH (5 mL) to give a colorless solution. Pd/C (250 mg, 235 µmol, Eq: 0.228) was added and the reaction mixture was stirred under and atmosphere of hydrogen gas for 44 h. Another portion of Pd/C (200 mg) was added and stirring was continued under an atmosphere of hydrogen gas for 16 h. The mixture was filtered through Celite and the organic solvent was removed under reduced pressure to give the title compound (370 mg, 80%) as white solid, MS (ISP): 450.3% [MH$^+$].

f) 2-Ethyl-2-(6-((3-(hydroxymethyl)oxetan-3-yl)methoxy)-5-(pyrrolidin-1-yl)picolinamido)butanoic Acid

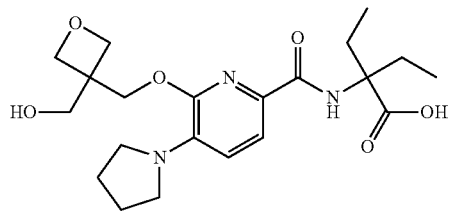 [SMILES: CCC(CC)(NC(=O)c1ccc(N2CCCC2)c(OCC2(CO)COC2)n1)C(=O)O]

In analogy to the procedure described in example 11 a, ethyl 2-ethyl-2-(6-((3-(hydroxymethyl)oxetan-3-yl)methoxy)-5-(pyrrolidin-1-yl)picolinamido)butanoate was hydrolyzed with KOH to give the title compound as brown oil which was used in the next reaction step without further purification.

g) Fluoromethyl 2-ethyl-2-[[6-[[3-(hydroxymethyl)oxetan-3-yl]methoxy]-5-pyrrolidin-1-yl-pyridine-2-carbonyl]amino]butanoate In analogy to the procedure described in example 11 b, 2-ethyl-2-(6-((3-(hydroxymethyl)oxetan-3-yl)methoxy)-5-(pyrrolidin-1-yl)picolinamido)butanoic acid was reacted with fluoro-iodo-methane to give the title compound as colorless oil, MS (ESI): 454.4 [MH$^+$].

Example 34

2-Fluoroethyl 2-ethyl-2-(6-((3-(hydroxymethyl)oxetan-3-yl)methoxy)-5-(pyrrolidin-1-yl)picolinamide)butanoate

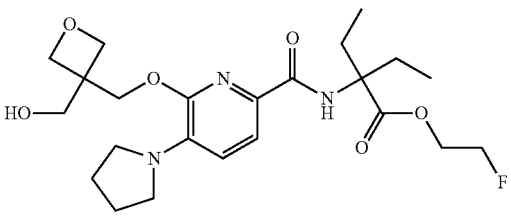 [SMILES: CCC(CC)(NC(=O)c1ccc(N2CCCC2)c(OCC2(CO)COC2)n1)C(=O)OCCF]

In analogy to the procedure described in example 11 b, 2-ethyl-2-(6-((3-(hydroxymethyl)oxetan-3-yl)methoxy)-5-(pyrrolidin-1-yl)picolinamido)butanoic acid (example 33 f) was reacted with 1-fluoro-2-iodoethane to give the title compound as colorless oil, MS (ESI): 468.4 [MH$^+$].

Example 35

3-Fluoropropyl 2-ethyl-2-(6-((3-(hydroxymethyl)oxetan-3-yl)methoxy)-5-(pyrrolidin-1-yl)picolinamido)butanoate

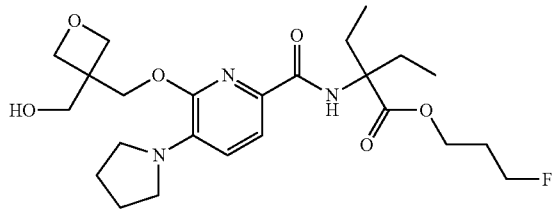 [SMILES: CCC(CC)(NC(=O)c1ccc(N2CCCC2)c(OCC2(CO)COC2)n1)C(=O)OCCCF]

In analogy to the procedure described in example 11 b, 2-ethyl-2-(6-((3-(hydroxymethyl)oxetan-3-yl)methoxy)-5-(pyrrolidin-1-yl)picolinamido)butanoic acid (example 33 f) was reacted with 1-iodo-3-fluoropropane to give the title compound as colorless oil, MS (ESI): 482.4 [MH$^+$].

Example 36

Pharmacological Tests

The following tests were carried out in order to determine the activity of the compounds of formula I:

Radioligand Binding Assay

The affinity of the compounds of the invention for cannabinoid CB1 receptors was determined using recommended amounts of membrane preparations (PerkinElmer) of human embryonic kidney (HEK) cells expressing the human CNR1 or CNR2 receptors in conjunction with 1.5 or 2.6 nM [3H]-CP-55,940 (Perkin Elmer) as radioligand, respectively. Binding was performed in binding buffer (50 mM Tris, 5 mM MgCl2, 2.5 mM EDTA, and 0.5% (wt/vol) fatty acid free BSA, pH 7.4 for CB1 receptor and 50 mM Tris, 5 mM MgCl2, 2.5 mM EGTA, and 0.1% (wt/vol) fatty acid free BSA, pH 7.4 for CB2 receptor) in a total volume of 0.2 ml for 1 h at 30° C. shaking. The reaction was terminated by rapid filtration through microfiltration plates coated with 0.5% polyethylenimine (UniFilter GFB filter plate; Packard). Bound radioactivity was analyzed for Ki using nonlinear regression analysis (Activity Base, ID Business Solution, Limited), with the Kd values for [3H]CP55,940 determined from saturation experiments. The compounds of formula (I) show an excellent affinity for the CB2 receptor.

The compounds according to formula (I) have an activity in the above assay (Ki) between 0.5 nM and 10 µM. Particular compounds of formula (I) have an activity in the above assay (Ki) between 0.5 nM and 3 µM. Other particular compounds of formula (I) have an activity in the above assay (Ki) between 0.5 nM and 100 nM.

cAMP Assay

CHO cells expressing human CB1 or CB2 receptors are seeded 17-24 hours prior to the experiment 50.000 cells per well in a black 96 well plate with flat clear bottom (Corning Costar #3904) in DMEM (Invitrogen No. 31331), 1×HT supplement, with 10% fetal calf serum and incubated at 5% $CO_2$ and 37° C. in a humidified incubator. The growth medium was exchanged with Krebs Ringer Bicarbonate buffer with 1 mM IBMX and incubated at 30° C. for 30 min. Compounds were added to a final assay volume of 100 µl and incubated for 30 min at 30° C. Using the cAMP-Nano-TRF detection kit the assay (Roche Diagnostics) was stopped by the addition of 50 µl lysis reagent (Tris, NaCl, 1.5% Triton X100, 2.5% NP40, 10% NaN$_3$) and 50 µl detection solutions (20 µM mAb Alexa700-cAMP 1:1, and 48 µM Ruthenium-2-AHA-cAMP) and shaken for 2 h at room temperature. The time-resolved energy transfer is measured by a TRF reader (Evotec Technologies GmbH), equipped with a ND:YAG laser as excitation source. The plate is measured twice with the excitation at 355 nm and at the emission with a delay of 100 ns and a gate of 100 ns, total exposure time 10 s at 730 (bandwidth 30 nm) or 645 nm (bandwidth 75 nm), respectively. The FRET signal is calculated as follows: FRET=T730-Alexa730-P(T645-B645) with P=Ru730-B730/Ru645-B645, where T730 is the test well measured at 730 nM, T645 is the test well measured at 645 nm, B730 and B645 are the buffer controls at 730 nm and 645 nm, respectively. cAMP content is determined from the function of a standard curve spanning from 10 µM to 0.13 nM cAMP.

EC$_{50}$ values were determined using Activity Base analysis (ID Business Solution, Limited). The EC$_{50}$ values for a wide range of cannabinoid agonists generated from this assay for reference compounds were in agreement with the values published in the scientific literature.

In the foregoing assay, the compounds according to the invention have a human CB2 EC$_{50}$ which is between 0.5 nM and 10 µM. Particular compounds according to the invention have a human CB2 EC$_{50}$ between 0.5 nM and µM. Further particular compounds according to the invention have a human CB2 EC$_{50}$ between 0.5 nM and 100 nM. They exhibit at least 10 fold selectivity against the human CB1 receptor in, either both of the radioligand and cAMP assay, or in one of these two assays.

Results obtained for representative compounds of the invention are given in the following table.

| Example | Binding assay human CB2 Ki [µM] |
|---|---|
| 1 | 0.0018 |
| 2 | 0.0037 |
| 3 | 0.0005 |
| 4 | 0.0007 |
| 5 | 0.0046 |
| 6 | 0.013 |
| 7 | 0.0025 |
| 8 | 0.1429 |
| 9 | 0.0002 |
| 10 | 0.0082 |
| 11 | 0.0097 |
| 12 | 0.0004 |
| 13 | 0.0003 |
| 14 | 0.0114 |
| 15 | 0.0007 |
| 16 | 0.0188 |
| 17 | 0.3311 |
| 18 | 0.021 |
| 19 | 0.0008 |
| 20 | 0.5251 |
| 22 | 0.7551 |
| 23 | 0.0216 |
| 24 | 0.0655 |
| 25 | 0.0018 |
| 26 | 0.1295 |
| 27 | 4.1533 |
| 28 | 3.945 |
| 29 | 0.0109 |
| 30 | 0.0017 |
| 31 | 0.0117 |
| 32 | 0.2462 |

-continued

| Example | Binding assay human CB2 Ki [µM] |
|---|---|
| 33 | 0.348 |
| 34 | 0.6069 |
| 35 | 1.388 |

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| Compound of formula (I) | 3.0 mg |
|---|---|
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

The invention claimed is:

1. A compound of formula (I)

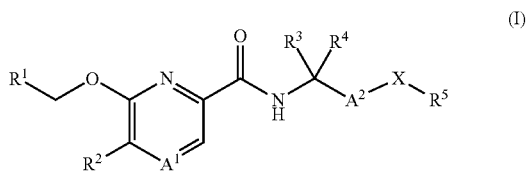

wherein
A$^1$ is —CH— or nitrogen;
A$^2$ is —CH$_2$— or carbonyl;
R$^1$ is haloalkoxyalkylcycloalkyl, haloalkylcycloalkyl, haloalkoxyalkyl, hydroxyalkylcycloalkyl, oxetanyl, haloalkoxyalkyloxetanyl, hydroxyalkyloxetanyl, haloalkyloxetanyl, 1-fluoroethyl, 1-fluoro-prop-2-yl, fluoro-tert.-butyl, cyclopropylfluoromethyl, fluorocyclopropyl, halooxanyl, halotetrahydrofuranyl, phenylalkoxyalkylcycloalkyl, 1-fluoro-1,1-dideuteroprop-2-yl, fluorodideuteromethyl, fluorodideuteromethyloxyalkylcycloalkyl, 2-fluoro-2,2-dideuteroethyloxyalkylcycloalkyl, fluorodideuteromethylcycloalkyl, fluorodideuteromethyloxyalkyl, fluorodideuteromethylalkyl, fluorodideuteromethyloxyalkyloxetanyl, 2-fluoro-2,2-dideuteroethyloxyalkyloxetanyl, 3-fluoro-3,3-dideuteropropyloxyalkyloxetanyl or fluorodideuteromethyloxetanyl;
R$^2$ is alkoxyazetidinyl, haloazetidinyl, dihaloazetidinyl, pyrrolidinyl or alkylphenylsulfonyloxyazetidinyl;
R$^3$ and R$^4$ are independently selected from hydrogen, alkyl, alkenyl and deuterioalkyl;
R$^5$ is hydrogen, alkyl, haloalkyl, deuterioalkyl, alkylphenylsulfonyloxyalkyl, alkylphenylsulfonyloxydeuterioalkyl or hydroxyalkyl; and
X is oxygen or —NH—;
or a pharmaceutically acceptable salt thereof.

2. The compound of claim 1, wherein A$^1$ is —CH—.

3. The compound of claim 1, wherein A$^2$ is carbonyl.

4. The compound of claim 1, wherein R$^1$ is haloalkoxyalkylcycloalkyl, haloalkylcycloalkyl or hydroxyalkylcycloalkyl.

5. The compound of claim 4, wherein R$^1$ is fluoromethoxymethylcyclopropyl, fluoromethylcyclopropyl or hydroxmethylcyclopropyl.

6. The compound of claim 1, wherein R$^2$ is alkoxyazetidinyl or haloazetidinyl.

7. The compound of claim 6, wherein R$^2$ is methoxyazetidinyl or fluoroazetidinyl.

8. The compound of claim 1, wherein R$^3$ and R$^4$ are both alkyl at the same time or both deuterioalkyl at the same time.

9. The compound claim 8, wherein R$^3$ and R$^4$ are both ethyl at the same time or both dideuterioethyl at the same time.

10. The compound of claim 1, wherein R$^5$ is alkyl, haloalkyl or halodeuterioalkyl.

11. The compound of claim 10, wherein R$^5$ is ethyl, fluoromethyl, fluoropropyl, fluorobutyl or fluorohexadeuteriopropyl.

12. The compound of claim 1, wherein X is oxygen.

13. The compound of claim 1 selected from the group consisting of:

Ethyl 2-ethyl-2-{[6-({(1S,2S)-2-[(fluoromethoxy)methyl]cyclopropyl}methoxy)-5-(3-methoxyazetidin-1-yl)pyridine-2-carbonyl]amino}butanoate;

ethyl 2-ethyl-2-{[6-({(1R,2R)-2-[(fluoromethoxy)methyl]cyclopropyl}methoxy)-5-(3-methoxyazetidin-1-yl)pyridine-2-caronyl]amino}butanoate;

Ethyl 2-ethyl-2-{[6-({(1S,2S)-2-[(2-fluoroethoxy)methyl]cyclopropyl}methoxy)-5-(3-methoxyazetidin-1-yl)pyridine-2-carbonyl]amino}butanoate;

ethyl 2-ethyl-2-{[6-({(1R,2R)-2-[(2-fluoroethoxy)methyl]cyclopropyl}methoxy)-5-(3-methoxyazetidin-1-yl)pyridine-2-carbonyl]amino}butanoate;

Ethyl 2-ethyl-2-{[6-{[(1S,2S)-2-(fluoromethyl)cyclopropyl]methoxy}-5-(3-methoxyazetidin-1-yl)pyridine-2-carbonyl]amino}butanoate and ethyl 2-ethyl-2-{[6-{[(1R,R)-2-(fluoromethyl)cyclopropyl]methoxy}-5-(3-methoxyazetidin-1-yl)pyridine-2-carbonyl]amino}butanoate;

Ethyl 2-ethyl-2-{[6-{[(1R,2S)-2-(fluoromethyl)cyclopropyl]methoxy}-5-(3-methoxyazetidin-1-yl)pyridine-2-carbonyl]amino}butanoate and ethyl 2-ethyl-2-{[6-{[(1S,2R)-2-(fluoromethyl)cyclopropyl]methoxy}-5-(3-methoxyazetidin-1-yl)pyridine-2-carbonyl]amino}butanoate;

Ethyl 2-ethyl-2-{[6-({(1R,2S)-2-[(fluoromethoxy)methyl]cyclopropyl}methoxy)-5-(3-methoxyazetidin-1-yl)pyridine-2-carbonyl]amino}butanoate;

ethyl 2-ethyl-2-{[6-({(1S,2R)-2-[(fluoromethoxy)methyl]cyclopropyl}methoxy)-5-(3-methoxyazetidin-1-yl)pyridine-2-carbonyl]amino}butanoate;

Ethyl 2-ethyl-2-{[6-({(1R,2S)-2-[(2-fluoroethoxy)methyl]cyclopropyl}methoxy)-5-(3-methoxyazetidin-1-yl)pyridine-2-carbonyl]amino}butanoate;

ethyl 2-ethyl-2-{[6-({(1S,2R)-2-[(2-fluoroethoxy)methyl]cyclopropyl}methoxy)-5-(3-methoxyazetidin-1-yl)pyridine-2-carbonyl]amino}butanoate;

Ethyl 2-ethyl-2-({6-[3-(fluoromethoxy)-2,2-dimethylpropoxy]-5-(3-methoxyazetidin-1-yl)pyridine-2-carbonyl}amino)butanoate;

(+)-trans-Ethyl 2-ethyl-2-{[6-({-2-[(fluoromethoxy)methyl]cyclopropyl}methoxy)-5-(3-methoxyazetidin-1-yl)pyridine-2-carbonyl]amino}butanoate;

(−)-trans-Ethyl 2-ethyl-2-{[6-({-2-[(fluoromethoxy)methyl]cyclopropyl}methoxy)-5-(3-methoxyazetidin-1-yl)pyridine-2-carbonyl]amino}butanoate;

ethyl 2-ethyl-2-{[6-({(1R,2S)-2-[(fluoromethoxy)methyl]cyclopropyl}methoxy)-5-(3-methoxyazetidin-1-yl)pyridine-2-carbonyl]amino}butanoate ethyl 2-ethyl-2-{[6-({(1S,2R)-2-[(fluoromethoxy)methyl]cyclopropyl}methoxy)-5-(3-methoxyazetidin-1-yl)pyridine-2-carbonyl]amino}butanoate;

(−)-trans-Fluoromethyl 2-ethyl-2-{[6-{[(1R,2R)-2-(hydroxymethyl)cyclopropyl]methoxy}-5-(3-methoxyazetidin-1-yl)pyridine-2-carbonyl]amino}butanoate; (+)-trans-Fluoromethyl 2-ethyl-2-{[6-{[-2-(hydroxymethyl)cyclopropyl]methoxy}-5-(3-methoxyazetidin-1-yl)pyridine-2-carbonyl]amino}butanoate;

(+)-trans-2-Fluoroethyl 2-ethyl-2-{[6-{[-2-(hydroxymethyl)cyclopropyl]methoxy}-5-(3-methoxyazetidin-1-yl)pyridine-2-carbonyl]amino}butanoate;

(−)-trans-2-Fluoroethyl 2-ethyl-2-{[6-{[-2-(hydroxymethyl)cyclopropyl]methoxy}-5-(3-methoxyazetidin-1-yl)pyridine-2-carbonyl]amino}butanoate;

3-Fuoropropyl 2-ethyl-2-{[6-{[(1S,2S)-2-(hydroxymethyl)cyclopropyl]methoxy}-5-(3-methoxyazetidin-1-yl)pyridine-2-carbonyl]amino}butanoate;

3-Fuoropropyl 2-ethyl-2-{[6-{[(1R,2R)-2-(hydroxymethyl)cyclopropyl]methoxy}-5-(3-methoxyazetidin-1-yl)pyridine-2-carbonyl]amino}butanoate;

N-[(2S)-1-(fluoromethoxy)propan-2-yl]-6-{[(1S,2S)-2-(hydroxymethyl)cyclopropyl]methoxy}-5-(3-methoxyazetidin-1-yl)pyridine-2-carboxamide;

N-[(2S)-1-(2-fluoroethoxy)propan-2-yl]-6-{[(1S,2S)-2-(hydroxymethyl)cyclopropyl]methoxy}-5-(3-methoxyazetidin-1-yl)pyridine-2-carboxamide;

N-[(2S)-1-(3-fluoropropoxy)propan-2-yl]-6-{[(1S,2S)-2-(hydroxymethyl)cyclopropyl]methoxy}-5-(3-methoxyazetidin-1-yl)pyridine-2-carboxamide;

N-[(2S)-1-(fluoromethoxy)-3-methylbutan-2-yl]-6-{[(1S,2S)-2-(hydroxymethyl)cyclopropyl]methoxy}-5-(3-methoxyazetidin-1-yl)pyridine-2-carboxamide;

N-[(2S)-1-(2-fluoroethoxy)-3-methylbutan-2-yl]-6-{[(1S,2S)-2-(hydroxymethyl)cyclopropyl]methoxy}-5-(3-methoxyazetidin-1-yl)pyridine-2-carboxamide;

N-[(2S)-1-(3-fluoropropoxy)-3-methylbutan-2-yl]-6-{[(1S,2S)-2-(hydroxymethyl)cyclopropyl]methoxy}-5-(3-methoxyazetidin-1-yl)pyridine-2-carboxamide;

N-[(2S)-1-(fluoromethoxy)-4-methylpentan-2-yl]-6-{[(1S,2S)-2-(hydroxymethyl)cyclopropyl]methoxy}-5-(3-methoxyazetidin-1-yl)pyridine-2-carboxamide;

N-[(2S)-1-(2-fluoroethoxy)-4-methylpentan-2-yl]-6-{[(1S,2S)-2-(hydroxymethyl)cyclopropyl]methoxy}-5-(3-methoxyazetidin-1-yl)pyridine-2-carboxamide;

N-[(2S)-1-(3-fluoropropoxy)-4-methylpentan-2-yl]-6-{[(1S,2S)-2-(hydroxymethyl)cyclopropyl]methoxy}-5-(3-methoxyazetidin-1-yl)pyridine-2-carboxamide;

N-{3-[(fluoromethoxy)methyl]pentan-3-yl}-6-{[(1S,2S)-2-(hydroxymethyl)cyclopropyl]methoxy}-5-(3-methoxyazetidin-1-yl)pyridine-2-carboxamide;

N-{3-[(2-fluoroethoxy)methyl]pentan-3-yl}-6-{[(1S,2S)-2-(hydroxymethyl)cyclopropyl]methoxy}-5-(3-methoxyazetidin-1-yl)pyridine-2-carboxamide;

N-{3-[(3-fluoropropoxy)methyl]pentan-3-yl}-6-{[(1S,2S)-2-(hydroxymethyl)cyclopropyl]methoxy}-5-(3-methoxyazetidin-1-yl)pyridine-2-carboxamide;

fluoromethyl 2-ethyl-2-{[6-{[(1R,2S)-2-(hydroxymethyl)cyclopropyl]methoxy}-5-(3-methoxyazetidin-1-yl)pyridine-2-carbonyl]amino}butanoate;

2-fluoroethyl 2-ethyl-2-{[6-{[(1R,2S)-2-(hydroxymethyl)cyclopropyl]methoxy}-5-(3-methoxyazetidin-1-yl)pyridine-2-carbonyl]amino}butanoate;

3-fluoropropyl 2-ethyl-2-{[6-{[(1R,2S)-2-(hydroxymethyl)cyclopropyl]methoxy}-5-(3-methoxyazetidin-1-yl)pyridine-2-carbonyl]amino}butanoate;

N-[(2S)-1-(fluoromethoxy)propan-2-yl]-6-{[(1R,2S)-2-(hydroxymethyl)cyclopropyl]methoxy}-5-(3-methoxyazetidin-1-yl)pyridine-2-carboxamide;

N-[(2S)-1-(2-fluoroethoxy)propan-2-yl]-6-{[(1R,2S)-2-(hydroxymethyl)cyclopropyl]methoxy}-5-(3-methoxyazetidin-1-yl)pyridine-2-carboxamide;

N-[(2S)-1-(3-fluoropropoxy)propan-2-yl]-6-{[(1R,2S)-2-(hydroxymethyl)cyclopropyl]methoxy}-5-(3-methoxyazetidin-1-yl)pyridine-2-carboxamide;

N-[(2S)-1-(fluoromethoxy)-3-methylbutan-2-yl]-6-{[(1R,2S)-2-(hydroxymethyl)cyclopropyl]methoxy}-5-(3-methoxyazetidin-1-yl)pyridine-2-carboxamide;

N-[(2S)-1-(2-fluoroethoxy)-3-methylbutan-2-yl]-6-{[(1R,2S)-2-(hydroxymethyl)cyclopropyl]methoxy}-5-(3-methoxyazetidin-1-yl)pyridine-2-carboxamide;

N-[(2S)-1-(3-fluoropropoxy)-3-methylbutan-2-yl]-6-{[(1R,2S)-2-(hydroxymethyl)cyclopropyl]methoxy}-5-(3-methoxyazetidin-1-yl)pyridine-2-carboxamide;

N-[(2S)-1-(fluoromethoxy)-4-methylpentan-2-yl]-6-{[(1R,2S)-2-(hydroxymethyl)cyclopropyl]methoxy}-5-(3-methoxyazetidin-1-yl)pyridine-2-carboxamide;

N-[(2S)-1-(2-fluoroethoxy)-4-methylpentan-2-yl]-6-{[(1R,2S)-2-(hydroxymethyl)cyclopropyl]methoxy}-5-(3-methoxyazetidin-1-yl)pyridine-2-carboxamide;

N-[(2S)-1-(3-fluoropropoxy)-4-methylpentan-2-yl]-6-{[(1R,2S)-2-(hydroxymethyl)cyclopropyl]methoxy}-5-(3-methoxyazetidin-1-yl)pyridine-2-carboxamide;

N-{3-[(fluoromethoxy)methyl]pentan-3-yl}-6-{[(1R,2S)-2-(hydroxymethyl)cyclopropyl]methoxy}-5-(3-methoxyazetidin-1-yl)pyridine-2-carboxamide;

N-{3-[(2-fluoroethoxy)methyl]pentan-3-yl}-6-{[(1R,2S)-2-(hydroxymethyl)cyclopropyl]methoxy}-5-(3-methoxyazetidin-1-yl)pyridine-2-carboxamide;

N-{3-[(3-fluoropropoxy)methyl]pentan-3-yl}-6-{[(1R,2S)-2-(hydroxymethyl)cyclopropyl]methoxy}-5-(3-methoxyazetidin-1-yl)pyridine-2-carboxamide;

fluoromethyl 2-ethyl-2-({5-(3-methoxyazetidin-1-yl)-6-[(oxetan-3-yl)methoxy]pyridine-2-carbonyl}amino)butanoate;

2-fluoroethyl 2-ethyl-2-({5-(3-methoxyazetidin-1-yl)-6-[(oxetan-3-yl)methoxy]pyridine-2-carbonyl}amino)butanoate;

3-fluoropropyl 2-ethyl-2-({5-(3-methoxyazetidin-1-yl)-6-[(oxetan-3-yl)methoxy]pyridine-2-carbonyl}amino)butanoate;

N-[(2S)-1-(fluoromethoxy)propan-2-yl]-5-(3-methoxyazetidin-1-yl)-6-[(oxetan-3-yl)methoxy]pyridine-2-carboxamide;

N-[(2S)-1-(2-fluoroethoxy)propan-2-yl]-5-(3-methoxyazetidin-1-yl)-6-[(oxetan-3-yl)methoxy]pyridine-2-carboxamide;

N-[(2S)-1-(3-fluoropropoxy)propan-2-yl]-5-(3-methoxyazetidin-1-yl)-6-[(oxetan-3-yl)methoxy]pyridine-2-carboxamide;

N-[(2S)-1-(fluoromethoxy)-3-methylbutan-2-yl]-5-(3-methoxyazetidin-1-yl)-6-[(oxetan-3-yl)methoxy]pyridine-2-carboxamide;

N-[(2S)-1-(2-fluoroethoxy)-3-methylbutan-2-yl]-5-(3-methoxyazetidin-1-yl)-6-[(oxetan-3-yl)methoxy]pyridine-2-carboxamide;

N-[(2S)-1-(3-fluoropropoxy)-3-methylbutan-2-yl]-5-(3-methoxyazetidin-1-yl)-6-[(oxetan-3-yl)methoxy]pyridine-2-carboxamide;

N-[(2S)-1-(fluoromethoxy)-4-methylpentan-2-yl]-5-(3-methoxyazetidin-1-yl)-6-[(oxetan-3-yl)methoxy]pyridine-2-carboxamide;

N-[(2S)-1-(2-Fluoroethoxy)-4-methylpentan-2-yl]-5-(3-methoxyazetidin-1-yl)-6-[(oxetan-3-yl)methoxy]pyridine-2-carboxamide;

N-[(2S)-1-(3-fluoropropoxy)-4-methylpentan-2-yl]-5-(3-methoxyazetidin-1-yl)-6-[(oxetan-3-yl)methoxy]pyridine-2-carboxamide;

N-{3-[(fluoromethoxy)methyl]pentan-3-yl}-5-(3-methoxyazetidin-1-yl)-6-[(oxetan-3-yl)methoxy]pyridine-2-carboxamide;

N-{3-[(2-fluoroethoxy)methyl]pentan-3-yl}-5-(3-methoxyazetidin-1-yl)-6-[(oxetan-3-yl)methoxy]pyridine-2-carboxamide;

N-{3-[(3-fluoropropoxy)methyl]pentan-3-yl}-5-(3-methoxyazetidin-1-yl)-6-[(oxetan-3-yl)methoxy]pyridine-2-carboxamide;

N-[(2S)-1-(2-Fluoroethoxy)-4-methylpentan-2-yl]-6-[(oxetan-3-yl)methoxy]-5-(pyrrolidin-1-yl)pyridine-2-carboxamide;

ethyl 2-ethyl-2-{[6-({3-[(fluoromethoxy)methyl]oxetan-3-yl}methoxy)-5-(3-methoxyazetidin-1-yl)pyridine-2-carbonyl]amino}butanoate;

ethyl 2-ethyl-2-{[6-({3-[(2-fluoroethoxy)methyl]oxetan-3-yl}methoxy)-5-(3-methoxyazetidin-1-yl)pyridine-2-carbonyl]amino}butanoate;

ethyl 2-ethyl-2-{[6-({3-[(3-fluoropropoxy)methyl]oxetan-3-yl}methoxy)-5-(3-methoxyazetidin-1-yl)pyridine-2-carbonyl]amino}butanoate;

fluoromethyl 2-ethyl-2-{[6-{[3-(hydroxymethyl)oxetan-3-yl]methoxy}-5-(3-methoxyazetidin-1-yl)pyridine-2-carbonyl]amino}butanoate;

2-fluoroethyl 2-ethyl-2-{[6-{[3-(hydroxymethyl)oxetan-3-yl]methoxy}-5-(3-methoxyazetidin-1-yl)pyridine-2-carbonyl]amino}butanoate;

3-fluoropropyl 2-ethyl-2-{[6-{[3-(hydroxymethyl)oxetan-3-yl]methoxy}-5-(3-methoxyazetidin-1-yl)pyridine-2-carbonyl]amino}butanoate;

N-[(2S)-1-(fluoromethoxy)propan-2-yl]-6-{[3-(hydroxymethyl)oxetan-3-yl]methoxy}-5-(3-methoxyazetidin-1-yl)pyridine-2-carboxamide;

N-[(2S)-1-(2-fluoroethoxy)propan-2-yl]-6-{[3-(hydroxymethyl)oxetan-3-yl]methoxy}-5-(3-methoxyazetidin-1-yl)pyridine-2-carboxamide;

N-[(2S)-1-(3-fluoropropoxy)propan-2-yl]-6-{[3-(hydroxymethyl)oxetan-3-yl]methoxy}-5-(3-methoxyazetidin-1-yl)pyridine-2-carboxamide;

N-[(2S)-1-(fluoromethoxy)-3-methylbutan-2-yl]-6-{[3-(hydroxymethyl)oxetan-3-yl]methoxy}-5-(3-methoxyazetidin-1-yl)pyridine-2-carboxamide;

N-[(2S)-1-(2-fluoroethoxy)-3-methylbutan-2-yl]-6-{[3-(hydroxymethyl)oxetan-3-yl]methoxy}-5-(3-methoxyazetidin-1-yl)pyridine-2-carboxamide;

N-[(2S)-1-(3-fluoropropoxy)-3-methylbutan-2-yl]-6-{[3-(hydroxymethyl)oxetan-3-yl]methoxy}-5-(3-methoxyazetidin-1-yl)pyridine-2-carboxamide;

N-[(2S)-1-(fluoromethoxy)-4-methylpentan-2-yl]-6-{[3-(hydroxymethyl)oxetan-3-yl]methoxy}-5-(3-methoxyazetidin-1-yl)pyridine-2-carboxamide;

N-[(2S)-1-(2-fluoroethoxy)-4-methylpentan-2-yl]-6-{[3-(hydroxymethyl)oxetan-3-yl]methoxy}-5-(3-methoxyazetidin-1-yl)pyridine-2-carboxamide;

N-[(2S)-1-(3-fluoropropoxy)-4-methylpentan-2-yl]-6-{[3-(hydroxymethyl)oxetan-3-yl]methoxy}-5-(3-methoxyazetidin-1-yl)pyridine-2-carboxamide;

N-{3-[(fluoromethoxy)methyl]pentan-3-yl}-6-{[3-(hydroxymethyl)oxetan-3-yl]methoxy}-5-(3-methoxyazetidin-1-yl)pyridine-2-carboxamide;

N-{3-[(2-fluoroethoxy)methyl]pentan-3-yl}-6-{[3-(hydroxymethyl)oxetan-3-yl]methoxy}-5-(3-methoxyazetidin-1-yl)pyridine-2-carboxamide;

N-{3-[(3-fluoropropoxy)methyl]pentan-3-yl}-6-{[3-(hydroxymethyl)oxetan-3-yl]methoxy}-5-(3-methoxyazetidin-1-yl)pyridine-2-carboxamide;

6-({(1S,2S)-2-[(fluoromethoxy)methyl]cyclopropyl}methoxy)-N-[(2S)-1-hydroxy-4-methylpentan-2-yl]-5-(3-methoxyazetidin-1-yl)pyridine-2-carboxamide;

6-({(1S,2S)-2-[(2-fluoroethoxy)methyl]cyclopropyl}methoxy)-N-[(2S)-1-hydroxy-4-methylpentan-2-yl]-5-(3-methoxyazetidin-1-yl)pyridine-2-carboxamide;

6-({(1S,2S)-2-[(3-fluoropropoxy)methyl]
cyclopropyl}methoxy)-N-[(2S)-1-hydroxy-4-methyl-pentan-2-yl]-5-(3-methoxyazetidin-1-yl)pyridine-2-carboxamide;

6-{[(1S,2S)-2-(fluoromethyl)cyclopropyl]methoxy}-N-[(2S)-1-hydroxy-4-methylpentan-2-yl]-5-(3-methoxyazetidin-1-yl)pyridine-2-carboxamide;

6-({(1R,2S)-2-[(fluoromethoxy)methyl]
cyclopropyl}methoxy)-N-[(2S)-1-hydroxy-3-methylbutan-2-yl]-5-(3-methoxyazetidin-1-yl)pyridine-2-carboxamide;

6-({(1R,2S)-2-[(2-fluoroethoxy)methyl]
cyclopropyl}methoxy)-N-[(2S)-1-hydroxy-3-methylbutan-2-yl]-5-(3-methoxyazetidin-1-yl)pyridine-2-carboxamide;

6-({(1R,2S)-2-[(3-fluoropropoxy)methyl]
cyclopropyl}methoxy)-N-[(2S)-1-hydroxy-3-methylbutan-2-yl]-5-(3-methoxyazetidin-1-yl)pyridine-2-carboxamide;

6-{[(1R,2S)-2-(fluoromethyl)cyclopropyl]methoxy}-N-[(2S)-1-hydroxy-3-methylbutan-2-yl]-5-(3-methoxyazetidin-1-yl)pyridine-2-carboxamide;

6-({3-[(fluoromethoxy)methyl]oxetan-3-yl}methoxy)-N-[(2S)-1-hydroxypropan-2-yl]-5-(3-methoxyazetidin-1-yl)pyridine-2-carboxamide;

6-({3-[(2-fluoroethoxy)methyl]oxetan-3-yl}methoxy)-N-[(2S)-1-hydroxypropan-2-yl]-5-(3-methoxyazetidin-1-yl)pyridine-2-carboxamide;

6-({3-[(3-fluoropropoxy)methyl]oxetan-3-yl}methoxy)-N-[(2S)-1-hydroxypropan-2-yl]-5-(3-methoxyazetidin-1-yl)pyridine-2-carboxamide;

6-{[3-(fluoromethyl)oxetan-3-yl]methoxy}-N-[(2S)-1-hydroxypropan-2-yl]-5-(3-methoxyazetidin-1-yl)pyridine-2-carboxamide;

6-({3-[(fluoromethoxy)methyl]oxetan-3-yl}methoxy)-N-[3-(hydroxymethyl)pentan-3-yl]-5-(3-methoxyazetidin-1-yl)pyridine-2-carboxamide;

6-({3-[(2-fluoroethoxy)methyl]oxetan-3-yl}methoxy)-N-[3-(hydroxymethyl)pentan-3-yl]-5-(3-methoxyazetidin-1-yl)pyridine-2-carboxamide;

6-({3-[(3-fluoropropoxy)methyl]oxetan-3-yl}methoxy)-N-[3-(hydroxymethyl)pentan-3-yl]-5-(3-methoxyazetidin-1-yl)pyridine-2-carboxamide;

6-{[3-(fluoromethyl)oxetan-3-yl]methoxy}-N-[3-(hydroxymethyl)pentan-3-yl]-5-(3-methoxyazetidin-1-yl)pyridine-2-carboxamide;

ethyl 2-ethyl-2-{[6-({(1S,2S)-2-[(fluoromethoxy)methyl]
cyclopropyl}methoxy)-5-(3-methoxyazetidin-1-yl)pyrazine-2-carbonyl]amino}butanoate;

ethyl 2-ethyl-2-{[6-({(1R,2S)-2-[(fluoromethoxy)methyl]cyclopropyl}methoxy)-5-(3-methoxyazetidin-1-yl)pyrazine-2-carbonyl]amino}butanoate;

6-({(1S,2S)-2-[(3-fluoropropoxy)methyl]
cyclopropyl}methoxy)-N-[(2S)-1-hydroxy-4-methyl-pentan-2-yl]-5-(3-methoxyazetidin-1-yl)pyrazine-2-carboxamide;

6-({(1R,2S)-2-[(3-fluoropropoxy)methyl]
cyclopropyl}methoxy)-N-[(2S)-1-hydroxy-3-methylbutan-2-yl]-5-(3-methoxyazetidin-1-yl)pyrazine-2-carboxamide;

ethyl 2-ethyl-2-({6-[(3-fluorooxan-4-yl)methoxy]-5-(3-methoxyazetidin-1-yl)pyridine-2-carbonyl}amino)butanoate;

1,4-anhydro-2,3-dideoxy-5-O-[6-{[3-(ethoxycarbonyl)pentan-3-yl]carbamoyl}-3-(3-methoxyazetidin-1-yl)pyridin-2-yl]-2-fluoropentitol;

ethyl 2-ethyl-2-{[6-{[3-fluoro-2-methyl(3,3-dideuterio)propyl]oxy}-5-(3-methoxyazetidin-1-yl)pyridine-2-carbonyl]amino}butanoate;

ethyl 2-ethyl-2-{[6-{[2-fluoro(2,2-dideuterio)ethyl]oxy}-5-(3-methoxyazetidin-1-yl)pyridine-2-carbonyl]amino}butanoate;

ethyl 2-ethyl-2-({6-[(3-fluorooxan-4-yl)methoxy]-5-(3-methoxyazetidin-1-yl)pyridine-2-carbonyl}amino)butanoate;

1,4-anhydro-2,3-dideoxy-5-O-[6-{[3-(ethoxycarbonyl)pentan-3-yl]carbamoyl}-3-(3-methoxyazetidin-1-yl)pyridin-2-yl]-2-fluoropentitol;

ethyl 2-ethyl-2-{[6-{[(1S,2S)-2-({[fluoro(dideuterio)methyl]oxy}methyl)cyclopropyl]methoxy}-5-(3-methoxyazetidin-1-yl)pyridine-2-carbonyl]amino}butanoate;

ethyl 2-ethyl-2-{[6-{[(1S,2S)-2-({[2-fluoro(2,2-~2~H_2_)ethyl]oxy}methyl)cyclopropyl]methoxy}-5-(3-methoxyazetidin-1-yl)pyridine-2-carbonyl]amino}butanoate;

ethyl 2-ethyl-2-{[6-({(1S,2S)-2-[fluoro(dideuterio)methyl]cyclopropyl}methoxy)-5-(3-methoxyazetidin-1-yl)pyridine-2-carbonyl]amino}butanoate;

ethyl 2-ethyl-2-{[6-({(1R,2S)-2-[fluoro(dideuterio)methyl]cyclopropyl}methoxy)-5-(3-methoxyazetidin-1-yl)pyridine-2-carbonyl]amino}butanoate;

ethyl 2-ethyl-2-{[6-{[(1R,2S)-2-({[fluoro(dideuterio)methyl]oxy}methyl)cyclopropyl]methoxy}-5-(3-methoxyazetidin-1-yl)pyridine-2-carbonyl]amino}butanoate;

ethyl 2-ethyl-2-{[6-{[(1R,2S)-2-({[2-fluoro(2,2-dideuterio)ethyl]oxy}methyl)cyclopropyl]methoxy}-5-(3-methoxyazetidin-1-yl)pyridine-2-carbonyl]amino}butanoate;

ethyl 2-ethyl-2-{[6-(3-{[fluoro(dideuterio)methyl]oxy}-2,2-dimethylpropoxy)-5-(3-methoxyazetidin-1-yl)pyridine-2-carbonyl]amino}butanoate;

ethyl 2-ethyl-2-{[6-{[3-fluoro-2,2-dimethyl(3,3-dideuterio)propyl]oxy}-5-(3-methoxyazetidin-1-yl)pyridine-2-carbonyl]amino}butanoate;

ethyl 2-ethyl-2-{[6-{[(1S,2S)-2-({[fluoro(dideuterio)methyl]oxy}methyl)cyclopropyl]methoxy}-5-(3-methoxyazetidin-1-yl)pyridine-2-carbonyl]amino}butanoate;

ethyl 2-ethyl-2-{[6-{[(1R,2R)-2-({[fluoro(dideuterio)methyl]oxy}methyl)cyclopropyl]methoxy}-5-(3-methoxyazetidin-1-yl)pyridine-2-carbonyl]amino}butanoate;

ethyl 2-ethyl-2-{[6-{[3-fluoro-2-methyl(3,3-dideuterio)propyl]oxy}-5-(3-methoxyazetidin-1-yl)pyridine-2-carbonyl]amino}butanoate;

ethyl 2-ethyl-2-{[6-{[2-fluoro(2,2-dideuterio)ethyl]oxy}-5-(3-methoxyazetidin-1-yl)pyridine-2-carbonyl]amino}butanoate;

ethyl 2-ethyl-2-{[6-{[3-fluoro-2-methyl(3,3-dideuterio)propyl]oxy}-5-(3-methoxyazetidin-1-yl)pyridine-2-carbonyl]amino}butanoate;

ethyl 2-ethyl-2-{[6-{[3-fluoro-2-methyl(3,3-dideuterio)propyl]oxy}-5-(3-methoxyazetidin-1-yl)pyridine-2-carbonyl]amino}butanoate;

ethyl 2-ethyl-2-{[6-{[2-fluoro(2,2-dideuterio)ethyl]oxy}-5-(3-methoxyazetidin-1-yl)pyridine-2-carbonyl]amino}butanoate;

ethyl 2-ethyl-2-{[6-{[3-fluoro-2-methyl(3,3-dideuterio)propyl]oxy}-5-(3-methoxyazetidin-1-yl)pyridine-2-carbonyl]amino}butanoate;

6-{[3-({[fluoro(dideuterio)methyl]oxy}methyl)oxetan-3-yl]methoxy}-N-[(2S)-1-hydroxypropan-2-yl]-5-(3-methoxyazetidin-1-yl)pyridine-2-carboxamide;

6-{[3-({[2-fluoro(2,2-dideuterio)ethyl]oxy}methyl)oxetan-3-yl]methoxy}-N-[(2S)-1-hydroxypropan-2-yl]-5-(3-methoxyazetidin-1-yl)pyridine-2-carboxamide;

6-{[3-({[3-fluoro(3,3-dideuterio)propyl]oxy}methyl)oxetan-3-yl]methoxy}-N-[(2S)-1-hydroxypropan-2-yl]-5-(3-methoxyazetidin-1-yl)pyridine-2-carboxamide;

6-({3-[fluoro(dideuterio)methyl]oxetan-3-yl}methoxy)-N-[(2S)-1-hydroxypropan-2-yl]-5-(3-methoxyazetidin-1-yl)pyridine-2-carboxamide;

6-{[3-({[fluoro(dideuterio)methyl]oxy}methyl)oxetan-3-yl]methoxy}-N-[3-(hydroxymethyl)pentan-3-yl]-5-(3-methoxyazetidin-1-yl)pyridine-2-carboxamide;

6-{[3-({[2-fluoro(2,2-dideuterio)ethyl]oxy}methyl)oxetan-3-yl]methoxy}-N-[3-(hydroxymethyl)pentan-3-yl]-5-(3-methoxyazetidin-1-yl)pyridine-2-carboxamide;

6-{[3-({[3-fluoro(3,3-dideuterio)propyl]oxy}methyl)oxetan-3-yl]methoxy}-N-[3-(hydroxymethyl)pentan-3-yl]-5-(3-methoxyazetidin-1-yl)pyridine-2-carboxamide;

6-({3-[fluoro(dideuterio)methyl]oxetan-3-yl}methoxy)-N-[3-(hydroxymethyl)pentan-3-yl]-5-(3-methoxyazetidin-1-yl)pyridine-2-carboxamide;

3-Fluoropropyl 3,4-dideuterio-2-(1,2-dideuterioethyl)-2-[[6-[[(1S,2S)-2-(hydroxymethyl)cyclopropyl]methoxy]-5-(3-methoxyazetidin-1-yl)pyridine-2-carbonyl]amino]butanoate;

fluoromethyl 2-ethyl-2-(6-((3-(hydroxymethyl)oxetan-3-yl)methoxy)-5-(pyrrolidin-1-yl)picolinamido)butanoate;

2-fluoroethyl 2-ethyl-2-(6-((3-(hydroxymethyl)oxetan-3-yl)methoxy)-5-(pyrrolidin-1-yl)picolinamido)butanoate;

3-fluoropropyl 2-ethyl-2-(6-((3-(hydroxymethyl)oxetan-3-yl)methoxy)-5-(pyrrolidin-1-yl)picolinamido)butanoate;

(1,1,2,2,3,3-Hexadeuterio-3-fluoro-propyl) 2-ethyl-2-[[6-[[(1S,2S)-2-(hydroxymethyl)cyclopropyl]methoxy]-5-(3-methoxyazetidin-1-yl)pyridine-2-carbonyl]amino]butanoate;

3-Fluoropropyl 2-[[6-[[(1S,2S)-2-(hydroxymethyl)cyclopropyl]methoxy]-5-(3-methoxyazetidin-1-yl)pyridine-2-carbonyl]amino]-2-vinyl-but-3-enoate;

3-Fluoropropyl 3,4-dideuterio-2-(1,2-dideuterioethyl)-2-[[6-[[(1S,2S)-2-(hydroxymethyl)cyclopropyl]methoxy]-5-(3-methoxyazetidin-1-yl)pyridine-2-carbonyl]amino]butanoate;

(Rac)-trans-3-Fluoropropyl 2-[[6-[[(1S,2S)-2-(benzyloxymethyl)cyclopropyl]methoxy]-5-(3-hydroxyazetidin-1-yl)pyridine-2-carbonyl]amino]-2-ethyl-butanoate;

3-(p-Tolylsulfonyloxy)propyl 2-ethyl-2-[[6-[[(1S,2S)-2-(hydroxymethyl)cyclopropyl]methoxy]-5-(3-methoxyazetidin-1-yl)pyridine-2-carbonyl]amino]butanoate;

[1,1,2,2,3,3-Hexadeuterio-3-(p-tolylsulfonyloxy)propyl] 2-ethyl-2-[[6-[[(1S,2S)-2-(hydroxymethyl)cyclopropyl]methoxy]-5-(3-methoxyazetidin-1-yl)pyridine-2-carbonyl]amino]butanoate;

4-Fluorobutyl 2-ethyl-2-[[6-[[(1S,2S)-2-(hydroxymethyl)cyclopropyl]methoxy]-5-(3-methoxyazetidin-1-yl)pyridine-2-carbonyl]amino]butanoate;

N-[1-Ethyl-1-[[(1S)-1-(hydroxymethyl)-3-methyl-butyl]carbamoyl]propyl]-6-[[(1S,2S)-2-(hydroxymethyl)cyclopropyl]methoxy]-5-(3-methoxyazetidin-1-yl)pyridine-2-carboxamide;

N-[1-ethyl-1-[[(1S)-1-(hydroxymethyl)-3-methyl-butyl]carbamoyl]propyl]-5-(3-fluoroazetidin-1-yl)-6-[[(1R,2R)-2-(hydroxymethyl)cyclopropyl]methoxy]pyridine-2-carboxamide;

N-[1-Ethyl-1-[[(1S)-1-(hydroxymethyl)-3-methyl-butyl]carbamoyl]propyl]-5-(3-fluoroazetidin-1-yl)-6-[[(1S,2S)-2-(hydroxymethyl)cyclopropyl]methoxy]pyridine-2-carboxamide;

3-Fluoropropyl 2-ethyl-2-{[5-(3-fluoroazetidin-1-yl)-6-{[(1R,2R)-2-(hydroxymethyl)cyclopropyl]methoxy}pyridin-2-yl]formamido}butanoate;

3-Fluoropropyl 2-ethyl-2-{[5-(3-fluoroazetidin-1-yl)-6-{[(1S,2S)-2-(hydroxymethyl)cyclopropyl]methoxy}pyridin-2-yl]formamido}butanoate;

(Rac)-trans-3-fluoropropyl 2-ethyl-2-[[6-[[-2-(hydroxymethyl)cyclopropyl]methoxy]-5-[3-(p-tolylsulfonyloxy)azetidin-1-yl]pyridine-2-carbonyl]amino]butanoate;

3-Fluoropropyl 2-[[6-[[(1S,2S)-2-(benzyloxymethyl)cyclopropyl]methoxy]-5-(3-methoxyazetidin-1-yl)pyridine-2-carbonyl]amino]-2-ethyl-butanoate;

ethyl 2-ethyl-2-{[6-(2-fluoropropoxy)-5-(3-methoxyazetidin-1-yl)pyridine-2-carbonyl]amino}butanoate;

ethyl 2-ethyl-2-{[6-(3-fluoro-2-methylpropoxy)-5-(3-methoxyazetidin-1-yl)pyridine-2-carbonyl]amino}butanoate;

ethyl 2-ethyl-2-{[6-(3-fluoro-2,2-dimethylpropoxy)-5-(3-methoxyazetidin-1-yl)pyridine-2-carbonyl]amino}butanoate;

ethyl 2-ethyl-2-{[6-(3-fluoro-2-methylpropoxy)-5-(3-methoxyazetidin-1-yl)pyridine-2-carbonyl]amino}butanoate;

ethyl 2-ethyl-2-({6-[(1-fluorocyclopropyl)methoxy]-5-(3-methoxyazetidin-1-yl)pyridine-2-carbonyl}amino)butanoate;

ethyl 2-ethyl-2-({6-[(2-fluorocyclopropyl)methoxy]-5-(3-methoxyazetidin-1-yl)pyridine-2-carbonyl}amino)butanoate;

ethyl 2-ethyl-2-{[6-(2-fluoropropoxy)-5-(3-methoxyazetidin-1-yl)pyridine-2-carbonyl]amino}butanoate;

ethyl 2-ethyl-2-{[6-(3-fluoro-2-methylpropoxy)-5-(3-methoxyazetidin-1-yl)pyridine-2-carbonyl]amino}butanoate;

ethyl 2-ethyl-2-{[6-(3-fluoro-2-methylpropoxy)-5-(3-methoxyazetidin-1-yl)pyridine-2-carbonyl]amino}butanoate;

ethyl 2-ethyl-2-({6-[(1-fluorocyclopropyl)methoxy]-5-(3-methoxyazetidin-1-yl)pyridine-2-carbonyl}amino)butanoate; and ethyl 2-ethyl-2-({6-[(2-fluorocyclopropyl)methoxy]-5-(3-methoxyazetidin-1-yl)pyridine-2-carbonyl}amino)butanoate;

or a pharmaceutically acceptable salt thereof.

14. The compound of claim 1 selected from the group consisting of:

Ethyl 2-ethyl-2-{[6-({(1S,2S)-2-[(fluoromethoxy)methyl]cyclopropyl}methoxy)-5-(3-methoxyazetidin-1-yl)pyridine-2-carbonyl]amino}butanoate and ethyl 2-ethyl-2-{[6-({(1R,2R)-2-[(fluoromethoxy)methyl]cyclopropyl}methoxy)-5-(3-methoxyazetidin-1-yl)pyridine-2-carbonyl]amino}butanoate;

Ethyl 2-ethyl-2-{[6-({(1S,2S)-2-[(2-fluoroethoxy)methyl]cyclopropyl}methoxy)-5-(3-methoxyazetidin-1-yl)pyridine-2-carbonyl]amino}butanoate;

ethyl 2-ethyl-2-{[6-({(1R,2R)-2-[(2-fluoroethoxy)methyl]cyclopropyl}methoxy)-5-(3-methoxyazetidin-1-yl)pyridine-2-carbonyl]amino}butanoate;
Ethyl 2-ethyl-2-{[6-{[(1R,2S)-2-(fluoromethyl)cyclopropyl]methoxy}-5-(3-methoxyazetidin-1-yl)pyridine-2-carbonyl]amino}butanoate;
ethyl 2-ethyl-2-{[6-{[(1S,2R)-2-(fluoromethyl)cyclopropyl]methoxy}-5-(3-methoxyazetidin-1-yl)pyridine-2-carbonyl]amino}butanoate;
Ethyl 2-ethyl-2-{[6-({(1R,2S)-2-[(fluoromethoxy)methyl]cyclopropyl}methoxy)-5-(3-methoxyazetidin-1-yl)pyridine-2-carbonyl]amino}butanoate;
ethyl 2-ethyl-2-{[6-({(1S,2R)-2-[(fluoromethoxy)methyl]cyclopropyl}methoxy)-5-(3-methoxyazetidin-1-yl)pyridine-2-carbonyl]amino}butanoate;
(+)-trans-Ethyl 2-ethyl-2-{[6({-2-[(fluoromethoxy)methyl]cyclopropyl}methoxy)-5-(3-methoxyazetidin-1-yl)pyridine-2-carbonyl]amino}butanoate;
(+)-trans-Fluoromethyl 2-ethyl-2-{[6-{[-2-(hydroxymethyl)cyclopropyl]methoxy}-5-(3-methoxyazetidin-1-yl)pyridine-2-carbonyl]amino}butanoate;
3-Fuoropropyl 2-ethyl-2-{[6-{[(1S,2S)-2-(hydroxymethyl)cyclopropyl]methoxy}-5-(3-methoxyazetidin-1-yl)pyridine-2-carbonyl]amino}butanoate; and
3-Fuoropropyl 2-ethyl-2-{[6-{[(1R,2R)-2-(hydroxymethyl)cyclopropyl]methoxy}-5-(3-methoxyazetidin-1-yl)pyridine-2-carbonyl]amino}butanoate;
or a pharmaceutically acceptable salt thereof.

15. A process for the preparation of the compound of claim 1, comprising one of the following steps:
(a) the reaction of a compound of formula (A1)

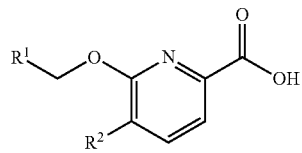

(A1)

with a compound of formula (A2)

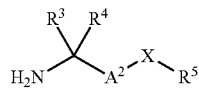

(A2)

in the presence of a coupling agent and a base;

(b) the reaction of a compound of formula (B)

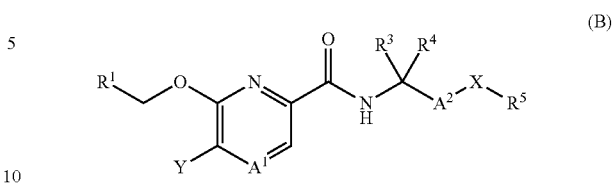

(B)

in the presence of R²M, a palladium catalyst and a base;
wherein:

$A^1$ is —CH— or nitrogen;

$A^2$ is —CH$_2$— or carbonyl;

$R^1$ is haloalkoxyalkylcycloalkyl, haloalkylcycloalkyl, haloalkoxyalkyl, hydroxyalkylcycloalkyl, oxetanyl, haloalkoxyalkyloxetanyl, hydroxyalkyloxetanyl, haloalkyloxetanyl, 1-fluoroethyl, 1-fluoro-prop-2-yl, fluoro-tert.-butyl, cyclopropylfluoromethyl, fluorocyclopropyl, halooxanyl, halotetrahydrofuranyl, phenylalkoxyalkylcycloalkyl, 1-fluoro-1,1-dideuteroprop-2-yl, fluorodideuteromethyl, fluorodideuteromethyloxyalkylcycloalkyl, 2-fluoro-2,2-dideuteroethyloxyalkylcycloalkyl, fluorodideuteromethylcycloalkyl, fluorodideuteromethyloxyalkyl, fluorodideuteromethylalkyl, fluorodideuteromethyloxyalkyloxetanyl, 2-fluoro-2,2-dideuteroethyloxyalkyloxetanyl, 3-fluoro-3,3-dideuteropropyloxyalkyloxetanyl or fluorodideuteromethyloxetanyl;

$R^2$ is alkoxyazetidinyl, haloazetidinyl, dihaloazetidinyl, pyrrolidinyl or alkylphenylsulfonyloxyazetidinyl;

$R^3$ and $R^4$ are independently selected from hydrogen, alkyl, alkenyl and deuterioalkyl;

$R^5$ is hydrogen, alkyl, haloalkyl, deuterioalkyl, alkylphenylsulfonyloxyalkyl, alkylphenylsulfonyloxydeuterioalkyl or hydroxyalkyl;

X is oxygen or —NH—; and

Y is halogen.

16. A pharmaceutical composition comprising a compound of claim 1, or a pharmaceutically acceptable salt thereof, and a therapeutically inert carrier.

* * * * *